US011669013B2

(12) United States Patent
Kanna

(10) Patent No.: US 11,669,013 B2
(45) Date of Patent: Jun. 6, 2023

(54) COMPOSITION FOR ELECTRODE PROTECTIVE FILM OF ELECTROSTATIC CAPACITANCE-TYPE INPUT DEVICE, ELECTRODE PROTECTIVE FILM OF ELECTROSTATIC CAPACITANCE-TYPE INPUT DEVICE, TRANSFER FILM, LAMINATE, ELECTROSTATIC CAPACITANCE-TYPE INPUT DEVICE, AND IMAGE DISPLAY DEVICE

(71) Applicant: FUJIFILM Corporation, Tokyo (JP)

(72) Inventor: Shinichi Kanna, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/898,318

(22) Filed: Feb. 16, 2018

(65) Prior Publication Data
US 2018/0173095 A1 Jun. 21, 2018

Related U.S. Application Data

(63) Continuation of application No. PCT/JP2016/078839, filed on Sep. 29, 2016.

(30) Foreign Application Priority Data

Sep. 30, 2015 (JP) .............................. JP2015-192459

(51) Int. Cl.
| | |
|---|---|
| *G03F 7/027* | (2006.01) |
| *G03F 7/033* | (2006.01) |
| *G03F 7/038* | (2006.01) |
| *C08F 265/06* | (2006.01) |
| *C09D 4/06* | (2006.01) |
| *G06F 3/041* | (2006.01) |
| *C08F 2/48* | (2006.01) |
| *G06F 3/044* | (2006.01) |
| *C07D 251/32* | (2006.01) |
| *C07D 403/12* | (2006.01) |
| *C08F 222/20* | (2006.01) |
| *C08J 5/18* | (2006.01) |
| *G03F 7/004* | (2006.01) |
| *G03F 7/031* | (2006.01) |

(52) U.S. Cl.
CPC ........... *G03F 7/033* (2013.01); *C07D 251/32* (2013.01); *C07D 403/12* (2013.01); *C08F 2/48* (2013.01); *C08F 222/20* (2013.01); *C08F 265/06* (2013.01); *C08J 5/18* (2013.01); *C09D 4/06* (2013.01); *G03F 7/0045* (2013.01); *G03F 7/027* (2013.01); *G03F 7/031* (2013.01); *G06F 3/041* (2013.01); *G06F 3/0443* (2019.05); *G06F 3/0446* (2019.05); *G06F 3/0448* (2019.05); *G06F 3/04164* (2019.05); *C08J 2335/02* (2013.01); *G06F 2203/04103* (2013.01); *G06F 2203/04111* (2013.01)

(58) Field of Classification Search
CPC ........... G03F 7/027; G03F 7/033; G03F 7/038
USPC .............................................. 430/281.1, 288.1
See application file for complete search history.

(56) References Cited

U.S. PATENT DOCUMENTS

| | | | | |
|---|---|---|---|---|
| 5,288,589 A | * | 2/1994 | McKeever | G03F 7/0955 430/262 |
| 6,432,612 B1 | * | 8/2002 | Hamada | G03F 7/0388 430/280.1 |
| 6,465,540 B1 | * | 10/2002 | Kubo | G03F 7/0388 522/100 |
| 7,198,884 B2 | * | 4/2007 | Oka | G03F 7/029 430/258 |
| 7,338,751 B2 | * | 3/2008 | Akahori | H05K 3/243 430/270.1 |
| 8,460,853 B2 | * | 6/2013 | Ajioka | C08F 2/50 430/270.1 |
| 2005/0238998 A1 | * | 10/2005 | Nakazato | G03F 7/027 430/281.1 |
| 2011/0111344 A1 | * | 5/2011 | Ajioka | G03F 7/027 430/281.1 |

(Continued)

FOREIGN PATENT DOCUMENTS

| | | |
|---|---|---|
| CN | 102289150 A | 12/2011 |
| CN | 102859438 A | 1/2013 |

(Continued)

OTHER PUBLICATIONS

Office Action dated May 28, 2019, from the Japanese Patent Office in counterpart Japanese application No. 2017-543565.
International Preliminary Report on Patentability with translation of Written Opinion dated Apr. 3, 2018, issued by the International Searching Authority in application No. PCT/JP2016/078839.
International Search Report dated Dec. 27, 2016, issued by the International Searching Authority in application No. PCT/JP2016/078839.

(Continued)

*Primary Examiner* — John S Chu
(74) *Attorney, Agent, or Firm* — Sughrue Mion, PLLC

(57) ABSTRACT

A composition for an electrode protective film of an electrostatic capacitance-type input device including (a) a binder polymer, (b) a photopolymerizable compound having an ethylenic unsaturated group, (c) a photopolymerization initiator, and (d) a compound capable of reacting with acidic groups or alcoholic hydroxy groups by heating, in which (b) the photopolymerizable compound having an ethylenic unsaturated group includes (b1) a photopolymerizable compound in which a value obtained by dividing a weight-average molecular weight by an average number of polymerizable groups is 270 or more can be used to form electrode protective films of electrostatic capacitance-type input devices having favorable bending resistance; an electrode protective film of an electrostatic capacitance-type input device; a transfer film; a laminate; an electrostatic capacitance-type input device; and an image display device.

41 Claims, 9 Drawing Sheets

(56) References Cited

U.S. PATENT DOCUMENTS

| | | | | |
|---|---|---|---|---|
| 2011/0151195 A1* | 6/2011 | Mitsukura | ............. | G03F 7/0388 428/156 |
| 2011/0262091 A1* | 10/2011 | Takasaki | ................ | G02B 6/122 385/129 |
| 2012/0181703 A1* | 7/2012 | Park | ........................ | C09J 133/06 257/774 |
| 2012/0319991 A1 | 12/2012 | Yang et al. | | |
| 2013/0302564 A1* | 11/2013 | Takihara | ............. | C08F 290/062 428/141 |
| 2014/0212809 A1* | 7/2014 | Park | ........................ | G03F 7/038 430/280.1 |
| 2014/0255846 A1* | 9/2014 | Ikeda | ................ | H01L 27/14618 430/281.1 |
| 2014/0314993 A1* | 10/2014 | Takihara | ............. | C08F 290/046 428/141 |
| 2014/0315036 A1 | 10/2014 | Kobayashi et al. | | |
| 2014/0377704 A1 | 12/2014 | Mukai et al. | | |
| 2015/0205202 A1* | 7/2015 | Jeong | ...................... | G03F 7/031 430/280.1 |
| 2016/0034081 A1 | 2/2016 | Ichiki | | |
| 2016/0357290 A1 | 12/2016 | Kanna | | |

FOREIGN PATENT DOCUMENTS

| | | |
|---|---|---|
| EP | 2 871 522 A1 | 5/2015 |
| JP | 2010-122361 A | 6/2010 |
| JP | 2010-160300 A | 7/2010 |
| JP | 2010-282001 A | 12/2010 |
| JP | 2013-004074 A | 1/2013 |
| JP | 2013-076821 A | 4/2013 |
| JP | 2013-100413 A | 5/2013 |
| JP | 2013-114008 A | 6/2013 |
| JP | 2013-195956 A | 9/2013 |
| JP | 2014-178922 A | 9/2014 |
| JP | 2014-206936 A | 10/2014 |
| JP | 2015-69585 A | 4/2015 |
| JP | 2013-037272 A | 2/2020 |
| WO | 2013/084884 | 6/2013 |
| WO | 2014/010345 A1 | 1/2014 |
| WO | 2015/125853 A1 | 8/2015 |

OTHER PUBLICATIONS

Written Opinion dated Dec. 27, 2016, issued by the International Searching Authority in application No. PCT/JP2016/078839.

Notification of Reasons for Revocation dated Jul. 6, 2020 in Japanese Patent No. 6581200.

Notice of Dispatch of Duplicates of a Written Opposition dated Apr. 17, 2020 in Japanese Patent No. 6581200.

Office Action dated Aug. 20, 2020 from the State Intellectual Property Office of the P.R.C. in Chinese Application No. 201680051296.7.

* cited by examiner

COMPOSITION FOR ELECTRODE PROTECTIVE FILM OF ELECTROSTATIC CAPACITANCE-TYPE INPUT DEVICE, ELECTRODE PROTECTIVE FILM OF ELECTROSTATIC CAPACITANCE-TYPE INPUT DEVICE, TRANSFER FILM, LAMINATE, ELECTROSTATIC CAPACITANCE-TYPE INPUT DEVICE, AND IMAGE DISPLAY DEVICE

CROSS-REFERENCE TO RELATED APPLICATIONS

This application is a Continuation of PCT International Application No. PCT/JP2016/078839, filed on Sep. 29, 2016, which claims priority under 35 U.S.C. Section 119(a) to Japanese Patent Application No. 2015-192459 filed on Sep. 30, 2015. Each of the above applications is hereby expressly incorporated by reference, in its entirety, into the present application.

BACKGROUND OF THE INVENTION

1. Field of the Invention

The present invention relates to a composition for an electrode protective film of an electrostatic capacitance-type input device, an electrode protective film of an electrostatic capacitance-type input device, a transfer film, a laminate, an electrostatic capacitance-type input device, and an image display device.

2. Description of the Related Art

Recently, as electronic devices such as mobile phones, car navigations, personal computers, ticket vending machines, and bank terminals, there have been electronic devices in which a liquid crystal display device having a touch panel-type input device is provided and desired commands can be input by contacting images and the like displayed on the liquid crystal display device with fingers or styluses.

As the input device (touch panel), there are resistance film-type input devices, electrostatic capacitance-type input devices, and the like. Electrostatic capacitance-type input devices have an advantage that a transparent conductive film needs to be formed only on one substrate. As such electrostatic capacitance-type input devices, for example, there are input devices in which electrode patterns are extended in mutually intersecting directions and input locations are detected by sensing changes in electrostatic capacitance between electrodes caused in a case in which an input surface of the electrostatic capacitance-type input device is contacted with fingers or the like.

As the electrode patterns, the use of fine wires of not only conductive and transparent metal oxides such as indium tin oxide (ITO) but also conductive metal such as silver is known (for example, refer to JP2014-206936A and JP2015-69585A).

For example, JP2014-206936A describes a method for manufacturing a conductive sheet for a touch panel, the method including "a step of forming a first detection electrode on a rear surface of a substrate and a rear surface-side wire having one end that is electrically connected to the first detection electrode and a first pad portion at the other end and forming a second detection electrode on a front surface of the substrate, a second lead-out wire electrically connected to the second detection electrode, and a second pad portion disposed at a location opposite to the first pad portion through the substrate", "a step of forming a through-hole that penetrates the first pad portion, the substrate, and the second pad portion", and "a step of producing a penetrating wire that electrically connects the first pad portion and the second pad portion by filling the through-hole with a conductive material and forming a first lead-out wire that includes the rear surface-side wire and the penetrating wire and is electrically connected to the first detection electrode". In addition, JP2014-206936A describes that the first detection electrode and the second detection electrode are constituted of a fine conductive wire or a conductive material that is included in the fine conductive wire is preferably silver since the conductivity of the fine conductive wire is excellent.

JP2015-69585A describes a laminate for a touch panel which is disposed on a viewer side of a display device, the laminate including a first transparent protective substrate, a conductive film having at least a first pressure-sensitive adhesive layer and a fine metal wire, a second pressure-sensitive adhesive layer, and a second transparent protective substrate in this order, in which, in a case in which the laminate is disposed on a display device, the second transparent protective substrate is located on a display device side, the second transparent protective substrate has at least one or more organic layers and one or more inorganic layers respectively, a moisture permeability of the second transparent protective substrate is 0.001 g/m$^2$·24 h (40° C., 90%) or less, and an amount of metal in the fine metal wire per unit area is 0.010 to 10 g/m$^2$.

SUMMARY OF THE INVENTION

Recently, regarding forms of image display devices having electrostatic capacitance-type input devices, instead of a stiff form of the related art, there has been a demand for a flexible (pliable) form that can be bent to a desired shape from the viewpoint of designability, portability, and wearability.

Compared with electrode patterns for which a brittle metal oxide such as ITO is used, the electrode pattern of JP2014-206936A or JP2015-69585A for which a fine wire of conductive metal is used is assumed to be strong to bending.

Meanwhile, there are cases in which an electrode protective film of an electrostatic capacitance-type input device which protects guidance wires (for example, metal wires such as copper wires) arranged in an electrode pattern and a frame portion of an electrostatic capacitance-type input device is provided on a side opposite to a surface on which commands are input with fingers or the like. From the viewpoint of enhancing a protection function, the use of a hard material has been assumed as the electrode protective film of an electrostatic capacitance-type input device.

For example, JP2014-206936A describes that a protective layer made of a binder may be further provided on a photosensitive layer or the provision of the protective layer prevents scratches or improves dynamic characteristics, but does not describe materials of the protective layer.

JP2015-69585A describes that the second pressure-sensitive adhesive layer and the second transparent protective substrate are provided on the side opposite to the surface of the conductive film having at least the fine metal wire on which commands are input with fingers or the like. JP2015-69585A describes the use of a polymer such as an acrylic pressure-sensitive adhesive material in the second pressure-sensitive adhesive layer. In addition, JP2015-69585A describes that the second transparent protective substrate has at least one or more organic layers and one or more inorganic layers respectively and the hardness of the organic layers is preferably high since it has been found that a high hardness of the organic layers enables the smooth formation of the inorganic layers and consequently the barrier performance improves.

As described above, at the moment, electrode protective films of electrostatic capacitance-type input devices having favorable bending resistance which can be used for flexible electrostatic capacitance-type input devices that can be bent in a desired shape have not yet known.

An object of the present invention is to provide a composition for an electrode protective film of an electrostatic capacitance-type input device which can be used to form electrode protective films of electrostatic capacitance-type input devices having favorable bending resistance.

In addition, another object of the present invention is to provide an electrode protective film of an electrostatic capacitance-type input device and a transfer film for which the composition for an electrode protective film of an electrostatic capacitance-type input device is used.

In addition, still another object of the present invention is to provide a laminate including the electrode protective film of an electrostatic capacitance-type input device having favorable bending resistance as a photosensitive resin layer, an electrostatic capacitance-type input device including the laminate, and an image display device including the electrostatic capacitance-type input device.

The present inventors found that, in a case where a photopolymerizable compound in which a value obtained by dividing a weight-average molecular weight by an average number of polymerizable groups is 270 or more and a compound capable of reacting with acidic groups or alcoholic hydroxy groups by heating are jointly used, it is possible to form an electrode protective film of an electrostatic capacitance-type input device having favorable bending resistance and completed the present invention.

The present invention and preferred aspects of the present invention which are specific means for achieving the above-described objects are as described below.

[1] A composition for an electrode protective film of an electrostatic capacitance-type input device comprising: (a) a binder polymer; (b) a photopolymerizable compound having an ethylenic unsaturated group; (c) a photopolymerization initiator; and (d) a compound capable of reacting with acidic groups or alcoholic hydroxy groups by heating, in which (b) the photopolymerizable compound having an ethylenic unsaturated group includes (b1) a photopolymerizable compound in which a value obtained by dividing a weight-average molecular weight by an average number of polymerizable groups is 270 or more.

[2] The composition for an electrode protective film of an electrostatic capacitance-type input device according to [1], in which, in an electrode protective film of an electrostatic capacitance-type input device obtained by curing the composition for an electrode protective film of an electrostatic capacitance-type input device, a breaking elongation is preferably 5% or more in a tensile test under an environment of 23° C. and a relative humidity of 50%.

[3] The composition for an electrode protective film of an electrostatic capacitance-type input device according to [1] or [2], in which (b) the photopolymerizable compound having an ethylenic unsaturated group preferably includes (b1-1) a photopolymerizable compound in which a value obtained by dividing a weight-average molecular weight by an average number of polymerizable groups is 350 or more.

[4] The composition for an electrode protective film of an electrostatic capacitance-type input device according to any one of [1] to [3], in which, in the composition for an electrode protective film of an electrostatic capacitance-type input device, a ratio of (b1) the photopolymerizable compound in which a value obtained by dividing a weight-average molecular weight by an average number of polymerizable groups is 270 or more to all of (b) the photopolymerizable compound having an ethylenic unsaturated group is preferably 10% by mass or more.

[5] The composition for an electrode protective film of an electrostatic capacitance-type input device according to any one of [1] to [4], in which, in the composition for an electrode protective film of an electrostatic capacitance-type input device, a ratio of (b1) the photopolymerizable compound in which a value obtained by dividing a weight-average molecular weight by an average number of polymerizable groups is 270 or more to a total solid content is preferably 5% by mass or more.

[6] The composition for an electrode protective film of an electrostatic capacitance-type input device according to any one of [1] to [5], in which (d) the compound capable of reacting with acidic groups or alcoholic hydroxy groups by heating is preferably a blocked isocyanate.

[7] The composition for an electrode protective film of an electrostatic capacitance-type input device according to any one of [1] to [6], in which (d) the compound capable of reacting with acidic groups or alcoholic hydroxy groups by heating is preferably a compound having a structure represented by General Formula (1);

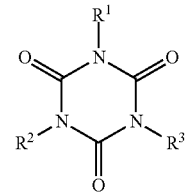

General Formula (1)

in General Formula (1), $R^1$ to $R^3$ each independently represent a monovalent organic group.

[8] An electrode protective film of an electrostatic capacitance-type input device formed of the composition for an electrode protective film of an electrostatic capacitance-type input device according to any one of [1] to [7].

[9] A transfer film comprising: a temporary support; and a photosensitive resin layer including the composition for an electrode protective film of an electrostatic capacitance-type input device according to any one of [1] to [7].

[10] An electrode protective film of an electrostatic capacitance-type input device obtained by removing the temporary support from the transfer film according to [9].

[11] A laminate comprising: an electrode protective film of an electrostatic capacitance-type input device formed by transferring the electrode protective film of an electrostatic capacitance-type input device according to [8] or [10] or the photosensitive resin layer in the transfer film according to [9] onto a substrate including an electrode of an electrostatic capacitance-type input device.

[12] A laminate comprising: a substrate including an electrode of an electrostatic capacitance-type input device; and a photosensitive resin layer located on the substrate, in which the photosensitive resin layer includes (a) a binder polymer, (b) a photopolymerizable compound having an ethylenic unsaturated group, (c) a photopolymerization initiator, and (d) a compound capable of reacting with acidic groups or alcoholic hydroxy groups by heating, and (b) the photopolymerizable compound having an ethylenic unsaturated group includes (b1) a photopolymerizable compound in which a value obtained by dividing a weight-average molecular weight by an average number of polymerizable groups is 270 or more.

[13] The laminate according to [11] or [12], in which the electrode of an electrostatic capacitance-type input device preferably includes at least at least one kind of metal selected from Au, Ag, Cu, and Al or an alloy including at least one kind of metal selected from Au, Ag, Cu, and Al.

[14] The laminate according to any one of [11] to [13], in which the photosensitive resin layer is preferably cured.

[15] An electrostatic capacitance-type input device comprising: the laminate according to any one of [11] to [14].

[16] An image display device comprising: the electrostatic capacitance-type input device according to [15].

According to the present invention, it is possible to provide a composition for an electrode protective film of an electrostatic capacitance-type input device which can be used to form electrode protective films of electrostatic capacitance-type input devices having favorable bending resistance.

In addition, according to the present invention, it is possible to provide an electrode protective film of an electrostatic capacitance-type input device and a transfer film for which the composition for an electrode protective film of an electrostatic capacitance-type input device is used.

In addition, according to the present invention, it is possible to provide a laminate including the electrode protective film of an electrostatic capacitance-type input device having favorable bending resistance as a photosensitive resin layer, an electrostatic capacitance-type input device including the laminate, and an image display device including the electrostatic capacitance-type input device.

BRIEF DESCRIPTION OF THE DRAWINGS

FIG. 14 is a schematic view illustrating an example of a state in which the transfer film of the present invention having a photosensitive resin layer is laminated on the electrode pattern in the electrostatic capacitance-type input device by means of lamination and is yet to be cured by means of exposure or the like.

DESCRIPTION OF THE PREFERRED EMBODIMENTS

Figure 1:
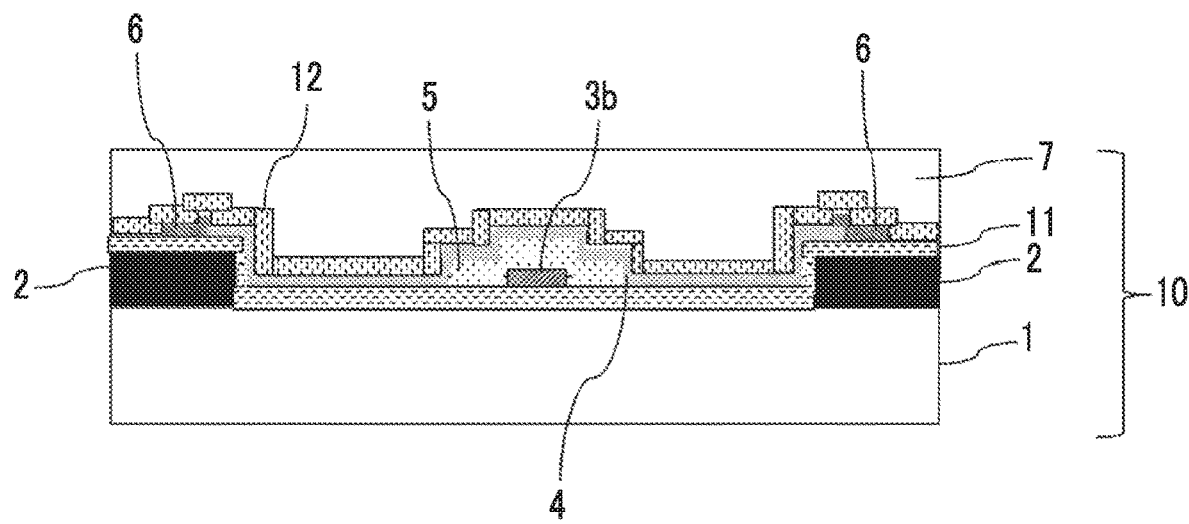
FIG. 1 is a schematic cross-sectional view illustrating an example of a constitution of an electrostatic capacitance-type input device of the present invention.

Hereinafter, a composition for an electrode protective film of an electrostatic capacitance-type input device, an electrode protective film of an electrostatic capacitance-type input device, a transfer film, a laminate, an electrostatic capacitance-type input device, and an image display device of the present invention will be described. Hereinafter, there are cases in which constituent requirements will be described on the basis of typical embodiments or specific examples of the present invention, but the present invention is not limited to the embodiments or the specific examples. Meanwhile, in the present specification, numerical ranges expressed using "to" include numerical values before and after "to" as the lower limit value and the upper limit value. "(Meth)acryl" refers to both "methacryl" and "acryl", which is also true in other "(meth)" cases.

Unless particularly otherwise described, refractive indexes in the present specification refer to refractive indexes at a wavelength of 550 nm.

Meanwhile, being transparent in the present specification means that the average transmittance of visible light having a wavelength of 400 nm to 700 nm is 80% or more. Therefore, transparent layers refer to layers having an average transmittance of visible light having a wavelength of 400 nm to 700 nm of 80% or more. The average transmittance of visible light having a wavelength of 400 nm to 700 nm of a transparent layer is preferably 90% or more.

The average transmittance of visible light having a wavelength of 400 nm to 700 nm of the transfer film of the present invention or transparent layers in the transfer film is measured using a spectrophotometer U-3310 manufactured by Hitachi, Ltd.

[Composition for Electrode Protective Film of Electrostatic Capacitance-Type Input Device]

A composition for an electrode protective film of an electrostatic capacitance-type input device of the present invention is a composition for an electrode protective film of an electrostatic capacitance-type input device including (a) a binder polymer, (b) a photopolymerizable compound having an ethylenic unsaturated group, (c) a photopolymerization initiator, and (d) a compound capable of reacting with acidic groups or alcoholic hydroxy groups by heating, in which (b) the photopolymerizable compound having an ethylenic unsaturated group includes (b1) a photopolymerizable compound in which a value obtained by dividing a weight-average molecular weight by an average number of polymerizable groups is 270 or more.

Due to this constitution, the composition for an electrode protective film of an electrostatic capacitance-type input device of the present invention can be used to form electrode protective films of electrostatic capacitance-type input devices which have favorable bending resistance.

For electrode protective films of electrostatic capacitance-type input devices of the related art, it has been common to increase the density of ethylenic unsaturated groups and cure the films to be hard so as not to bend. In contrast, in the present invention, it is possible to form electrode protective films of electrostatic capacitance-type input devices which are cured to an appropriate extent so as to be appropriately hard and have favorable bending resistance (so that appearance abnormality such as cracking or whitening does not easily occur even in a case in which the cured electrode protective films are bent) using (b1) the photopolymerizable compound in which a value obtained by dividing a weight-average molecular weight by an average number of polymerizable groups is 270 or more. Although not confined to any theories, in (b1) the photopolymerizable compound in which a value obtained by dividing a weight-average molecular weight by an average number of polymerizable groups is 270 or more, it is assumed that the distance between ethylenic unsaturated groups becomes relatively longer than that of photopolymerizable compounds that are used in the related art. Therefore, in films formed by curing the composition of an electrode protective film of an electrostatic capacitance-type input device of the present invention, it is assumed that the density of ethylenic unsaturated groups in the films or the crosslinking density of (d) the compound capable of reacting with acidic groups or alcoholic hydroxy groups by heating is suppressed. As a result, it is assumed that electrode protective films of electrostatic capacitance-type input devices having favorable bending resistance can be formed.

Hereinafter, a preferred aspect of the composition for an electrode protective film of an electrostatic capacitance-type input device of the present invention will be described.

<Characteristics>

In the present invention, in an electrode protective film of an electrostatic capacitance-type input device obtained by curing the composition for an electrode protective film of an electrostatic capacitance-type input device, in a tensile test under an environment of 23° C. and a relative humidity of 50%, a breaking elongation is preferably 4.8% or more from the viewpoint of bending resistance, the breaking elongation is more preferably 5% or more, and the breaking elongation is more preferably 5.1% or more.

<Composition>

The composition for an electrode protective film of an electrostatic capacitance-type input device of the present invention may be a negative-type material or a positive-type material and is preferably a negative-type material. That is, an electrode protective film of an electrostatic capacitance-type input device of the present invention may be a negative-type material or a positive-type material and is preferably a negative-type material.

A preferred composition of the composition for an electrode protective film of an electrostatic capacitance-type input device of the present invention will be described.

((a) Binder Polymer)

The composition for an electrode protective film of an electrostatic capacitance-type input device of the present invention includes (a) a binder polymer.

The binder polymer is not particularly limited.

The binder polymer is preferably an acrylic resin.

A preferred range of the binder polymer that is used in the composition for an electrode protective film of an electrostatic capacitance-type input device will be specifically described.

The binder polymer is preferably an alkali-soluble resin, more preferably a resin having a polar group, and particularly preferably a resin having an acidic group. It is assumed that, in a case in which (d) the compound capable of reacting with acidic groups or alcoholic hydroxy groups by heating is added to a resin having an acidic group so as to form thermal crosslinking, the three-dimensional crosslinking density increases, which contributes to the improvement of functions as a protective film such as the heat and moisture resistance after the supply of saline water.

In a case in which the binder polymer is a resin having an acidic group, the acid value of the binder polymer is not particularly limited.

The binder polymer that is a resin having an acidic group, which is used in the composition for an electrode protective film of an electrostatic capacitance-type input device (also referred to as "binder" or "polymer"), is not particularly limited within the scope of the gist of the present invention and can be appropriately selected from well-known binder polymers. The polymers described in Paragraph 0025 of JP2011-95716A and the polymers described in Paragraphs 0033 to 0052 of JP2010-237589A are preferably used.

The composition for an electrode protective film of an electrostatic capacitance-type input device may also include a binder polymer formed of a polymer latex as the binder polymer. The polymer latex mentioned herein is a latex obtained by dispersing the particles of a water-insoluble polymer in water. The polymer latex is described in, for example, "Chemistry of high-molecular-weight latex (published by Kobunshi Kankokai (1973))" by Muroi Soichi.

Polymer particles that can be used are preferably polymer particles of a polymer such as an acrylic polymer, a vinyl acetate-based polymer, a rubber-based (for example, styrene-butadiene-based or chloroprene-based) polymer, an olefin-based polymer, a polyester-based polymer, a polyurethane-based polymer, a polystyrene-based polymer or a copolymer thereof.

The binder polymer formed of a polymer latex preferably strengthens the bonding forces between polymer chains constituting the polymer particles. Examples of means for strengthening the bonding forces between polymer chains include means of using interactions attributed to hydrogen bonds and means of generating covalent bonds.

Means of using interactions attributed to hydrogen bonding forces is preferably the introduction of monomers having a polar group into polymer chains by means of copolymerization or graft polymerization.

Examples of the polar group (preferably the acidic group) in the binder polymer include carboxyl groups (included in acrylic acid, methacrylic acid, itaconic acid, fumaric acid, maleic acid, crotonic acid, partially-esterified maleic acid, and the like), primary, secondary, and tertiary amino groups, ammonium salt groups, sulfonic acid groups (styrenesulfonic acid groups and the like), and the like. The binder polymer preferably has at least a carboxyl group as the polar group. In a case in which the binder polymer is a resin having an acidic group, the binder polymer is preferably a carboxyl group-containing resin. It is assumed that, in a case in which (d) the compound capable of reacting with acidic groups or alcoholic hydroxy groups by heating (a blocked isocyanate or the like) is added to a carboxyl group-containing resin so as to form thermal crosslinking, the three-dimensional crosslinking density increases, the carboxyl group in the carboxyl group-containing resin loses water and is hydrophobilized, or the like, which contributes to the improvement of functions as a protective film such as the heat and moisture resistance after the supply of saline water.

The binder polymer is more preferably a carboxyl group-containing acrylic resin.

The composition for an electrode protective film of an electrostatic capacitance-type input device may also include an additional binder polymer other than the carboxyl group-containing acrylic resin.

As the additional binder polymer included in the composition for an electrode protective film of an electrostatic capacitance-type input device, an arbitrary polymer component can be used without any particularly limitations; however, from the viewpoint of being used as a transparent protective film of an electrostatic capacitance-type input device, a polymer component having high thermal resistance is preferred, and an alkali-soluble resin is more preferred.

In the binder polymer, a preferred range of the copolymerization ratio of a constitutional unit derived from the above-described monomer having a polar group is in a range of 5% to 50% by mass, more preferably 5% to 40% by mass, and particularly preferably 20% to 30% by mass with respect to 100% by mass of the binder polymer.

Examples of means of generating covalent bonds include methods in which at least one kind of an epoxy compound, a blocked isocyanate, an isocyanate, a vinylsulfone compound, an aldehyde compound, a methylol compound, a carboxylic acid anhydride, and the like is reacted with at least one kind of a hydroxyl group, a carboxyl group, a primary or secondary amino group, an acetoacetyl group, a sulfonic acid group, and the like.

The polymer latex that can be used in the present invention may be a polymer latex obtained by emulsification polymerization or a polymer latex obtained by emulsification. Methods for preparing the polymer latex are described in, for example, "Emulsion Latex Handbook" (edited by the emulsion latex handbook editorial committee, published by Taiseisha Ltd. (1975)).

Examples of the polymer latex that can be used in the present invention include polymer latexes obtained by ammonia-neutralizing and emulsifying alkyl acrylate copolymer-ammonium (trade name: JURYMER AT-210, manufactured by Toagosei Co., Ltd.), alkyl acrylate copolymer-ammonium (trade name: JURYMER ET-410, manufactured by Toagosei Co., Ltd.), alkyl acrylate copolymer-ammonium (trade name: JURYMER AT-510, manufactured by Toagosei Co., Ltd.), or polyacrylic acid (trade name: JURYMER AC-10L, manufactured by Toagosei Co., Ltd.).

The alkali-soluble resin can be appropriately selected from alkali-soluble resins which are linear organic macromolecular polymers and have at least one group that accelerates alkali dissolution (that is, an acidic group: for example, a carboxyl group, a phosphoric acid group, a sulfonic acid group, or the like) in a molecule (preferably a molecule having an acrylic copolymer or a styrene-based copolymer as the main chain). Among these, alkali-soluble resins which are soluble in organic solvents and can be developed using a weak alkaline aqueous solution are more preferred. The acidic group is preferably a carboxyl group.

To the manufacturing of the alkali-soluble resin, it is possible to apply, for example, a method in which a well-known radical polymerization method is used. The polymerization conditions such as temperature, pressure, the kind and amount of radical initiators, and the kind of solvents in the case of manufacturing the alkali-soluble resin using a radical polymerization method can be easily set by persons skilled in the art, and the conditions can also be experimentally determined.

The linear organic macromolecular polymer is preferably a polymer having a carboxylic acid in a side chain. Preferred examples thereof include poly(meth)acrylates, methacrylic acid copolymers, acrylic acid copolymers, itaconic acid copolymers, crotonic acid copolymers, maleic acid copolymers such as styrene/maleic acid, partially-esterified maleic acid copolymers, acidic cellulose derivatives having a carboxylic acid in a side chain such as carboxyalkyl cellulose and carboxyalkyl starch, polymers obtained by adding an acid anhydride to a polymer having a hydroxyl group, and macromolecular polymers having a reactive functional group such as a (meth)acryloyl group in a side chain which are respectively described in JP1984-44615A (JP-S59-44615A), JP1979-34327B (JP-S54-34327B), JP1983-12577B (JP-S58-12577B), JP1979-25957B (JP-S54-25957B), JP1984-53836A (JP-S59-53836A), JP1984-71048A (JP-S59-71048A), JP1971-2121A (JP-S46-2121A), and JP1981-40824B (JP-S56-40824B).

Among these, particularly, benzyl (meth)acrylate/(meth)acrylic acid copolymers or multicomponent copolymers made of benzyl (meth)acrylate/(meth)acrylic acid/other monomers are preferred.

Additionally, polymers obtained by copolymerizing 2-hydroxyethylmethacrylate are also useful. The amount of the polymer being mixed and used can be arbitrary.

Additionally, examples thereof include 2-hydroxypropyl (meth)acrylate/polystyrene macromonomer/benzyl methacrylate/methacrylic acid copolymers, 2-hydroxy-3-phenoxypropyl acrylate/polymethyl methacrylate macromonomer/benzyl methacrylate/methacrylic acid copolymers, 2-hydroxyethyl methacrylate/polystyrene macromonomer/methyl methacrylate/methacrylic acid copolymers, 2-hydroxyethyl methacrylate/polystyrene macromonomer/benzyl methacrylate/methacrylic acid copolymers, and the like which are described in JP1995-140654A (JP-H07-140654A).

Regarding the specific constitutional unit of the alkali-soluble resin, particularly, copolymers of (meth)acrylic acid and an additional monomer capable of being copolymerized with (meth)acrylic acid are preferred.

Examples of the additional monomer capable of being copolymerized with (meth)acrylic acid include alkyl (meth)acrylates, aryl (meth)acrylates, vinyl compounds, and the like. Here, hydrogen atoms in alkyl groups and aryl groups may be substituted with substituents.

Specific examples of alkyl (meth)acrylate and aryl (meth) acrylate include methyl (meth)acrylates, ethyl (meth)acrylates, propyl (meth)acrylates, butyl (meth)acrylates, isobutyl (meth)acrylates, pentyl (meth)acrylates, hexyl (meth)acrylates, octyl (meth)acrylates, phenyl (meth)acrylates, benzyl acrylates, tolyl acrylates, naphthyl acrylates, cyclohexyl acrylates, and the like.

In addition, examples of the vinyl compounds include styrene, α-methyl styrene, vinyl toluene, glycidyl methacrylate, acrylonitrile, vinyl acetate, N-vinyl pyrrolidone, tetrahydrofurfuryl methacrylate, polystyrene macromonomers, polymethyl methacrylate macromonomers, $CH_2=CR^1R^2$, $CH_2=C(R^1)(COOR^3)$ [here, $R^1$ represents a hydrogen atom or an alkyl group having 1 to 5 carbon atoms, $R^2$ represents an aromatic hydrocarbon ring having 6 to 10 carbon atoms, and $R^3$ represents an alkyl group having 1 to 8 carbon atoms or an aralkyl group having 6 to 12 carbon atoms], and the like.

Only one kind of the additional monomer capable of being copolymerized with (meth)acrylic acid can be used singly or a combination of two or more kinds of monomers capable of being copolymerized with (meth)acrylic acid can be used. A preferred additional monomer capable of being copolymerized with (meth)acrylic acid is at least one kind of monomer selected from $CH_2=CR^1R^2$, $CH_2=C(R^1)(COOR^3)$, phenyl (meth)acrylates, benzyl (meth)acrylates, and styrene and particularly preferably $CH_2=CR^1R^2$ and/or $CH_2=C(R^1)(COOR^3)$.

Additionally, examples thereof include resins having an ethylenic unsaturated double bond introduced into a linear macromolecule which are obtained by reacting a (meth) acrylic compound having a reactive functional group, cinnamic acid, or the like with the linear macromolecule having a substituent capable of reacting with this reactive functional group. Examples of the reactive functional group include a hydroxyl group, a carboxyl group, an amino group, and the like, and examples of the substituent capable of being reacted with this reactive functional group include an isocyanate group, an aldehyde group, an epoxy group, and the like.

Among these, the alkali-soluble resin is preferably an acrylic resin having an acidic group, preferably a copolymer resin of (meth)acrylic acid/vinyl compound, and particularly preferably a copolymer resin of (meth)acrylic acid/allyl (meth)acrylate. Meanwhile, in the present specification, acrylic resins refer to both methacrylic resins and acrylic resins, and, similarly, (meth)acrylic resins refer to methacrylic resins and acrylic resins.

The weight-average molecular weight of the binder polymer is preferably 10,000 or more and more preferably 20,000 to 100,000.

((b) Photopolymerizable Compound Having Ethylenic Unsaturated Group)

The composition for an electrode protective film of an electrostatic capacitance-type input device of the present invention includes (b) a photopolymerizable compound having an ethylenic unsaturated group, and (b) the photopolymerizable compound having an ethylenic unsaturated group includes (b1) a photopolymerizable compound in which a value obtained by dividing the weight-average molecular weight by the average number of polymerizable groups is 270 or more.

(b) The photopolymerizable compound having an ethylenic unsaturated group may have at least one ethylenic unsaturated group as a polymerizable group and may have an additional polymerizable group such as an epoxy group in addition to the ethylenic unsaturated group. The polymerizable group is preferably a polymerizable group capable of radical polymerization or cationic polymerization, and examples thereof include a vinyl group, an allyl group, an acryloyl group, a methacryloyl group, an epoxy group, a dioxetane group, a cyano group, an isocyanate group, and the like. (b) The photopolymerizable compound having an ethylenic unsaturated group preferably includes a compound having a (meth)acryloyl group.

Only one kind of (b) the photopolymerizable compound having an ethylenic unsaturated group may be used, and two or more kinds thereof may be used in combination, but a combined use of two or more kinds of the photopolymerizable compounds is preferred.

In the composition for an electrode protective film of an electrostatic capacitance-type input device of the present invention, (b) the photopolymerizable compound having an ethylenic unsaturated group includes (b1) a photopolymerizable compound in which a value obtained by dividing the weight-average molecular weight by the average number of polymerizable groups (preferably ethylenic unsaturated groups) is 270 or more.

In the present specification, as the weight-average molecular weight of (b) the photopolymerizable compound having an ethylenic unsaturated group, a polystyrene-equivalent value obtained using gel permeation chromatography (GPC) is used.

In the present specification, regarding the average number of the polymerizable groups in (b) the photopolymerizable compound having an ethylenic unsaturated group, impurities having a content of 10% by mass or less in the solid content are not taken into account, and, in a case in which the compound is a mixture, an average value corresponding to the content ratio is employed.

In the composition for an electrode protective film of an electrostatic capacitance-type input device of the present invention, the ratio of (b1) the photopolymerizable compound in which a value obtained by dividing the weight-average molecular weight by the average number of polymerizable groups is 270 or more to all of (b) the photopolymerizable compound having an ethylenic unsaturated group in the composition for an electrode protective film of an electrostatic capacitance-type input device is preferably 10% by mass or more from the viewpoint of improving the bending resistance, more preferably 15% by mass or more, and particularly preferably 20% by mass or more. In the composition for an electrode protective film of an electrostatic capacitance-type input device of the present invention, the ratio of (b1) the photopolymerizable compound in which a value obtained by dividing the weight-average molecular weight by the average number of polymerizable groups is 270 or more to all of (b) the photopolymerizable compound having an ethylenic unsaturated group in the composition for an electrode protective film of an electrostatic capacitance-type input device may be 100% by mass or more, but is preferably 80% by mass or less, more preferably 60% by mass or less, and particularly preferably 50% by mass or less.

In the composition for an electrode protective film of an electrostatic capacitance-type input device of the present invention, the ratio of (b1) the photopolymerizable compound in which a value obtained by dividing the weight-average molecular weight by the average number of polymerizable groups is 270 or more to the total solid content in the composition for an electrode protective film of an electrostatic capacitance-type input device is preferably 5% by mass or more from the viewpoint of improving the bending resistance, more preferably 6% by mass or more, and particularly preferably 7% by mass or more. In the composition for an electrode protective film of an electrostatic capacitance-type input device of the present invention, the ratio of (b1) the photopolymerizable compound in which a value obtained by dividing the weight-average molecular weight by the average number of polymerizable groups is 270 or more to the total solid content in the composition for an electrode protective film of an electrostatic capacitance-type input device is preferably 80% by mass or less, more preferably 50% by mass or less, and particularly preferably 30% by mass or less.

In the composition for an electrode protective film of an electrostatic capacitance-type input device of the present invention, (b) the photopolymerizable compound having an ethylenic unsaturated group preferably includes (b1-1) a photopolymerizable compound in which a value obtained by dividing the weight-average molecular weight by the average number of polymerizable groups is 350 or more and more preferably includes (b1-2) a photopolymerizable compound in which a value obtained by dividing the weight-average molecular weight by the average number of polymerizable groups is 350 to 3,000. In the composition for an electrode protective film of an electrostatic capacitance-type input device of the present invention, a preferred ratio between (b1-1) the photopolymerizable compound in which a value obtained by dividing the weight-average molecular weight by the average number of polymerizable groups is 350 or more and (b1-2) the photopolymerizable compound in which a value obtained by dividing the weight-average molecular weight by the average number of polymerizable groups is 350 to 3,000 is the same as the preferred ratio of (b1) the photopolymerizable compound in which a value obtained by dividing the weight-average molecular weight by the average number of polymerizable groups is 270 or more.

As (b1) the photopolymerizable compound in which a value obtained by dividing the weight-average molecular weight by the average number of polymerizable groups is 270 or more which can be used in the composition for an electrode protective film of an electrostatic capacitance-type input device of the present invention, commercially available products can be used. Examples thereof include A-BPEF (manufactured by Shin-Nakamura Chemical Co., Ltd.), A-600 (manufactured by Shin-Nakamura Chemical Co., Ltd.), UF-8001G (manufactured by Kyoeisha Chemical Co., Ltd.), UA-160TM (manufactured by Shin-Nakamura Chemical Co., Ltd.), UA-122P (manufactured by Shin-Nakamura Chemical Co., Ltd.), and the like.

As (b) the photopolymerizable compound having an ethylenic unsaturated group, a tri- or higher-functional photopolymerizable compound and a difunctional photopolymerizable compound are preferably used in combination. The content of the difunctional photopolymerizable compound being used is preferably in a range of 10% to 90% by mass of all of the photopolymerizable compounds, more preferably 20% to 85% by mass, and particularly preferably 30% to 80% by mass. The content of the tri- or higher-functional photopolymerizable compound being used is preferably in a range of 10% to 90% by mass of all of the photopolymerizable compounds, more preferably 15% to 80% by mass, and particularly preferably 20% to 70% by mass. The composition for an electrode protective film of an electrostatic capacitance-type input device preferably includes, as (b) the photopolymerizable compound having an ethylenic unsaturated group, at least a compound having at least two ethylenic unsaturated groups and a compound having at least three ethylenic unsaturated groups and more preferably includes at least a compound having two (meth)acryloyl groups and a compound having at least three (meth)acryloyl groups.

In addition, in the composition for an electrode protective film of an electrostatic capacitance-type input device, at least one kind of (b) the photopolymerizable compound having an ethylenic unsaturated group preferably contains a carboxyl group since the carboxyl group in (a) the binder polymer and the carboxyl group in (b) the photopolymerizable compound having an ethylenic unsaturated group form a carboxylic acid anhydride and thus further enhance the heat and moisture resistance after the supply of saline water. A photopolymerizable compound having an ethylenic unsaturated group containing a carboxyl group is not particularly limited, and commercially available compounds can be used. For example, ARONIX TO-2349 (manufactured by Toagosei Co., Ltd.), ARONIX M-520 (manufactured by Toagosei Co., Ltd.), ARONIX M-510 (manufactured by Toagosei Co., Ltd.), and the like can be preferably used. The content of the photopolymerizable compound having an ethylenic unsaturated group containing a carboxyl group being used is preferably in a range of 1% to 50% by mass, more preferably in a range of 1% to 30% by mass, and particularly preferably in a range of 1% to 15% by mass of all of the photopolymerizable compounds.

The composition preferably includes, as (b) the photopolymerizable compound having an ethylenic unsaturated group, an urethane (meth)acrylate compound. The amount of the urethane (meth)acrylate compound mixed is preferably 10% by mass or more and more preferably 20% by mass or more of all of the photopolymerizable compounds. In the urethane (meth)acrylate compound, the number of functional groups in the photopolymerizable groups, that is, the number of (meth)acryloyl groups is preferably three or more and more preferably four or more.

Photopolymerizable compounds having a difunctional ethylenic unsaturated group are not particularly limited as long as the compounds have two ethylenic unsaturated groups in the molecule, and commercially available (meth)acrylate compounds can be used. For example, it is possible to preferably use tricyclodecane dimethanol diacrylate (A-DCP, manufactured by Shin-Nakamura Chemical Co., Ltd.), tricyclodecane dimethanol dimethacrylate (DCP, manufactured by Shin-Nakamura Chemical Co., Ltd.), 1,9-nonanediol diacrylate (A-NOD-N, manufactured by Shin-Nakamura Chemical Co., Ltd.), 1,6-hexanediol diacrylate (A-HD-N, manufactured by Shin-Nakamura Chemical Co., Ltd.), and the like.

Photopolymerizable compounds having a tri- or higher-functional ethylenic unsaturated group is not particularly limited as long as the compounds have three or more ethylenic unsaturated groups in the molecule, and, for example, it is possible to use (meth)acrylate compounds having a skeleton such as dipentaerythritol (tri/tetra/penta/hexa)acrylates, pentaerythritol (tri/tetra)acrylates, trimethylolpropane triacrylate, ditrimethylolpropane tetraacrylate (AD-TMP manufactured by Shin-Nakamura Chemical Co., Ltd.), or isocyanurate acrylate, and (meth)acrylate compounds having a long distance between (meth)acryloyl groups are preferred. Specifically, it is possible to preferably use caprolactone-modified compounds (KAYARAD DPCA manufactured by Nippon Kayaku Co., Ltd., A-9300-1CL manufactured by Shin-Nakamura Chemical Co., Ltd., and the like), alkylene oxide-modified compounds (KAYARAD RP-1040 manufactured by Nippon Kayaku Co., Ltd., ATM-35E and A-9300 manufactured by Shin-Nakamura Chemical Co., Ltd., EBECRYL 135), and the like of the above-described (meth)acrylate compounds having a skeleton such as dipentaerythritol (tri/tetra/penta/hexa)acrylates, pentaerythritol (tri/tetra)acrylates, trimethylolpropane triacrylate, ditrimethylolpropane tetraacrylate, and isocyanurate acrylate. In addition, it is preferable to use tri- or higher-functional urethane (meth)acrylates. As the tri- or higher-functional urethane (meth)acrylates, it is possible to preferably use 8UX-015A (manufactured by Taisei Fine Chemical Co., Ltd.), UA-32P (manufactured by Shin-Nakamura Chemical Co., Ltd.), UA-1100H (manufactured by Shin-Nakamura Chemical Co., Ltd.,), and the like.

The weight-average molecular weight of (b) the photopolymerizable compound having an ethylenic unsaturated group is preferably 80 to 10,000, more preferably 90 to 3,000, and particularly preferably 95 to 2,500.

((c) Photopolymerization Initiator)

The composition for an electrode protective film of an electrostatic capacitance-type input device of the present invention includes (c) a photopolymerization initiator. In a case in which the composition for an electrode protective film of an electrostatic capacitance-type input device includes (b) the photopolymerizable compound having an ethylenic unsaturated group and (c) the photopolymerization initiator, it is possible to facilitate the formation of patterns of the composition for an electrode protective film of an electrostatic capacitance-type input device.

As the photopolymerization initiator that is used in the composition for an electrode protective film of an electrostatic capacitance-type input device, it is possible to use the photopolymerization initiators described in Paragraphs "0031" to "0042" of JP2011-95716A. For example, it is possible to preferably use 1,2-octane dione, 1-[4-(phenylthio)-, 2-(O-benzoyloxime)] (trade name: IRGACURE OXE-01, manufactured by BASF), additionally, ethanone, 1-[9-ethyl-6-(2-methylbenzoyl)-9H-carbazole-3-yl]-, 1-(O-acetyloxime) (trade name: IRGACURE OXE-02, manufactured by BASF), 2-(dimethylamino)-2-[(4-methylphenyl) methyl]-1-[4-(4-morpholinyl)phenyl]-1-butanone (trade name: IRGACURE 379EG, manufactured by BASF), 2-methyl-1-(4-methyl thiophenyl)-2-morpholino propan-1-one (trade name: IRGACURE 907, manufactured by BASF), 2-hydroxy-1-{4-[4-(2-hydroxy-2-methyl-propionyl)-benzyl]phenyl}-2-methyl-propan-1-one (trade name: IRGACURE 127, manufactured by BASF), 2-benzyl-2-dimethylamino-1-(4-morpholinophenyl)-butanone-1 (trade name: IRGACURE 369, manufactured by BASF), 2-hydroxy-2-methyl-1-phenyl-erypropan-1-one (trade name: IRGACURE 1173, manufactured by BASF), 1-hydroxy-cyclohexyl-phenyl-ketone (trade name: IRGACURE 184, manufactured by BASF), 2,2-dimethoxy-1,2-diphenyl ethane-1-one (trade name: IRGACURE 651, manufactured by BASF), oxime ester-based photopolymerization initiator (trade name: Lunar 6, manufactured by DKSH Japan K.K.), and the like.

The content of (c) the photopolymerization initiator in the composition for an electrode protective film of an electrostatic capacitance-type input device is preferably 1% by mass or more and more preferably 2% by mass or more of the photosensitive transparent resin layer. The content of (c) the photopolymerization initiator is preferably 10% by mass or less and more preferably 5% by mass or less of the composition for an electrode protective film of an electrostatic capacitance-type input device from the viewpoint of improving the patterning property of a laminate of the present invention.

((d) Compound Capable of Reacting with Acidic Groups or Alcoholic Hydroxy Groups by Heating)

The composition for an electrode protective film of an electrostatic capacitance-type input device of the present invention includes (d) a compound capable of reacting with acidic groups or alcoholic hydroxy groups by heating.

(d) The compound capable of reacting with acidic groups or alcoholic hydroxy groups by heating is not particularly limited within the scope of the gist of the present invention. (d) The compound capable of reacting with acidic groups or alcoholic hydroxy groups by heating is preferably a compound having a higher reactivity with acidic groups or alcoholic hydroxy groups after being heated to higher than 25° C. compared with the reactivity with acidic groups or alcoholic hydroxy groups at 25° C. (d) The compound capable of reacting with acidic groups or alcoholic hydroxy groups by heating is preferably a compound which is temporarily inactivated by a thermally dissociable blocking agent and in which thermally dissociable blocking agent-derived groups are dissociated at a predetermined dissociation temperature by heating.

Examples of (d) the compound capable of reacting with acidic groups or alcoholic hydroxy groups by heating include blocked isocyanates and epoxy compounds. In the composition for an electrode protective film of an electrostatic capacitance-type input device of the present invention, (d) the compound capable of reacting with acidic groups or alcoholic hydroxy groups by heating is preferably a blocked isocyanate.

—(d1) Blocked Isocyanate—

A blocked isocyanate refers to "a compound having a structure in which isocyanate groups in an isocyanate are protected (also referred to as 'masked' or 'blocked') with a thermally dissociable blocking agent".

The blocked isocyanate is preferably a compound having a structure in which isocyanate groups in a polyisocyanate are protected (masked) with a thermally dissociable blocking agent.

The polyisocyanate can be obtained by causing an urethanization reaction between a monoalcohol and a diisocyanate and causing an isocyanuration reaction afterwards or at the same time.

As the diisocyanate, at least one kind of a diisocyanate compound selected from aliphatic diisocyanates and alicyclic diisocyanates and a monoalcohol having 1 to 20 carbon atoms can be used.

Examples of the aliphatic diisocyanates include butane diisocyanate, pentane diisocyanate, hexamethylene diisocyanate (hereinafter, HDI), trimethyl hexamethylene diisocyanate, and lysine diisocyanate. Among these, HDI is preferred due to the ease of industrial procurement. The aliphatic diisocyanate may be used singly or two or more kinds thereof may be jointly used.

In addition, examples of the alicyclic diisocyanates include isophorone diisocyanate (IPDI), hydrogenated xylylene diisocyanate, hydrogenated diphenylmethane diisocyanate, 1,4-cyclohexane diisocyanate, and the like. Among these, IPDI is preferred due to the ease of industrial procurement. The alicyclic diisocyanate may be used singly or two or more kinds thereof may be jointly used. Any one of the aliphatic diisocyanate and the alicyclic diisocyanate may be used singly or two or more kinds of the aliphatic diisocyanate and the alicyclic diisocyanate may be jointly used.

As a raw material of the polyisocyanate, a monoalcohol having 1 to 20 carbon atoms can be used. The lower limit of the number of carbon atoms in the monoalcohol is preferably 2, more preferably 3, still more preferably 4, and particularly preferably 6. The upper limit is preferably 16, more preferably 12, and still more preferably 9. Only one kind of the monoalcohol may be used or two or more kinds of the monoalcohols may be used in mixture. In addition, the monoalcohol may include an ether group, an ester group, or a carbonyl group in the molecule, but a monoalcohol made of saturated hydrocarbon groups alone is preferred. Furthermore, a monoalcohol having a branch is more preferred. Examples of the monoalcohol include methanol, ethanol, 1-propanol, 2-propanol, 1-butanol, 2-butanol, isobutanol, 1-pentanol, 2-pentanol, isoamyl alcohol, 1-hexanol, 2-hexanol, 1-heptanol, 1-octanol, 2-ethyl-1-hexanol, 3,5,5-trimethyl-1-hexanol, tridecanol, pentadecanol, palmityl alcohol, stearyl alcohol, cyclopentanol, cyclohexanol, methylcyclohexanol, trimethylcyclohexanol, and the like. Among these, isobutanol, 1-butanol, isoamyl alcohol, 1-hexanol, 1-heptanol, 1-octanol, 2-ethyl-1-hexanol, tridecanol, pentadecanol, palmityl alcohol, stearyl alcohol, and 3,5,5-trimethyl-1-cyclohexanol are more preferred due to their excellent compatibility with active hydrogen compounds.

The polyisocyanate which is a precursor of a blocked polyisocyanate preferably contains an isocyanurate ring in the molecule. The isocyanurate ring is a structure that is formed from three isocyanate groups. In the composition for an electrode protective film of an electrostatic capacitance-type input device of the present invention, (d) the compound capable of reacting with acidic groups or alcoholic hydroxy groups by heating is preferably a compound having a structure represented by General Formula (1).

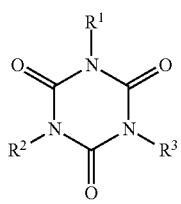

General Formula (1)

In General Formula (1), $R^1$ to $R^3$ each independently represent a monovalent organic group.

In General Formula (1), the monovalent organic groups represented by $R^1$ to $R^3$ may be identical to or different from one another. In General Formula (1), examples of the monovalent organic groups represented by $R^1$ to $R^3$ include groups including a thermally dissociable blocking agent. The monovalent organic groups represented by $R^1$ to $R^3$ are preferably groups to which the group including a thermally dissociable blocking agent is bonded through a divalent linking group derived from the diisocyanate compound which is used in the synthesis of the polyisocyanate and/or a divalent linking group derived from the monoalcohol having 1 to 20 carbon atoms which is used in the synthesis of the polyisocyanate.

The polyisocyanate protected with a thermally dissociable blocking agent can be manufactured by reacting isocyanate groups in a polyisocyanate with a thermally dissociable blocking agent and thus protecting the isocyanate groups. Here, "being thermally dissociable" means that the blocking agent bonded to the isocyanate group is dissociated by heating. A temperature necessary for dissociation varies depending on the structure of the blocking agent and is, for example, 40° C. to 300° C.

Examples of the thermally dissociable blocking agent include oxime-based compounds, alcohol-based compounds, acid amide-based compounds, acid imide-based compounds, phenol-based compounds, amine-based compounds, active methylene-based compounds, imidazole-based compounds, pyrazole-based compounds, and the like. Examples of the oxime-based compounds include formaldoxime, acetoaldoxime, acetoxime, methyl ethyl ketoxime, cyclohexanone oxime, and the like. Examples of the alcohol-based compounds include methanol, ethanol, 2-propanol, n-butanol, sec-butanol, 2-ethyl-1-hexanol, 2-methoxyethanol, 2-ethoxyethanol, 2-butoxyethanol, and the like. Examples of the acid amide-based compounds include acetanilide, acetate amide, ε-caprolactam, δ-valerolactam, γ-butyrolactam, and the like. Examples of the acid imide-based compounds include succinimide, maleic imide, and the like. Examples of the phenol-based compounds include phenol, cresol, ethylphenol, butylphenol, nonylphenol, dinonylphenol, styrenated phenol, hydroxybenzoic acid ester, and the like. Examples of the amine-based compounds include diphenylamine, aniline, carbazole, di-n-propylamine, diisopropylamine, isopropylethylamine, and the like. Examples of the active methylene-based compounds include dimethyl malonate, diethyl malonate, methyl acetoacetate, ethyl acetoacetate, acetylacetone, and the like. Examples of the imidazole-based compounds include imidazole, 2-methylimidazole, and the like. Examples of the pyrazole-based compounds include pyrazole, 3-methylpyrazole, 3,5-dimethylpyrazole, and the like. Among these, from the viewpoint of ease of procurement and the viscosity, reaction temperature, and reaction time of the manufactured blocked polyisocyanate composition, the oxime-based compounds, the acid amide-based compounds, the amine-based compounds, the active methylene-based compounds, and the pyrazole-based compounds are preferred, and methyl ethyl ketoxime, ε-caprolactam, diethyl malonate, ethyl acetoacetate, and 3,5-dimethylpyrazole are more preferred.

One kind of the thermally dissociable blocking agent may be used or two or more kinds of thermally dissociable blocking agents may be used at a desired ratio. In addition, isocyanate groups in the isocyanate may be fully or partially protected with the thermally dissociable blocking agent using a well-known method, but are preferably fully protected. In a case in which all of the isocyanate groups are protected, (the molar number of the thermally dissociable blocking agent)/(the molar number of the isocyanate groups in the polyisocyanate composition) is preferably 1.0 to 1.5. In such a case, excess or unreacted parts of the thermally dissociable blocking agent remain in the blocked isocyanate composition. A protection reaction may be caused without using solvents as for the polyisocyanate or, if necessary, an organic solvent having no reactivity with isocyanate groups may be used and then separated.

The reaction temperature of the protection reaction can be set to −20° C. to 150° C., but is preferably 0° C. to 100° C. from the viewpoint of the reaction rate or side reactions.

The number of blocked isocyanate groups in the blocked isocyanate per molecule is preferably 1 to 10, more preferably 2 to 6, and particularly preferably 3 or 4.

Specific examples of the blocked isocyanate include the following compounds. However, the blocked isocyanate that is used in the present invention is not limited to the following specific examples.

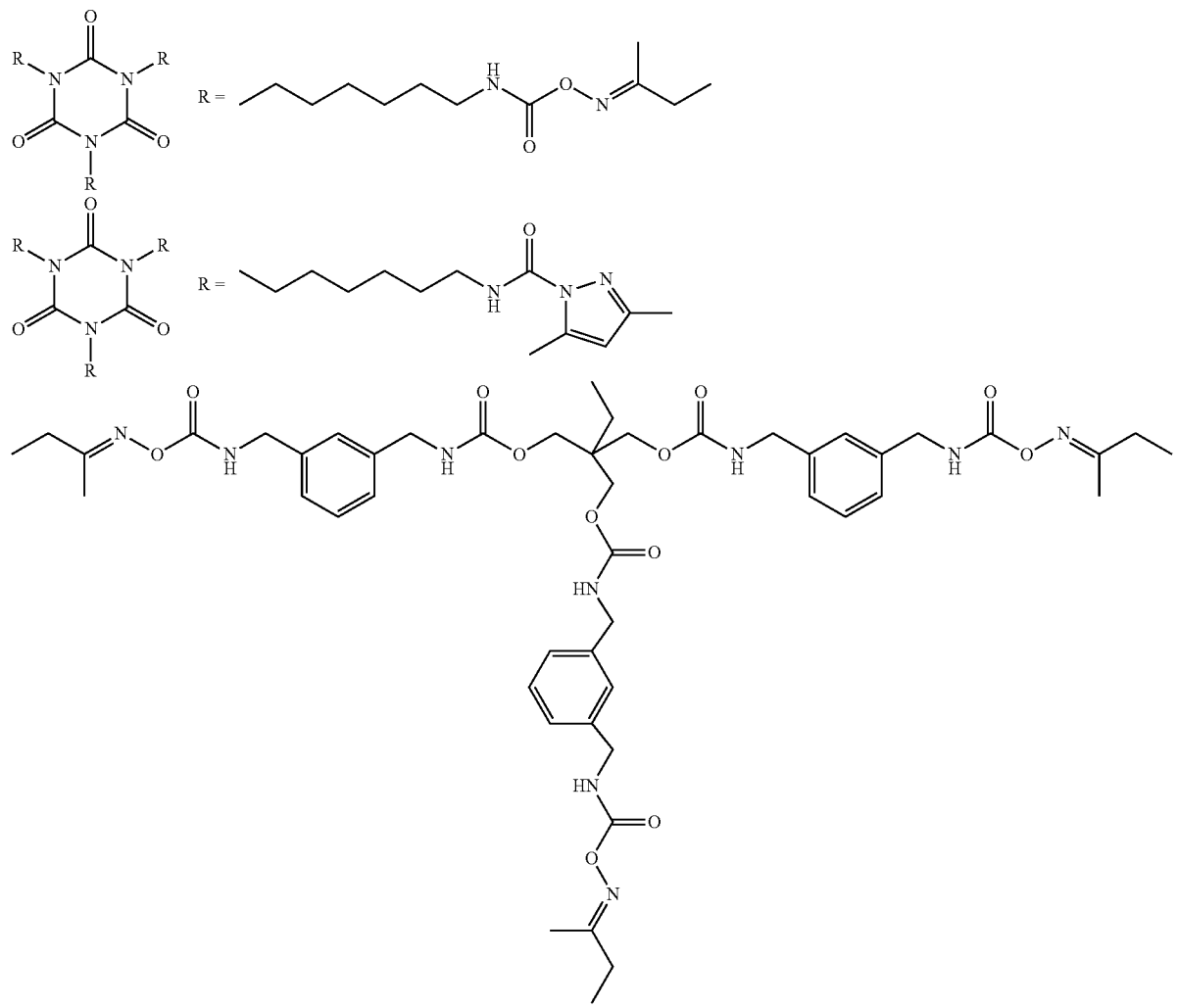

As the blocked isocyanate, commercially available blocked isocyanates can be used. Examples thereof include DURANATE TPA-B80E (manufactured by Asahi Kasei Corporation) and the like.

The weight-average molecular weight of the blocked isocyanate is preferably 200 to 3,000, more preferably 250 to 2,600, and particularly preferably 280 to 2,200.

—(d2) Epoxy Compound—

The epoxy compound is not particularly limited, and a well-known compound can be used.

As the epoxy compound, it is possible to preferably use the compound described in [0096] to [0098] of JP2015-135396A, the content of which is incorporated into the present specification.

Examples of the epoxy compound include EPOX-MK R151 (manufactured by Printec Corporation) and the like.

(Additives)

In the composition for an electrode protective film of an electrostatic capacitance-type input device, additives may be further used. Examples of the additives include the surfactants described in Paragraph 0017 in the specification of JP4502784B and Paragraphs 0060 to 0071 of JP2009-237362A, well-known fluorine-based surfactants, the thermal polymerization inhibitors described in Paragraph 0018 in the specification of JP4502784B, and, furthermore, other additives described in Paragraphs 0058 to 0071 of JP2000-310706A. Examples of the additives that are preferably used in the composition for an electrode protective film of an electrostatic capacitance-type input device include MEGA-FACE F-551 (manufactured by DIC Corporation) which is a well-known fluorine-based surfactant.

[Transfer Film]

A transfer film of the present invention has a temporary support and a photosensitive resin layer including the composition for an electrode protective film of an electrostatic capacitance-type input device of the present invention.

<Temporary Support>

The temporary support that is used in the transfer film is not particularly limited.

(Thickness)

The thickness of the temporary support is not particularly limited, but is generally in a range of 5 to 200 μm and particularly preferably in a range of 10 to 150 μm from the viewpoint of ease of handling, versatility, and the like.

(Material)

The temporary support is preferably a film and more preferably a resin film.

As the film that is used as the temporary support, it is possible to use flexible materials that do not significantly deform, contract, or extend under pressurization or under pressurization and heating. Examples of the temporary support satisfying the above-described property include polyethylene terephthalate films, triacetylcellulose films, polystyrene films, polycarbonate films, and the like, and, among these, biaxially-stretched polyethylene terephthalate films are particularly preferred.

In addition, the temporary support may be transparent and may contain dyed silicon, an alumina sol, a chromium salt, a zirconium salt, or the like.

In addition, the temporary support can be imparted with a conductive property using the method described in JP2005-221726A.

<Constitution of Photosensitive Resin Layer>

A photosensitive resin layer may be photocurable or thermocurable and photocurable. Among these, the photosensitive resin layer is preferably thermocurable and photocurable since it is easy to produce films by transferring and then photocuring the layer and it is possible to impart the reliability and the heat and moisture resistance after the supply of saline water of the layer by producing and then thermally curing films.

In the present specification, for the convenience of description, in a case in which the photosensitive resin layer of the transfer film of the present invention is transferred onto an electrode pattern, is photocured, and thus becomes no longer photocurable, this layer will be continuously termed as the photosensitive resin layer regardless of whether or not the layer is thermocurable. Furthermore, there are cases in which this layer is photocured and then thermocured; however, even in these cases, this layer will be continuously termed as the photosensitive resin layer regardless of whether or not the layer is curable. Similarly, in a case in which the photosensitive resin layer in the transfer film of the present invention is transferred onto an electrode pattern, is thermally cured, and thus becomes no longer thermocurable, this layer will be continuously termed as the photosensitive resin layer regardless of whether or not the layer is photocurable.

The photosensitive resin layer is preferably alkali-soluble. The resin layer being alkali-soluble means that the resin layer dissolves in a weak alkaline aqueous solution, and the resin layer can be preferably developed with a weak alkaline aqueous solution.

(Thickness)

In the transfer film, the thickness of the photosensitive resin layer is preferably 1 to 20 μm, more preferably 2 to 15 μm, and particularly preferably 3 to 12 μm. The photosensitive resin layer is preferably used for image-displaying portions in electrostatic capacitance-type input devices. In such a case, high transparency and an increase in transmittance are important, and in a case in which the thickness of the photosensitive resin layer is sufficiently thin, the transmittance does not easily decrease due to the absorption by the photosensitive resin layer, and short wavelengths are not easily absorbed, which suppresses image-displaying portions being colored to yellow.

<Second Photosensitive Resin Layer>

The transfer film may further have a second photosensitive resin layer on the photosensitive resin layer. Examples of the second photosensitive resin layer include well-known refractive index-adjusting layers and the like.

<Thermoplastic Resin Layer>

In the transfer film, it is also possible to provide a thermoplastic resin layer between the temporary support and the photosensitive resin layer. In a case in which a laminate is formed by transferring the photosensitive resin layer using a transfer material having the thermoplastic resin layer, air bubbles are not easily generated in individual elements formed by being transferred, image unevenness or the like is not easily caused in image display devices, and excellent display characteristics can be obtained.

The thermoplastic resin layer is preferably alkali-soluble. The thermoplastic resin layer plays a role of a cushion material so as to be capable of absorbing protrusions and recesses (also including protrusions, recesses, and the like caused by images and the like which have been previously formed) on a base surface and is preferably capable of transforming along protrusions and recesses on a subject surface.

The thermoplastic resin layer preferably includes the organic macromolecular substance described in JP1993-72724A (JP-H05-72724A) as a component and particularly preferably includes at least one substance selected from organic macromolecular substances having a softening point of approximately 80° C. or lower which is obtained using the Vicat method [specifically, the polymer softening point measurement method based on American Society for Testing and Materials (ASTM International) ASTM D1235].

Specific examples thereof include organic macromolecules such as polyolefins such as polyethylene and polypropylene, ethylene copolymers of ethylene and vinyl acetate or a saponified substance thereof, copolymers of ethylene and an acrylic acid ester or a saponified substance thereof, vinyl chloride copolymers of polyvinyl chloride or vinyl chloride and vinyl acetate or a saponified substance thereof, polyvinylidene chloride, vinylidene chloride copolymers, polystyrene, styrene-based copolymers of styrene and a (meth)acrylic acid ester or a saponified substance thereof, polyvinyl toluene, vinyl toluene copolymers of vinyl toluene and a (meth)acrylic acid ester or a saponified substance thereof, poly(meth)acrylic acid esters, (meth) acrylic acid ester copolymers of butyl (meth)acrylate and vinyl acetate, polyamide resins such as vinyl acetate copolymer nylon, copolymerized nylon, N-alkoxymethylated nylon, and N-dimethylaminated nylon, and the like.

The thickness of the thermoplastic resin layer is preferably 3 to 30 In a case in which the thickness of the thermoplastic resin layer is less than 3 μm, there are cases in which followability during lamination is insufficient and protrusions and recesses on the base surface cannot be fully absorbed. In addition, in a case in which the thickness exceeds 30 there are cases in which loads are applied to drying (solvent removal) during the formation of the thermoplastic resin layer on the temporary support, time is taken for the development of the thermoplastic resin layer, or the process suitability is deteriorated. The thickness of the thermoplastic resin layer is more preferably 4 to 25 μm and particularly preferably 5 to 20 μm.

The thermoplastic resin layer can be formed by means of the application or the like of a prepared liquid including a thermoplastic organic macromolecule, and the prepared liquid that is used in the case of application or the like can be prepared using a solvent. The solvent is not particularly limited as long as the solvent is capable of dissolving macromolecular components constituting the thermoplastic resin layer, and examples thereof include methyl ethyl ketone, cyclohexanone, propylene glycol monomethyl ether acetate, n-propanol, 2-propanol, and the like.

<Interlayer>

In the transfer film, it is also possible to provide an interlayer between the thermoplastic resin layer and the photosensitive resin layer. The interlayer is preferably the layer described in JP1993-72724A (JP-H05-72724A) as "separation layer".

<Protective Film>

The transfer film is preferably further provided with a protective film or the like on the surface of the photosensitive resin layer.

As the protective film, it is possible to appropriately use the protective film described in Paragraphs 0083 to 0087 and 0093 of JP2006-259138A.

Figure 12:
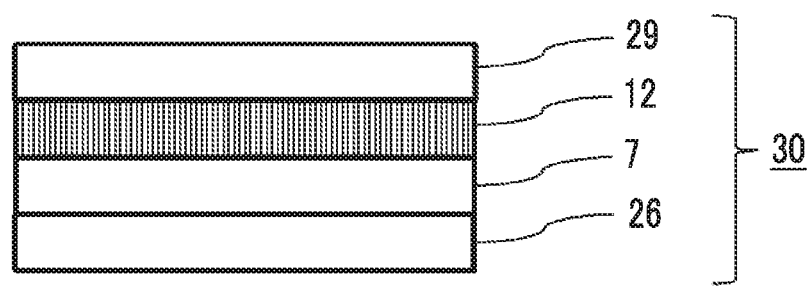
FIG. 12 is a schematic cross-sectional view illustrating an example of a constitution of a transfer film of the present invention.

FIG. 12 illustrates an example of a preferred constitution of the transfer film of the present invention. FIG. 12 is a schematic cross-sectional view of a transfer film 30 of the present invention in which a temporary support 26, a photosensitive resin layer 7, a second photosensitive resin layer 12, and a protective film 29 are laminated adjacent to each other in this order.

<Method for Manufacturing Transfer Film>

A method for manufacturing the transfer film is not particularly limited, and well-known methods can be used.

(Step of Forming Photosensitive Resin Layer on Temporary Support)

A method for manufacturing the transfer film has a step of forming the photosensitive resin layer on the temporary support, and the step of forming the photosensitive resin layer is preferably a step of applying an organic solvent-based resin composition onto the temporary support.

—Organic Solvent-Based Resin Composition—

The organic solvent-based resin composition refers to a resin composition that is soluble in organic solvents.

As the organic solvents, ordinary organic solvents can be used. Examples of the organic solvents include methyl ethyl ketone, propylene glycol monomethyl ether, propylene glycol monomethyl ether acetate, cyclohexanone, methyl isobutyl ketone, ethyl lactate, methyl lactate, caprolactam, and the like.

In the method for manufacturing the transfer film, the organic solvent-based resin composition that is used to form the photosensitive resin layer is the composition for an electrode protective film of an electrostatic capacitance-type input device of the present invention.

<Other Steps>

The method for manufacturing the transfer film may include a step of further forming the thermoplastic resin layer before the formation of the photosensitive resin layer on the temporary support.

After the step of further forming the thermoplastic resin layer, a step of forming the interlayer between the thermoplastic resin layer and the photosensitive resin layer may be provided. Specifically, in the case of forming a photosensitive material having the interlayer, the thermoplastic resin layer is provided by applying and drying a solution obtained by dissolving additives together with the thermoplastic organic macromolecule (coating fluid for the thermoplastic resin layer) on the temporary support, then, the interlayer is laminated by applying and drying a prepared liquid obtained by adding resins and additives to a solvent that does not dissolve the thermoplastic resin layer (coating fluid for the interlayer) on the thermoplastic resin layer, and the photosensitive resin layer is laminated by further applying and drying a coating fluid for the photosensitive resin layer which is prepared using a solvent that does not dissolve the interlayer on the interlayer, whereby the transfer film can be preferably produced.

As a method for manufacturing other photosensitive resin layers, it is possible to employ the method for producing a photosensitive transfer material described in Paragraphs 0094 to 0098 of JP2006-259138A.

<Uses>

The transfer film of the present invention is preferably used for electrode protective films of electrostatic capacitance-type input devices and more preferably used for, among electrode protective films of electrostatic capacitance-type input devices, transparent insulating layers or transparent protective layers. The transfer film of the present invention may have the photosensitive resin layer in a non-cured state, and, in such a case, the transfer film can be preferably used as a transfer film for forming a laminate pattern of an electrode protective film of an electrostatic capacitance-type input device or a transfer film for forming laminate patterns of a refractive index-adjusting layer and an electrode protective film (overcoat) of an electrostatic capacitance-type input device on an electrode pattern by means of a photolithography method.

[Electrode Protective Film of Electrostatic Capacitance-Type Input Device]

A first aspect of an electrode protective film of an electrostatic capacitance-type input device of the present invention is an electrode protective film formed of the composition for an electrode protective film of an electrostatic capacitance-type input device of the present invention.

A second aspect of the electrode protective film of an electrostatic capacitance-type input device of the present invention is an electrode protective film obtained by removing the temporary support from the transfer film of the present invention.

The electrode protective film of an electrostatic capacitance-type input device of the present invention has favorable bending resistance and is thus preferably used as electrode protective films of film sensor-type electrostatic capacitance-type input devices.

[Laminate]

A first aspect of a laminate of the present invention is a laminate having the electrode protective film of an electrostatic capacitance-type input device of the present invention or an electrode protective film of an electrostatic capacitance-type input device formed by transferring the photosensitive resin layer in the transfer film of the present invention on a substrate including an electrode of an electrostatic capacitance-type input device.

A second aspect of the laminate of the present invention is a laminate having a substrate including an electrode of an electrostatic capacitance-type input device and a photosensitive resin layer located on the substrate, in which the photosensitive resin layer includes (a) a binder polymer, (b) a photopolymerizable compound having an ethylenic unsaturated group, (c) a photopolymerization initiator, and (d) a compound capable of reacting with acidic groups or alcoholic hydroxy groups by heating, and (b) the photopolymerizable compound having an ethylenic unsaturated group is (b1) a photopolymerizable compound in which a value obtained by dividing a weight-average molecular weight by an average number of polymerizable groups is 270 or more.

Due to the above-described constitution, the laminate of the present invention has favorable bending resistance.

In the laminate of the present invention, the photosensitive resin layer is preferably cured, the photosensitive resin layer is more preferably subjected to at least one treatment of exposure and heating, and the photosensitive resin layer is particularly preferably subjected to exposure and a heating treatment.

The electrode of the electrostatic capacitance-type input device may be an electrode pattern or a guidance wire. The electrode of the electrostatic capacitance-type input device is preferably an electrode pattern.

<Constitution of Laminate>

The laminate of the present invention preferably has the substrate including the electrode of an electrostatic capacitance-type input device and the photosensitive resin layer located on this substrate and more preferably has at least the substrate, the electrode pattern, and the photosensitive resin layer.

The laminate may further have the second photosensitive resin layer between the electrode and the photosensitive resin layer. The laminate may have the substrate, the electrode pattern, the second photosensitive resin layer disposed adjacent to the electrode pattern, and the photosensitive resin layer disposed adjacent to the second photosensitive resin layer, and the refractive index of the second photosensitive resin layer may be higher than the refractive index of the photosensitive resin layer. In this case, the refractive index of the second photosensitive resin layer is preferably 1.6 or higher. In a case in which the above-described constitution is provided, it is possible to prevent the electrode pattern from being easily visible, and the patterning property becomes favorable.

The laminate of the present invention may further have a transparent film having a refractive index of 1.60 to 1.78 and a thickness of 55 to 110 nm or a transparent film having a different refractive index or thickness on a side of the electrode pattern opposite to the side on which the second photosensitive resin layer is formed. Meanwhile, in the present specification, in the case of being simply mentioned, "transparent films" refer to "transparent film having a refractive index of 1.60 to 1.78 and a film thickness of 55 to 110 nm".

The laminate of the present invention preferably further has a substrate on a side of the transparent film having a refractive index of 1.60 to 1.78 and a thickness of 55 to 110 nm opposite to the side on which the transparent electrode pattern is formed.

Figure 11:
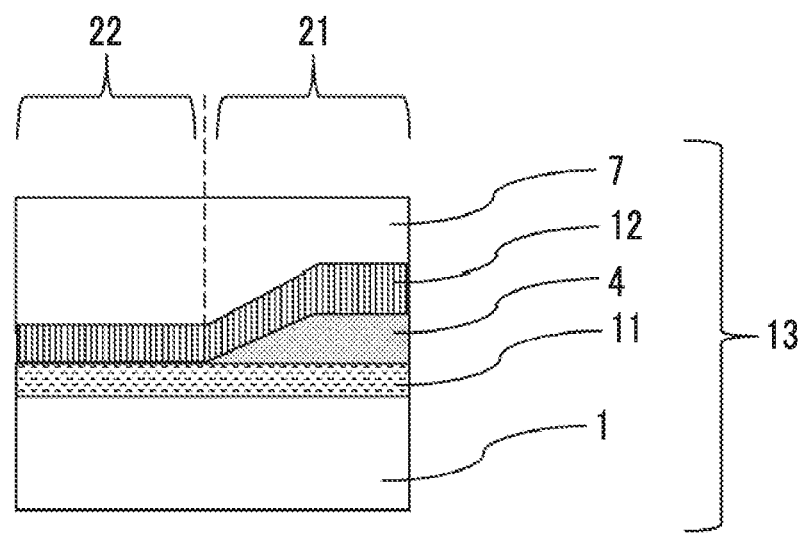
FIG. 11 is a schematic cross-sectional view illustrating an example of a constitution of a laminate of the present invention.

FIG. 11 illustrates an example of the constitution of the laminate of the present invention.

In FIG. 11, a substrate 1 and a transparent film 11 are provided, and, furthermore, a region 21 in which an electrode pattern and a photosensitive resin layer are laminated in this order is provided in a plane. In addition, FIG. 11 illustrates that the laminate includes, in addition to the region 21 in which the electrode pattern and the photosensitive resin layer are laminated in this order, a region in which the substrate 1 and the transparent film 11 are laminated in this order (in the constitution of FIG. 11, a region 22 in which the second photosensitive resin layer 12 and the photosensitive resin layer 7 are laminated in this order (a non-patterned region 22 in which the electrode pattern is not formed)).

The in-plane direction refers to a direction that is substantially parallel to a surface parallel to the substrate of the laminate. Therefore, the fact that the region in which the second electrode pattern 4, the second photosensitive resin layer 12, and the photosensitive resin layer 7 are laminated in this order is included in the in-plane direction means that the orthogonal projection of the region in which the second electrode pattern 4, the second photosensitive resin layer 12, and the photosensitive resin layer 7 are laminated in this order on the surface parallel to the substrate in the laminate is present in a plane parallel to the substrate of the laminate.

Figure 3:
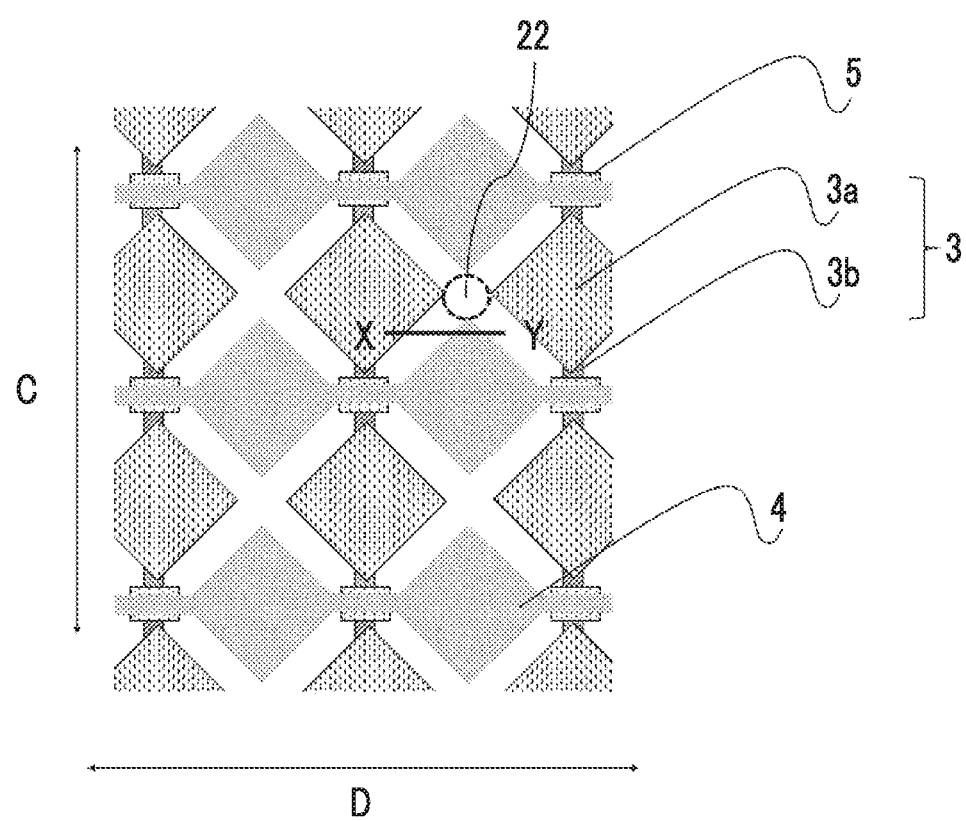
FIG. 3 is an explanatory view illustrating an example of a relationship between an electrode pattern and a non-patterned region in the present invention.

Here, in a case in which the laminate of the present invention is used in an electrostatic capacitance-type input device described below, there are cases in which the electrode pattern is provided in two substantially orthogonal directions which are the row direction and the column direction as a first electrode pattern and a second electrode pattern (for example, refer to FIG. 3). For example, in the constitution of FIG. 3, the electrode pattern in the laminate of the present invention may be the second electrode pattern 4 or a pad portion 3a of a first electrode pattern 3. In other words, in the following description of the laminate of the present invention, there are cases in which the electrode pattern is representatively indicated using a reference sign "4", but the application of the electrode pattern in the laminate of the present invention is not limited to the second electrode pattern 4 in the electrostatic capacitance-type input device of the present invention, and the electrode pattern may be used as the pad portion 3a of the first electrode pattern 3.

The laminate of the present invention preferably includes a non-patterned region in which the electrode pattern is not formed. In the present specification, the non-patterned region refers to a region in which the second electrode pattern 4 is not formed.

FIG. 11 illustrates an aspect in which the laminate of the present invention includes the non-patterned region 22.

The laminate of the present invention preferably includes the region in which the substrate and the transparent film are laminated in this order in the plane in at least a part of the non-patterned region 22 in which the electrode pattern is not formed.

In the laminate of the present invention, in the region in which the substrate and the transparent film are laminated in this order, transparent films are preferably adjacent to each other.

In the other region of the non-patterned region 22, other members may be disposed in arbitrary locations within the scope of the gist of the present invention, and, for example, in a case in which the laminate of the present invention is used in the electrostatic capacitance-type input device described below, it is possible to laminate a mask layer 2, an insulating layer 5, an additional conductive element 6, and the like in FIG. 1.

FIG. 11 illustrates an aspect in which the transparent film 11 is adjacently laminated on the substrate 1.

Here, within the scope of the gist of the present invention, a third transparent film may be laminated between the substrate and the transparent film. For example, a third transparent film having a refractive index of 1.50 to 1.52 (not illustrated in FIG. 11) may be provided between the substrate and the transparent film.

FIG. 11 illustrates an aspect in which the second electrode pattern 4 is adjacently laminated on a region of a part of the transparent film 11.

The shape of an end portion of the second electrode pattern 4 is not particularly limited and may be a taper shape as illustrated in FIG. 11, and, for example, the end portion may have a taper shape in which the surface on the substrate side is wider than the surface on the side opposite to the substrate.

Here, when the end portion of the electrode pattern has a taper shape, the angle of the end portion of the electrode pattern (hereinafter, also referred to as the taper angle) is preferably 30° or less, more preferably 0.1° to 15°, and particularly preferably 0.5° to 5°.

In the present specification, the taper angle can be obtained using the following method for measuring the taper angle: a microscopic photograph of the end portion of the electrode pattern is captured, the taper portion in the microscopic photograph is approximated to a triangle, and the taper angle is directly measured.

Figure 10:
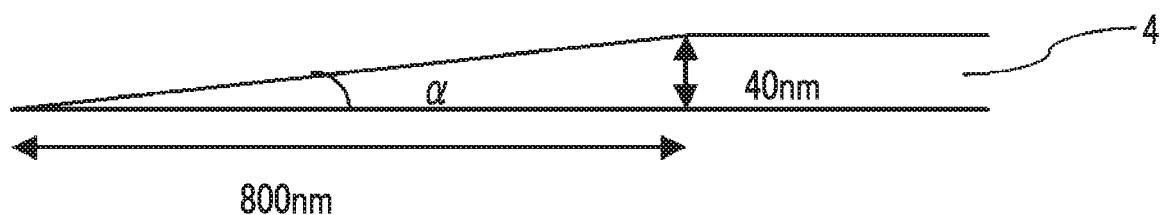
FIG. 10 is an explanatory view illustrating an example of a taper shape of an end portion of the electrode pattern.

FIG. 10 illustrates an example of a case in which the end portion of the electrode pattern has a taper shape. In a triangle obtained by approximating the taper portion in FIG. 10, the bottom surface is 800 nm, the height (the thickness at the top surface portion substantially parallel to the bottom surface) is 40 nm, and the taper angle α at this time is approximately 3°. The bottom surface of the triangle obtained by approximating the taper portion is preferably 10 to 3,000 nm, more preferably 100 to 1,500 nm, and particularly preferably 300 to 1,000 nm.

Meanwhile, a preferred range of the height of the triangle obtained by approximating the taper portion is the same as the preferred range of the thickness of the electrode pattern.

FIG. 11 illustrates an aspect in which, in the region 21 in which the electrode pattern and the photosensitive resin layers are laminated in this order, the electrode pattern, the second photosensitive resin layer, and the photosensitive resin layer are adjacent to each other.

FIG. 11 illustrates an aspect in which the photosensitive resin layer 7 is laminated on a surface of the second photosensitive resin layer 12 on a side opposite to the surface on which the electrode pattern is formed.

In the laminate of the present invention, the electrode pattern and the photosensitive resin layer may be laminated together through the second photosensitive resin layer as illustrated in FIG. 11, but the laminate preferably includes a region in which the electrode pattern and the photosensitive resin layer are adjacent to each other (not illustrated).

In the laminate of the present invention, both of the electrode pattern and the non-patterned region 22 in which the electrode pattern is not formed are preferably continuously coated with the transparent film directly or through other layers.

Here, "being continuously coated" means that the transparent film is not a patterned film but a continuous film. That is, the transparent film preferably has no opening portions since the electrode pattern is made to be rarely visible.

In addition, the transparent electrode pattern and the non-patterned region 22 are more preferably coated with the transparent film directly than through other layers. In a case in which the transparent electrode pattern and the non-patterned region are coated through other layers, examples of "other layers" include the insulating layer 5 included in the electrostatic capacitance-type input device of the present invention described below, an electrode pattern on the second layer in a case in which two or more electrode patterns are included as in the electrostatic capacitance-type input device of the present invention described below, and the like.

FIG. 11 illustrates an aspect in which the second photosensitive resin layer 12 is laminated. The photosensitive resin layer 12 is laminated so as to astride the region in which the second electrode pattern 4 on the transparent film 11 is not laminated and the region in which the second electrode pattern 4 is laminated. That is, the second photosensitive resin layer 12 is adjacent to the transparent film 11 and, furthermore, the photosensitive resin layer 12 is adjacent to the second electrode pattern 4.

In addition, in a case in which the end portion of the second electrode pattern 4 has a taper shape, the second photosensitive resin layer 12 or the photosensitive resin layer 7 is preferably laminated along the taper shape (at the same slope as the taper angle).

<Material of Laminate>
(Substrate)

The laminate of the present invention has the substrate including the electrode of the electrostatic capacitance-type input device. In the substrate including the electrode of the electrostatic capacitance-type input device, the substrate and the electrode are preferably separate members.

The substrate is preferably a film substrate from the viewpoint of providing electrostatic capacitance-type input devices having favorable bending resistance. In addition, the substrate is preferably a transparent substrate. That is, in the laminate of the present invention, the substrate is more preferably a transparent film substrate.

The refractive index of the substrate is particularly preferably 1.50 to 1.52.

In a case in which a film substrate is used as the substrate, a transparent film substrate causing no optical distortion or a transparent film substrate having high transparency is more preferably used, and specific examples include polyethylene terephthalate, polyethylene naphthalate, polycarbonate, triacetyl cellulose, or cycloolefin polymers.

The laminate is also preferably a constitution in which the electrode and the photosensitive resin layer are provided on both surfaces of the substrate respectively. In this case, the laminate is preferably used as a film sensor.

(Electrode)

The electrode is preferably a fine conductive wire.
The electrode is preferably an electrode pattern.
A material of the electrode pattern is not particularly limited, and well-known materials can be used.

In the laminate of the present invention, the electrode of the electrostatic capacitance-type input device preferably includes at least one kind of metal selected from Au, Ag, Cu, and Al or an alloy including at least one kind of metal selected from Au, Ag, Cu, and Al.

Examples of other metals that are used for the alloy including at least one kind of metal selected from Au, Ag, Cu, and Al include tin, palladium, nickel, chromium, and the like.

Among these, the electrode is preferably Ag since the conductivity of the electrode is excellent.

The electrode is also preferably formed of a metal nanowire made of silver or a silver alloy. A method for manufacturing the metal nanowire is not particularly limited, and the metal nanowire may be produced using any method and is preferably manufactured by reducing metal ions in a solvent in which a halogen compound and a dispersant are dissolved. In addition, after the formation of the metal nanowire, a desalination treatment is preferably carried out according to a normal method from the viewpoint of dispersibility and the temporal stability of conductive films.

In addition, as the method for manufacturing the metal nanowire, it is possible to use the method described in JP2009-215594A, JP2009-242880A, JP2009-299162A, JP2010-84173A, JP2010-86714A, JP2009-505358A, and the like.

From the viewpoint of adhesion between the electrode and the substrate, the electrode preferably includes a binder.

The binder is preferably a water-soluble macromolecule since the adhesion between the electrode and the substrate is more favorable. Examples of the binder include polysaccharides such as gelatin, carrageenan, polyvinyl alcohol (PVA), polyvinyl pyrrolidone (PVP), and starch, cellulose and derivatives thereof, polyethylene oxide, polysaccharide, polyvinylamine, chitosan, polylysine, polyacrylic acid, polyarginic acid, polyhyaluronic acid, carboxycellulose, gum arabic, sodium alginate, and the like. Among these, gelatin is preferred since the adhesion between the electrode and the substrate is more favorable.

Meanwhile, as the gelatin, in addition to lime-treated gelatin, acid-treated gelatin or the like may be used. Hydrolysates of gelatin, gelatin enzymatic decomposition products, and other gelatin in which an amino group and/or a carboxyl group are modified (phthalated gelatin or acetylated gelatin) can be used.

In a case in which the electrode includes metal and the binder, the volume ratio of the metal to the binder (the volume of the metal/the volume of the binder) is preferably 1.0 or more and more preferably 1.5 or more. The conductivity of the electrode can be further enhanced by setting the volume ratio of the metal to the binder to 1.0 or more. The upper limit is not particularly limited, but is preferably 4.0 or less and more preferably 2.5 or less from the viewpoint of productivity.

Meanwhile, the volume ratio of the metal to the binder can be computed from the densities of the metal and the binder included in the electrode. For example, the volume ratio is obtained by considering the density of silver as 10.5 $g/cm^3$ in a case in which the metal is silver and the density of gelatin as 1.34 $g/cm^3$ in a case in which the binder is gelatin in the computation.

One of preferred aspects of the electrode is an aspect in which the electrode includes metallic silver, gelatin, and a macromolecule that is different from gelatin.

The macromolecule that is different from gelatin (hereinafter, also referred to simply as macromolecule) is preferably a macromolecule not including protein.

More specifically, examples thereof include at least any resin selected from the group consisting of an acrylic resin, a styrene resin, a vinyl resin, a polyolefin resin, a polyester resin, a polyurethane resin, a polyamide resin, a polycarbonate resin, a polydiene resin, an epoxy resin, a silicone resin, a cellulose polymer, and a chitosan polymer, copolymers made of monomers constituting the above-described resins, and the like. Among these, macromolecules that are not decomposed with a protein decomposition enzyme are preferred, and examples thereof include an acrylic resin, a styrene resin, a polyester resin, and the like.

Among these, preferred aspects of the macromolecule are described in [0023] to [0042] of JP2014-206936A, the content of which is incorporated into the present specification.

A wire width of the fine conductive wire as the electrode is not particularly limited; however, from the viewpoint of a capability of relatively easily forming low-resistance electrodes, the upper limit is preferably 30 μm or less, more preferably 15 μm, still more preferably 10 μm, particularly preferably 9 μm or less, and most preferably 7 μm or less. The lower limit of the wire width of the fine conductive wire is preferably 0.5 μm or more and more preferably 1.0 μm or more.

A thickness of the electrode is not particularly limited; however, from the viewpoint of conductivity and visibility, the thickness can be selected from 0.00001 mm to 0.2 mm and is preferably 30 μm or less, more preferably 20 μm or less, still more preferably 0.01 to 9 μm, and most preferably 0.05 to 5 μm.

Figure 16:
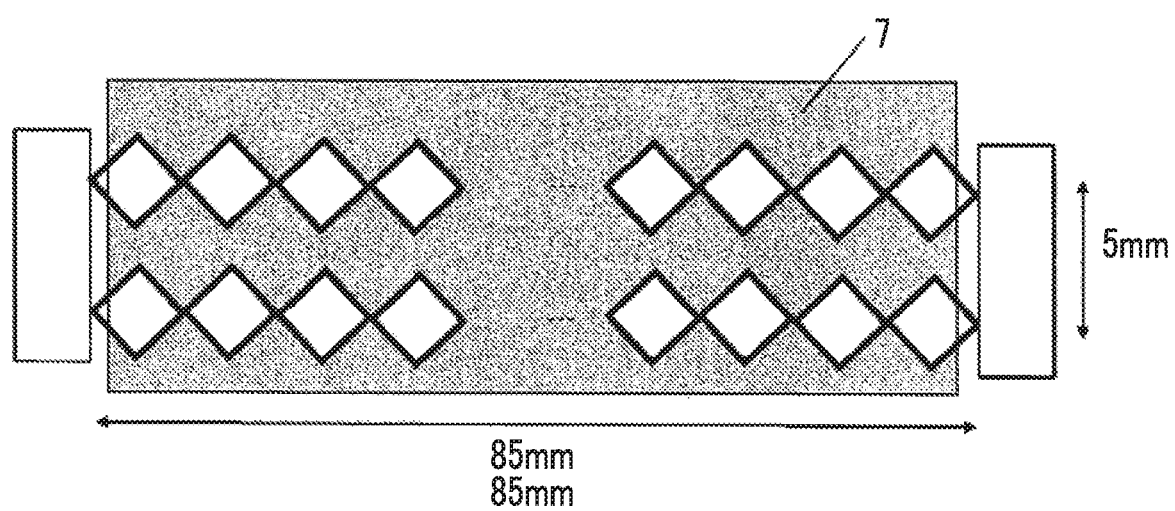
FIG. 16 is a schematic view illustrating an example of the electrode pattern.
Figure 17:
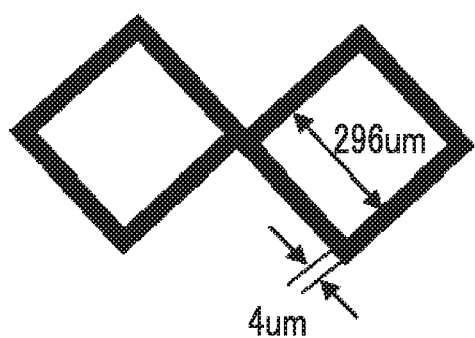
FIG. 17 is a schematic view illustrating an enlarged shape of an example of a pattern of an electrode.

FIG. 16 is a schematic view illustrating an example of the electrode pattern. FIG. 17 illustrates a schematic view illustrating an enlarged shape of an example of a pattern of the electrode. In FIG. 16, a lattice as the electrode pattern (no reference sign) and the photosensitive resin layer 7 are laminated. In FIG. 16, the lengths of the respective sides of the photosensitive resin layer 7 are described, and, in FIG. 17, the length of one side of the lattice of the electrode pattern is described.

The lattice includes opening regions that are surrounded by fine conductive wires as the electrode. The upper limit of a length W of one side of the lattice is preferably 800 μm or less and more preferably 600 μm or less. The lower limit of the length W of one side of the lattice is preferably 400 μm or more.

From the viewpoint of visible light transmittance, an opening ratio of the electrode is preferably 85% or more, more preferably 90% or more, and most preferably 95% or more. The opening ratio corresponds to a ratio of a transmissible portion which is the electrode excluding the fine conductive wire to the entire electrode.

The lattice preferably has a substantially rhombus shape. Additionally, the lattice may have a polygonal shape (for example, a triangular shape, a quadrangular shape, or a hexagonal shape). In addition, the shape of the side may be, in addition to a linear shape, a curved shape or an arc shape. In the case of an arc shape, for example, two opposing sides may be provided with an arc shape protruding outwards, and the other two opposing sides may be provided with an arch shape protruding inwards. In addition, the shapes of the respective sides may be a wavy shape in which an arc protruding outwards and an arc protruding inwards continue. It is needless to say that the shape of the respective sides may be a sine curve.

Meanwhile, in FIG. 16, the fine conductive wire as the electrode is formed as a mesh pattern, but is not limited to this aspect, and may be a stripe pattern.

Meanwhile, the electrode is not limited to the aspect constituted of the mesh structure of the fine conductive wire, and may be constituted of, for example, metal paste such as silver paste or copper paste or metal nanowire particles of a silver nanowire, a copper nanowire, or the like. Among these, a silver nanowire is preferred from the viewpoint of excellent conductivity and transparency.

Meanwhile, the patterning of the electrode can be selected depending on the material of the electrode portion, and a photolithography method, a resist mask screen printing-etching method, an ink jet method, a printing method, or the like may be used.

(Photosensitive Resin Layer)

A preferred range of the photosensitive resin layer included in the laminate of the present invention is the same as the preferred range of the photosensitive resin layer in the transfer film of the present invention.

<Method for Manufacturing Laminate>

A method for manufacturing the laminate is not particularly limited, but the method preferably includes a step of transferring the photosensitive resin layer of the transfer film onto the substrate including the electrode of the electrostatic capacitance-type input device using the transfer film of the present invention.

The method for manufacturing the laminate preferably includes a step of laminating the second photosensitive resin layer and the photosensitive resin layer of the transfer film of the present invention in this order on the electrode (preferably the electrode pattern).

In a case in which the above-described constitution is provided, it is possible to collectively transfer the second photosensitive resin layer and the photosensitive resin layer of the laminate and easily manufacture laminates from which the electrode pattern is not easily visible with favorable productivity.

Meanwhile, the second photosensitive resin layer is preferably formed on the electrode pattern in the patterned region and on the substrate or the transparent film in the non-patterned region directly or through other layers.

(Surface Treatment of Substrate)

In addition, in order to enhance the adhesion of the respective layers after lamination in the subsequent transfer step, it is possible to carry out a surface treatment on a noncontact surface of the substrate (between surfaces of the substrate constituting the electrostatic capacitance-type input device, a surface on a side opposite to a surface which is contacted with input means such as fingers) in advance. As the surface treatment, it is preferable to carry out a surface treatment using a silane compound (silane coupling treatment). A silane coupling agent is preferably an agent having a functional group that interacts with photosensitive resins. For example, a silane coupling liquid (an aqueous solution of 0.3% by mass of N-β(aminoethyl)γ-aminopropyltrimethoxysilane, trade name: KBM603, manufactured by Shin-Etsu Chemical Co., Ltd.) is showered on the surface for 20 seconds, and the surface is cleaned by means of pure water showering. After that, a reaction is preferably caused by means of heating. A heating tank may be used or preliminary heating may be used, and the reaction can be accelerated in any cases.

(Formation of Electrode)

The electrode can be formed on the substrate or the transparent film having a refractive index of 1.6 to 1.78 and a thickness of 55 to 110 nm using a method for forming the first electrode pattern 3, the second electrode pattern 4, and the additional conductive element 6 or the like in the description of the electrostatic capacitance-type input device of the present invention described below or the like, and a method in which a photosensitive film is used is preferred.

In addition, the formation of the electrode is described in [0053] to [0074] of JP2014-206936A or [0049] to [0061] of JP2015-69585A, the content of which is incorporated into the present specification.

(Formation of Photosensitive Resin Layer)

Examples of a method for forming the photosensitive resin layer include methods having a protective film-removing step of removing the protective film from the transfer film of the present invention, a transfer step of transferring the photosensitive resin layer in the transfer film of the present invention from which the protective film has been removed onto the electrode, an exposure step of exposing the photosensitive resin layer which has been transferred onto the electrode, and a development step of developing the photosensitive resin layer which has been exposed.

—Transfer Step—

The transfer step is preferably a step of transferring the photosensitive resin layer in the transfer film of the present invention from which the protective film has been removed onto the electrode (preferably the electrode pattern).

In this case, a method including a step of removing the temporary support after laminating the photosensitive resin layer in the transfer film of the present invention on the electrode is preferred.

The photosensitive resin layer is transferred (attached) onto the surface of the electrode by overlaying, pressurizing, and/or heating the photosensitive resin layer on the surface of the electrode. For the attachment, well-known laminators such as a laminator, a vacuum laminator, and an auto-cut laminator capable of enhancing productivity can be used.

—Exposure Step, Development Step, and Other Steps—

As examples of the exposure step, the development step, and other steps, it is possible to preferably use the method described in Paragraphs 0035 to 0051 of JP2006-23696A even in the present invention.

The exposure step is preferably a step of exposing the photosensitive resin layer which has been transferred onto the electrode pattern.

Specific examples thereof include a method in which a predetermined mask is disposed above the photosensitive resin layer and the temporary support which have been formed on the electrode pattern and then the photosensitive resin layer is exposed to a light source above the mask (through the mask and the temporary support).

Here, as the light source for the exposure, it is possible to appropriately select and use a light source as long as the light source is capable of radiating light having wavelengths in a range (for example, 365 nm, 405 nm, or the like) with which the photosensitive resin layer can be cured. Specific examples thereof include an ultrahigh-pressure mercury lamp, a high-pressure mercury lamp, a metal halide lamp, and the like. The exposure amount is, generally, approximately 5 to 200 $mJ/cm^2$ and preferably approximately 10 to 100 $mJ/cm^2$.

The development step is a step of developing the exposed photosensitive resin layers.

The development step is a narrowly-defined development step in which the photosensitive resin layer which has been pattern-exposed is pattern-developed using a developer.

The development can be carried out using a developer. The developer is not particularly limited, and it is possible to use well-known developers such as the developer described in JP1993-72724A (JP-H05-72724A). Furthermore, the developer is preferably a developer in which the photosensitive resin layer performs dissolution-type development behaviors and, for example, preferably a developer including a compound having a power of Ka (pKa; Ka represents the acid dissociation constant) of 7 to 13 at a concentration of 0.05 to 5 mol/L. Meanwhile, in a case in which the photosensitive resin layer does not form any patterns, the developer is preferably a developer which performs development behaviors so as not to dissolve non-alkali development-type coloring composition layers and, for example, preferably a developer including a compound having a pKa of 7 to 13 at a concentration of 0.05 to 5 mol/L. To the developer, a small amount of a water-miscible organic solvent may be further added. Examples of the water-miscible organic solvent include methanol, ethanol, 2-propanol, 1-propanol, butanol, diacetone alcohol, ethylene glycol monomethyl ether, ethylene glycol monoethyl ether, ethylene glycol mono-n-butyl ether, benzyl alcohol, acetone, methyl ethyl ketone, cyclohexanone, ε-caprolactone, γ-butyrolactone, dimethylformamide, dimethylacetamide, hexamethylphosphoramide, ethyl lactate, methyl lactate, ε-caprolactam, N-methyl pyrrolidone, and the like. The concentration of the organic solvent is preferably 0.1% by mass to 30% by mass.

In addition, to the developer, it is possible to further add a well-known surfactant. The concentration of the surfactant is preferably 0.01% by mass to 10% by mass.

The development method may be any one of puddle development, shower development, shower and spin development, dip development, and the like. In the case of the shower development, a developer is showered onto the photosensitive resin layer which has been exposed, whereby it is possible to remove non-cured portions. Furthermore, in a case in which the thermoplastic resin layer, the interlayer, and/or the like are provided, it is preferable to shower an alkaline liquid that does not easily dissolve the photosensitive resin layer and remove the thermoplastic resin layer, the interlayer, and/or the like before development. In addition, after the development, it is preferable to shower a cleaning agent or the like and remove development residue by rubbing the surface with a brush or the like. The liquid temperature of the developer is preferably 20° C. to 40° C. The pH of the developer is preferably 8 to 13.

The method for manufacturing the laminate may have other steps such as a post exposure step.

Patterning exposure or full-surface exposure may be carried out after the peeling of the temporary support or before the peeling of the temporary support (the temporary support may be peeled off after carrying out exposure before the peeling of the temporary support). The exposure may be exposure through a mask or digital exposure using a laser or the like.

—Heating Step—

The method for manufacturing the laminate preferably includes a step of heating the transferred photosensitive resin layer and more preferably includes a step of turning at least a part of the carboxyl group-containing acrylic resin into a carboxylic acid anhydride by heating the transferred photosensitive resin layer from the viewpoint of enhancing the heat and moisture resistance after the supply of saline water. The transferred photosensitive resin layer is preferably heated after exposure and development, that is, the step is preferably a post baking step carried out after exposure and development. In a case in which the photosensitive resin layer is thermocurable, particularly, a post baking step is preferably carried out.

The heating temperature in the step of turning at least a part of the carboxyl group-containing acrylic resin into a carboxylic acid anhydride by heating the transferred photosensitive resin layer is preferably 100° C. to 160° C. in a case in which a film substrate is used as the substrate and more preferably 140° C. to 150° C.

The method for manufacturing the laminate preferably includes a step of curing the photosensitive resin layer and more preferably includes a step of pattern-curing the photosensitive resin layer. In such a case, it is possible to develop the photosensitive resin layer in a desired pattern by means of photolithography after the photosensitive resin layer is transferred onto the electrode pattern from the transfer film of the present invention.

The method for manufacturing the laminate more preferably includes, after the step of curing the photosensitive resin layer, a step of removing non-cured portions (only non-exposed portions or only exposed portions in the case of photocuring) of the photosensitive resin layer by means of development.

[Electrostatic Capacitance-Type Input Device]

The electrostatic capacitance-type input device of the present invention includes the laminate of the present invention.

The electrostatic capacitance-type input device of the present invention is preferably connected to a flexible wire formed on a polyimide film or the like at a terminal portion of a guidance wire. In order for that, the terminal portion of the guidance wire is preferably not covered with the photosensitive resin layer.

Figure 13:
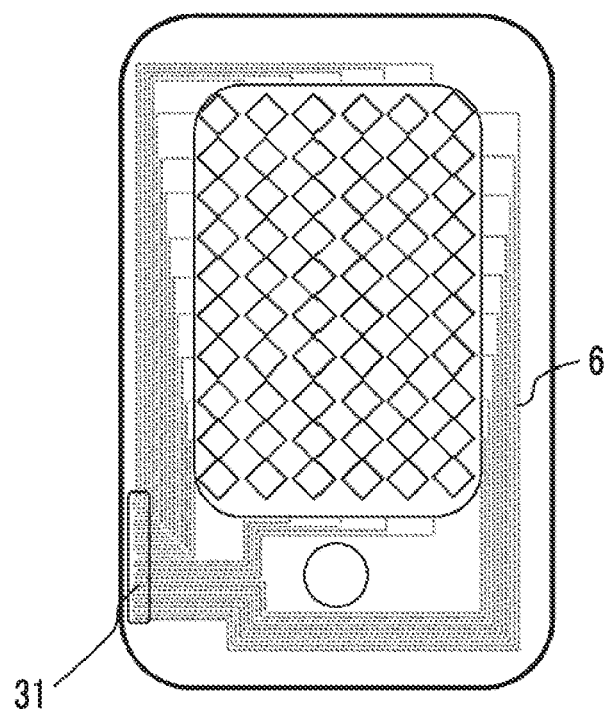
FIG. 13 is a top view illustrating still another example of the constitution of the electrostatic capacitance-type input device of the present invention and illustrates an aspect including a terminal portion (end portion) of a guidance wire which is pattern-exposed and is not covered with a photosensitive resin layer.

The above-described aspect is illustrated in FIG. 13. FIG. 13 illustrates an electrostatic capacitance-type input device having the following constitution which includes a guidance wire (the additional conductive element 6) as the electrode pattern and a terminal portion 31 of the guidance wire.

The photosensitive resin layer on the terminal portion 31 of the guidance wire forms a non-cured portion (non-exposed portion) and is thus removed by means of development, whereby the terminal portion 31 of the guidance wire is exposed.

Figure 14:
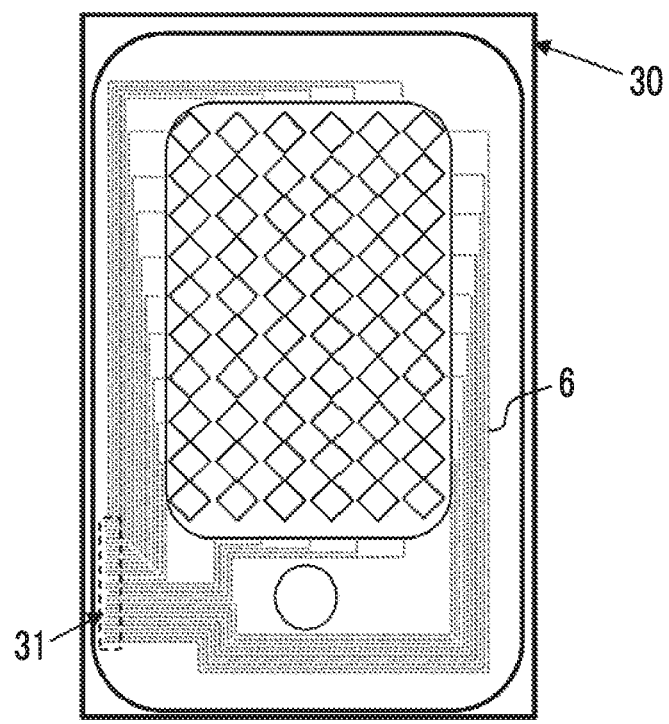
Figure 15:
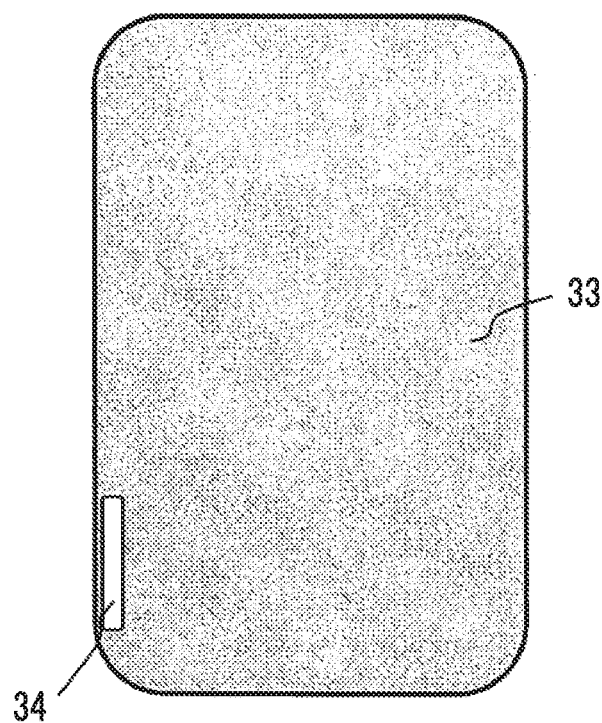
FIG. 15 is a schematic view illustrating an example of a desired pattern in which the photosensitive resin layer is cured.

A specific exposure and development aspect is illustrated in FIGS. 14 and 15. FIG. 14 illustrates a state in which the transfer film 30 of the present invention having the photosensitive resin layer is laminated on the electrode pattern in the electrostatic capacitance-type input device by means of lamination and is to be cured by means of exposure or the like. In a case in which photolithography is used, that is, the transfer film is cured by means of exposure, the electrostatic capacitance-type input device can be obtained by pattern-exposing a cured portion (exposed portion) 33 of the photosensitive resin layer having a shape illustrated in FIG. 15 using a mask and developing a non-exposed portion. Specifically, in FIG. 15, an opening portion 34 corresponding to the terminal portion of the guidance wire as the non-cured portion of the photosensitive resin layer and the end portion of the transfer film of the present invention having the photosensitive resin layer which protrudes outside the contour of a frame portion of the electrostatic capacitance-type input device are removed, and consequently, a cured portion (desired pattern for not covering the terminal portion (lead-out wire portion) of the guidance wire) of the photosensitive resin layer is obtained.

Therefore, it is possible to directly connect the flexible wire produced on the polyimide film to the terminal portion 31 of the guidance wire, and thus it becomes possible to send signals from sensors to electric circuits.

Hereinafter, the detail of a preferred aspect of the electrostatic capacitance-type input device of the present invention will be described.

The electrostatic capacitance-type input device of the present invention has a substrate (corresponding to the substrate in the laminate of the present invention; also referred to as a front surface plate) and at least the following elements (3) to (5), (7), or (8) on a noncontact surface side of the substrate and preferably has the laminate of the present invention:

(3) a plurality of first electrode patterns in which a plurality of pad portions are formed so as to extend in a first direction through a connection portion;

(4) a plurality of second electrode patterns which is electrically insulated from the first electrode patterns and is made of a plurality of pad portions formed so as to extend in a direction orthogonal to the above-described first direction;

(5) an insulating layer that electrically insulates the first electrode pattern and the second electrode pattern;

(7) a second photosensitive resin layer formed so as to fully or partially cover the elements (3) to (5); and (8) a photosensitive resin layer adjacently formed so as to cover the element (7).

Here, the second photosensitive resin layer (7) corresponds to the second photosensitive resin layer in the laminate of the present invention. In addition, the photosensitive resin layer (8) corresponds to the photosensitive resin layer in the laminate of the present invention. Meanwhile, generally, the photosensitive resin layer is preferably a so-called transparent protective layer in well-known electrostatic capacitance-type input devices.

In the electrostatic capacitance-type input device of the present invention, the first electrode pattern (3) and the second electrode pattern (4) may or may not be a transparent electrode pattern but are preferably a transparent electrode pattern from the viewpoint of bending resistance.

The electrostatic capacitance-type input device of the present invention preferably further has an additional conductive element other than the first electrode pattern and the second electrode pattern which is electrically connected to at least one of a first electrode pattern or a second electrode pattern (6).

Here, in a case in which the second electrode pattern (4) is not the electrode pattern in the laminate of the present invention and the additional conductive element (6) is not provided, the first electrode pattern (3) corresponds to the electrode pattern in the laminate of the present invention.

In a case in which the second electrode pattern (4) is the electrode pattern in the laminate of the present invention and the additional conductive element (6) is not provided, at least one of the first electrode pattern (3) or the second electrode pattern (4) corresponds to the electrode pattern in the laminate of the present invention.

In a case in which the second electrode pattern (4) is not the electrode pattern in the laminate of the present invention and the additional conductive element (6) is provided, at least one of the first electrode pattern (3) or the additional conductive element (6) corresponds to the electrode pattern in the laminate of the present invention.

In a case in which the second electrode pattern (4) is the electrode pattern in the laminate of the present invention and the additional conductive element (6) is provided, at least one of the first electrode pattern (3), the second electrode pattern (4), or the additional conductive element (6) corresponds to the electrode pattern in the laminate of the present invention.

The electrostatic capacitance-type input device of the present invention preferably further has a transparent film (2) between the first electrode pattern (3) and the substrate, between the second electrode pattern (4) and the substrate, or between the additional conductive element (6) and the substrate. Here, the transparent film (2) preferably corresponds to the transparent film having a refractive index of 1.6 to 1.78 and a thickness of 55 to 110 nm in the laminate of the present invention from the viewpoint of further improving the electrode pattern-masking property.

The electrostatic capacitance-type input device of the present invention preferably has a mask layer (1) and/or a decorative layer as necessary. The mask layer is also provided as a black trim around a region touched by a finger, a stylus, or the like in order to prevent the guidance wire of the electrode pattern from being visible from a touch side or decorate input devices. The decorative layer is provided as a trim around the region touched by a finger, a stylus, or the like in order for decoration, and, for example, a white decorative layer is preferably provided.

The mask layer (1) and/or the decorative layer are preferably provided between the transparent film (2) and the substrate, between the first electrode pattern (3) and the substrate, between the second electrode pattern (4) and the substrate, or between the additional conductive element (6) and substrate. The mask layer (1) and/or the decorative layer are more preferably provided adjacent to the substrate.

In the case of being provided with a constitution in which the electrode pattern is sandwiched using the transparent film having a refractive index of 1.6 to 1.78 and a thickness of 55 to 110 nm and the second photosensitive resin layer, the electrostatic capacitance-type input device of the present invention is capable of improving a problem of the electrode pattern-masking property.

<Constitution of Electrostatic Capacitance-Type Input Device>

First, a preferred constitution of the electrostatic capacitance-type input device of the present invention will be described together with methods for manufacturing the respective members constituting the device. FIG. 1 is a cross-sectional view illustrating a preferred constitution of the electrostatic capacitance-type input device of the present invention. FIG. 1 illustrates an aspect in which an electrostatic capacitance-type input device 10 is constituted of the substrate 1, the mask layer 2, the transparent film 11 having a refractive index of 1.6 to 1.78 and a thickness of 55 to 110 nm, the first electrode pattern 3 (only a connection portion 3*b* is illustrated in FIG. 1), the second electrode pattern 4, the insulating layer 5, the additional conductive element 6, a second photosensitive resin layer 12, and the photosensitive resin layer 7.

Figure 9:
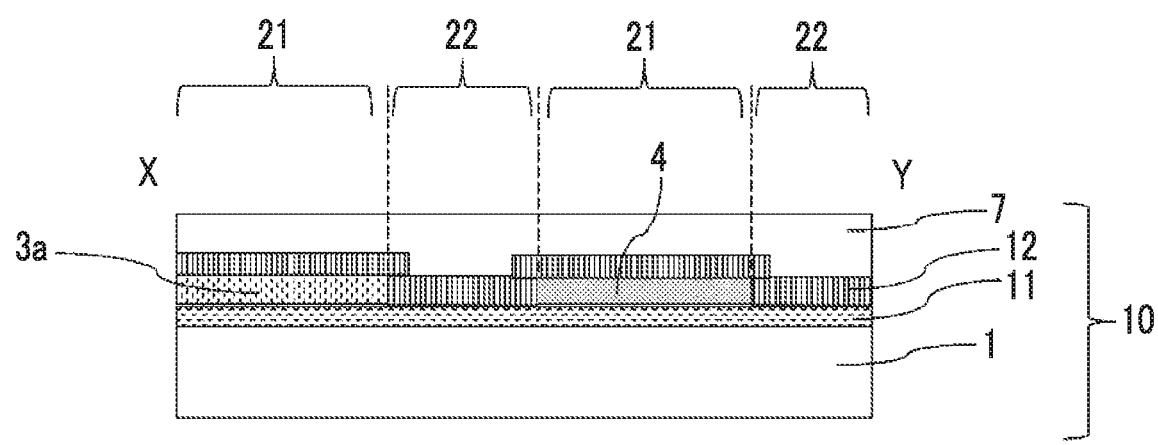
FIG. 9 is a schematic cross-sectional view illustrating another example of the constitution of the electrostatic capacitance-type input device of the present invention.

In addition, FIG. 9 which illustrates an X-Y cross section in FIG. 3 described below is also, similarly, a cross-sectional view illustrating a preferred constitution of the electrostatic capacitance-type input device of the present invention. FIG. 9 illustrates an aspect in which the electrostatic capacitance-type input device 10 is constituted of the substrate 1, the transparent film 11 having a refractive index of 1.6 to 1.78 and a thickness of 55 to 110 nm, the first electrode pattern 3 (only a pad portions 3*a* is illustrated in FIG. 9), the second transparent electrode pattern 4, the second photosensitive resin layer 12, and the photosensitive resin layer 7.

For the substrate 1, the material exemplified as the material of the electrode pattern in the laminate of the present invention can be used. In addition, in FIG. 1, a side of the substrate 1 on which the respective elements are provided is referred to as the noncontact surface side. In the electrostatic capacitance-type input device 10 of the present invention, input is carried out by bringing a finger or the like into contact with a contact surface (a surface opposite to the noncontact surface) of the substrate 1.

In addition, on the noncontact surface side of the substrate 1, the mask layer 2 is provided. The mask layer 2 is a trim-shaped pattern around a display region formed on the noncontact surface side of a touch panel substrate and is formed in order to prevent the guidance wire and the like from being visible.

Figure 2:
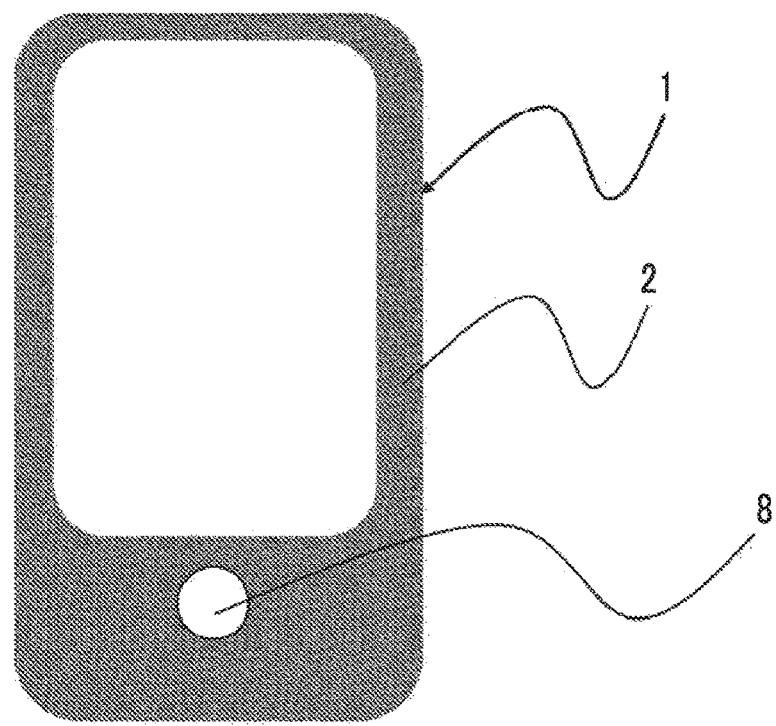
FIG. 2 is an explanatory view illustrating an example of a substrate in the present invention.

In the electrostatic capacitance-type input device 10 of the present invention, the mask layer 2 is provided so as to cover a part of a region (a region other than the input surface in FIG. 2) of the substrate 1 as illustrated in FIG. 2. Furthermore, an opening portion 8 can be provided in a part of the substrate 1 as illustrated in FIG. 2. In the opening portion 8, a press-type mechanical switch can be installed.

In FIG. 1, on the noncontact surface of the substrate 1, a plurality of first electrode patterns 3 (what is illustrated in FIG. 1 is the connection portion 3*b* of the first transparent electrode pattern) in which a plurality of the pad portions is formed so as to extend in the first direction through the connection portions, a plurality of second electrode patterns 4 which is electrically insulated from the first electrode pattern 3 and is made of a plurality of pad portions formed so as to extend in a direction orthogonal to the first direction, and the insulating layer 5 that electrically insulates the first electrode pattern 3 and the second electrode pattern 4 are formed. For the first electrode pattern 3, the second electrode pattern 4, and the additional conductive element 6 described below, the materials exemplified as the material of the electrode pattern in the laminate of the present invention can be used.

At least one of the first electrode pattern 3 or the second electrode pattern 4 can be installed so as to astride both regions of the noncontact surface of the transparent substrate 1 and the surface of the mask layer 2 opposite to the substrate 1. FIG. 1 illustrates a view in which the second electrode pattern 4 is installed so as to astride both regions of the noncontact surface of the substrate 1 and the surface of the mask layer 2 opposite to the substrate 1.

As described above, even in a case in which a photosensitive film is laminated so as to astride the mask layer which requires a certain thickness and the noncontact surface of the substrate (the rear surface of the contact surface), in a case in which a photosensitive film having a specific layer constitution described below is used, lamination causing no generation of foam in the boundary with the mask portion becomes possible with a simple step without using an expensive facility such as a vacuum laminator.

The first electrode pattern 3 and the second electrode pattern 4 will be described using FIG. 3. FIG. 3 is an explanatory view illustrating an example of the first electrode pattern and the second electrode pattern in the present invention. As illustrated in FIG. 3, in the first electrode pattern 3, the pad portions 3a are formed so as to extend in the first direction C through the connection portion 3b. In addition, the second electrode pattern 4 is electrically insulated from the first electrode pattern 3 using the insulating layer 5 and is constituted of a plurality of the pad portions formed so as to extend in a direction orthogonal to the first direction (a second direction D in FIG. 3). Here, in a case in which the first electrode pattern 3 is formed, the pad portions 3a and the connection portions 3b may be integrally produced or it is also possible to produce the connection portions 3b alone and integrally produce (pattern) the pad portions 3a and the second electrode pattern 4. In a case in which the pad portions 3a and the second electrode pattern 4 are integrally produced (patterned), the respective layers are formed so that some of the connection portions 3b and some of the pad portions 3a are coupled together as illustrated in FIG. 3 and the first electrode pattern 3 and the second electrode pattern 4 are electrically insulated from each other using the insulating layer 5.

In addition, in FIG. 3, a region in which the first electrode pattern 3, the second electrode pattern 4, and the additional conductive element 6 described below are not formed corresponds to the non-patterned region 22 in the laminate of the present invention.

In FIG. 1, the additional conductive element 6 is installed on the surface side of the mask layer 2 opposite to the substrate 1. The additional conductive element 6 is electrically connected to at least one of the first electrode pattern 3 (what is illustrated in FIG. 1 is a connection portion 3b of the first transparent electrode pattern) or the second electrode pattern 4 and is a separate element from the first electrode pattern 3 and the second electrode pattern 4.

FIG. 1 illustrates an aspect in which the additional conductive element 6 is connected to the second electrode pattern 4.

In addition, in FIG. 1, the photosensitive resin layer 7 is installed so as to cover all of the respective constituent elements. The photosensitive resin layer 7 may be constituted so as to cover only part of the respective constituent elements. The insulating layer 5 and the photosensitive resin layer 7 may be made of the same material or different materials. As the material constituting the insulating layer 5, it is possible to preferably use the material exemplified as the material of the photosensitive resin layer in the laminate of the present invention.

<Method for Manufacturing Electrostatic Capacitance-Type Input Device>

Figure 4:
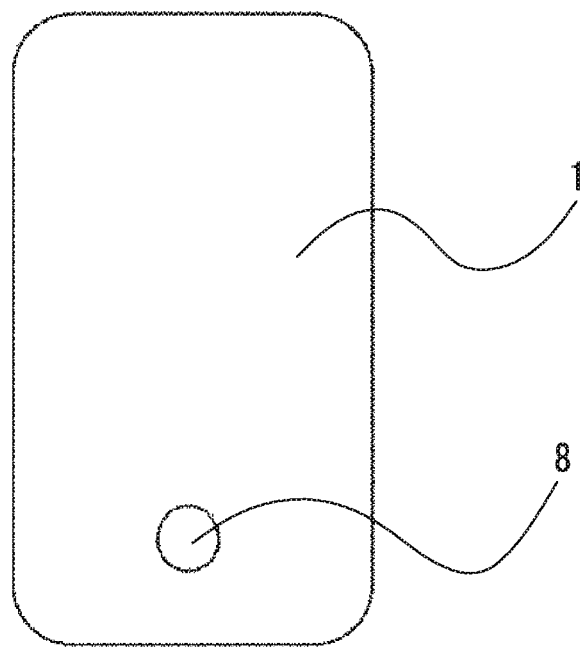
FIG. 4 is a top view illustrating an example of the substrate in which an opening portion is formed.
Figure 5:
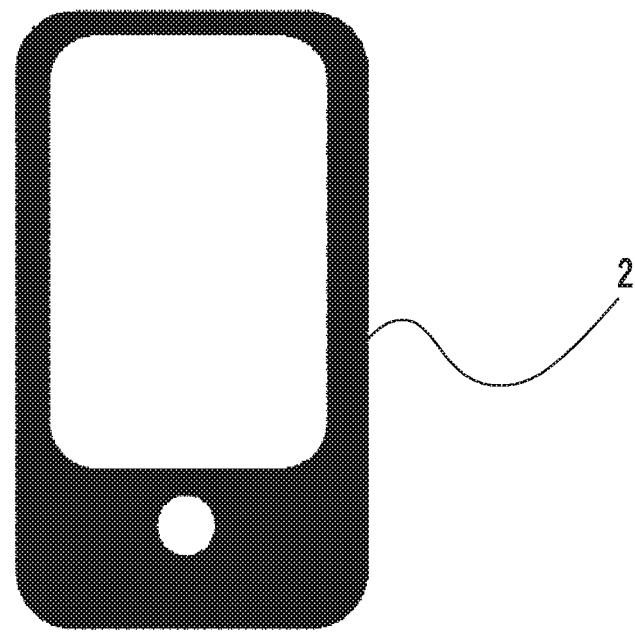
FIG. 5 is a top view illustrating an example of the substrate on which a mask layer is formed.
Figure 6:
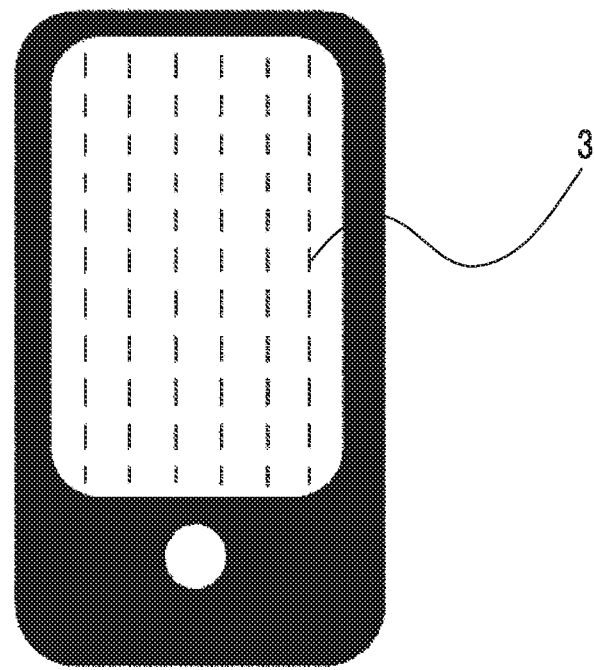
FIG. 6 is a top view illustrating an example of the substrate on which a first electrode pattern is formed.
Figure 7:
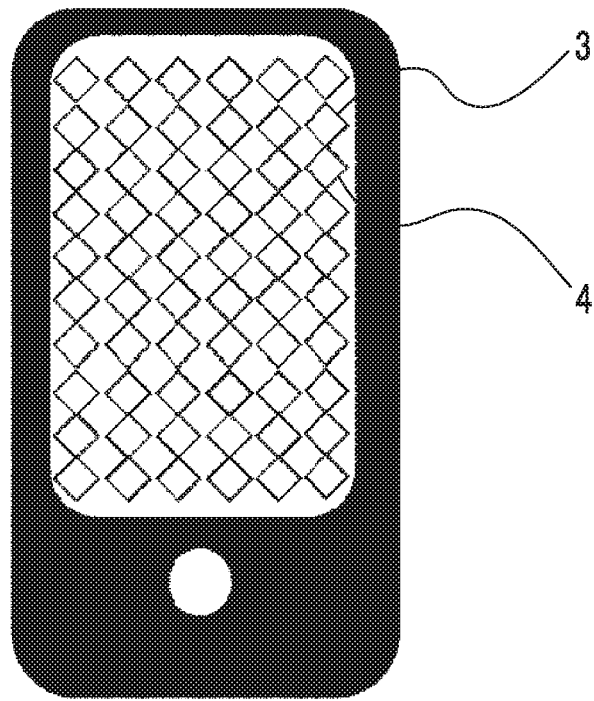
FIG. 7 is a top view illustrating an example of the substrate on which the first electrode pattern and a second electrode pattern are formed.
Figure 8:
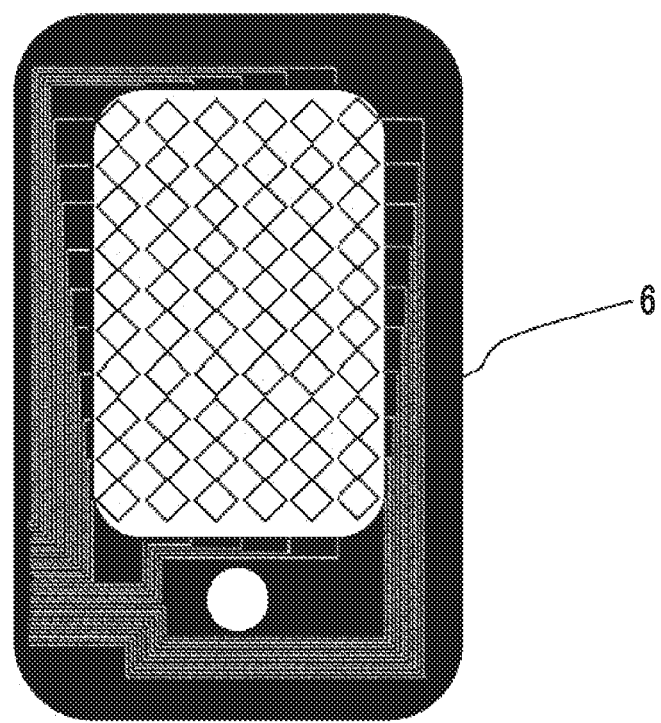
FIG. 8 is a top view illustrating an example of the substrate on which a conductive element different from the first and second electrode patterns is formed.

Examples of an aspect being formed in a process for manufacturing the electrostatic capacitance-type input device of the present invention include aspects of FIGS. 4 to 8. FIG. 4 is a top view illustrating an example of the transparent substrate 1 in which the opening portion 8 is formed and which is made of reinforced glass. FIG. 5 is a top view illustrating an example of the substrate in which the mask layer 2 is formed. FIG. 6 is a top view illustrating an example of the substrate in which the first electrode pattern 3 is formed. FIG. 7 is a top view illustrating an example of the substrate in which the first electrode pattern 3 and the second electrode pattern 4 are formed. FIG. 8 is a top view illustrating an example of the substrate in which the conductive element 6 other than the first and second electrode patterns is formed. These aspects illustrate examples in which the following description is specified, and the scope of the present invention is not interpreted to be limited by these drawings.

In a method for manufacturing the electrostatic capacitance-type input device, in a case in which the second photosensitive resin layer 12 and the photosensitive resin layer 7 are formed, the layers can be formed by transferring the second photosensitive resin layer and the photosensitive resin layer onto the surface of the substrate 1 on which the respective elements are arbitrarily formed using the transfer film of the present invention.

In the method for manufacturing the electrostatic capacitance-type input device, at least one element of the mask layer 2, the first electrode pattern 3, the second electrode pattern 4, the insulating layer 5, or the additional conductive element 6 is preferably formed using the photosensitive film having the temporary support and the photosensitive resin layer in this order.

In a case in which the respective elements (at least one element of the mask layer 2, the first electrode pattern 3, the second electrode pattern 4, the insulating layer 5, and the additional conductive element 6) are formed using the transfer film of the present invention or the photosensitive film, even in the substrate having the opening portion, resist components do not leak and/or protrude through the opening portion, and, particularly, in the mask layer in which a light-blocking pattern needs to be formed up to immediately above the boundary line of the edge portion of the substrate, resist components do not leak and/or protrude from the edge portion of the substrate. Therefore, the noncontact surface side of the substrate is not contaminated, and it is possible to manufacture touch panels having a reduced thickness and a reduced weight with simple steps.

In a case in which the mask layer, the insulating layer, and the conductive photosensitive resin layer are used, in a case in which the permanent materials of the first electrode pattern, the second electrode pattern, the additional conductive element, and the like are formed using the photosensitive film, the photosensitive film may be laminated on the substrate and then be pattern-exposed as necessary. The photosensitive film may be a negative-type material or a positive-type material. The non-exposed portions in a case in which the photosensitive film is a negative-type material or the exposed portions in the case of a positive-type material are removed by means of a development treatment, whereby patterns can be obtained. In the development, the thermoplastic resin layer and the photosensitive resin layer may be developed and removed using separate fluids or may be removed using the same fluid. Well-known development facilities such as a brush and a high-pressure jet may be combined together as necessary. After the development, post exposure and/or post baking may be carried out as necessary.

(Photosensitive Film)

The photosensitive film other than the transfer film of the present invention which is preferably used to manufacture the electrostatic capacitance-type input device of the present invention is described in [0222] to [0255] of JP2014-178922A, the content of which is incorporated herein by reference.

[Image Display Device]

An image display device of the present invention has the electrostatic capacitance-type input device of the present invention.

To the electrostatic capacitance-type input device of the present invention and image display devices having this electrostatic capacitance-type input device, it is possible to apply the constitution disclosed by "Advanced touch panel technology" (published by Techno Times Co., Ltd. on Jul. 6, 2009), "Technology and development of touch panels" edited by Yuji Mitani, CMC Publishing Co., Ltd. (December 2004), FPD International 2009 Forum T-11 lecture textbook, Cypress Semiconductor Corporation application note AN2292, and the like.

EXAMPLES

Hereinafter, the present invention will be more specifically described using examples. Materials, amounts used, ratios, processing contents, processing orders, and the like described in the following examples can be appropriately modified within the scope of the gist of the present invention. Therefore, the scope of the present invention is not limited to specific examples described below. Meanwhile, unless particularly otherwise described, "parts" and "%" are mass-based.

Examples 1 to 10 and Comparative Examples 1 to 9

[Preparation of Composition for Electrode Protective Film of Electrostatic Capacitance-Type Input Device]

Material-1 to Material-14 which were compositions for an electrode protective film of an electrostatic capacitance-type input device were prepared so as to obtain compositions shown in Tables 1 and 2.

| | Material | Weight-average molecular weight per ethylenic unsaturated group | Material-1 | Material-2 | Material-3 |
|---|---|---|---|---|---|
| (d) Compound capable of reacting with acidic groups or alcoholic hydroxy groups by heating | Compound 1 | — | 2.9 | 0.00 | 0.00 |
| | Compound 2 | — | 0.00 | 2.8 | 0.00 |
| | DURANATE TPA-B80E (manufactured by Asahi Kasei Corporation: non-volatile component: 80%) | — | 0.00 | 0.00 | 3.1 |
| (b) Photopolymerizable compound | A-BPEF (manufactured by Shin-Nakamura Chemical Co., Ltd.) | 278 | 0.00 | 0.00 | 0.00 |
| | DA-250 (Nagase ChemteX Corporation) | 248 | 0.00 | 0.00 | 0.00 |
| | A-600 (manufactured by Shin-Nakamura Chemical Co., Ltd.) | 354 | 2.7 | 0.00 | 0.00 |
| | A-GLY-9E (manufactured by Shin-Nakamura Chemical Co., Ltd.) | 217 | 0.00 | 3.1 | 0.00 |
| | UF-8001G (manufactured by Kyoeisha Chemical Co., Ltd.) | 2250 | 0.00 | 0.00 | 6.1 |
| | UA-160TM (manufactured by Shin-Nakamura Chemical Co., Ltd.) | 800 | 0.00 | 0.00 | 0.00 |
| | UA-122P (manufactured by Shin-Nakamura Chemical Co., Ltd.) | 550 | 0.00 | 0.00 | 0.00 |
| | DPHA liquid (dipentaerythritol hexaacrylate: 38%, dipentaerythritol pentaacrylate: 38%, 1-methoxy-2-propyl acetate: 24%) | 96 | 4.50 | 0.00 | 0.00 |
| | NK OLIGOMER UA-32P manufactured by Shin-Nakamura Chemical Co., Ltd., nonvolatile component: 75%, 1-methoxy-2-propyl acetate: 25% | 169 | 0.00 | 0.00 | 0.00 |
| | Monomer mixture (the photopolymerizable compound (b2-1) described in Paragraph [0111] of JP2012-78528A, n = 1: the content ratio of tripentaerythritol octaacrylate: 85%, the sum of n = 2 and n = 3 as impurities: 15%) | 95 | 1.50 | 1.90 | 0.00 |
| | Tetraacrylate of pentaerythritol ethylene oxide adduct (KAYARAD RP-1040 manufactured by Nippon Kayaku Co., Ltd.) | 132 | 0.00 | 0.00 | 0.00 |
| | Tricyclodecane dimethanol diacrylate (A-DCP, manufactured by Shin-Nakamura Chemical Co., Ltd.) | 168 | 0.00 | 7.50 | 6.60 |
| | Polyethylene glycol #200 diacrylate (A-200, manufactured by Shin-Nakamura Chemical Co., Ltd.) | 77 | 0.00 | 0.00 | 0.00 |
| | Ethoxylated isocyanuric acid triacrylate (A-9300 manufactured by Shin-Nakamura Chemical Co., Ltd.) | 184 | 0.00 | 0.00 | 0.00 |
| | Urethane acrylate U-15HA (manufactured by Shin-Nakamura Chemical Co., Ltd.) | 153 | 0.00 | 0.00 | 0.00 |
| | ARONIX M-310 (manufactured by Toagosei Co,. Ltd.) | 157 | 3.15 | 1.83 | 3.31 |
| (a) Binder polymer | Polymer solution 1 (Structural Formula P-25 described in [0058] of JP2008-146018A: the weight-average molecular weight = 35,000, solid content: 45%, 1-methoxy-2-propyl acetate: 15%, 1-methoxy-2-propanol: 40%) | — | 43.80 | 42.90 | 40.50 |
| | Polymer solution 2 (copolymer of methacrylic acid/methyl methacrylate/butyl methacrylate: molecular weight: 60,000, compositional ratio = 30/30/40, non-volatile component: 45%, 1-methoxy-2-propylacetate: 55%) | — | 0.00 | 0.00 | 0.00 |
| | BONRON XPS001 (manufactured by Mitsui Chemicals, Inc.) | — | 0.00 | 0.00 | 0.00 |
| (c) Photopolymerization initiator | Photoradical photopolymerization initiator: 2-benzyl-2-dimethylamino-1-(4-morpholinophenyl)-butanone (IRGACURE 379, manufactured by BASF) | — | 0.36 | 0.00 | 0.00 |
| | Photoradical polymerization initiator: 1,2-octane dione, 1-[4-(phenylthio)-, 2-(O-benzoyloxime)] (IRGACURE OXE-01, manufactured by BASF) | — | 0.00 | 0.61 | 0.61 |
| | Photopolymerization initiator: KAYACURE DETX-S (alkylthioxanthone manufactured by Nippon Kayaku Co., Ltd.) | — | 0.36 | 0.00 | 0.00 |

-continued

| | | | | | |
|---|---|---|---|---|---|
| Additive | Polymer solution 3 (the following structural formula, weight-average molecular weight: 15,000, nonvolatile content: 30% by mass, methyl ethyl ketone: 70% by mass) | — | 0.03 | 0.03 | 0.03 |
| Solvent | 1-Methoxy-2-propyl acetate | — | 0.00 | 3.09 | 23.41 |
| | Methyl ethyl ketone | — | 40.7 | 36 | 16 |
| | Total solid content (sum) | | 34.10 | 35.22 | 34.02 |
| | Ratio of photopolymerizable compound in which value obtained by dividing weight-average molecular weight by average number of polymerizable groups is 270 or more to all of (b) photopolymerizable compound (% by mass) | | 25.07 | 21.63 | 38.10 |
| | Ratio of photopolymerizable compound in which value obtained by dividing weight-average molecular weight by average number of polymerizable groups is 270 or more to total solid content (% by mass) | | 7.92 | 8.80 | 17.93 |
| | Total (parts by mass) | | 100 | 100 | 100 |

| | Material | Weight-average molecular weight per ethylenic unsaturated group | Material-4 | Material-5 |
|---|---|---|---|---|
| (d) Compound capable of reacting with acidic groups or alcoholic hydroxy groups by heating | Compound 1 | — | 0.00 | 0.00 |
| | Compound 2 | — | 0.00 | 0.00 |
| | DURANATE TPA-B80E (manufactured by Asahi Kasei Corporation: non-volatile component: 80%) | — | 3.1 | 0.00 |
| (b) Photopolymerizable compound | A-BPEF (manufactured by Shin-Nakamura Chemical Co., Ltd.) | 278 | 0.00 | 0.00 |
| | DA-250 (Nagase ChemteX Corporation) | 248 | 0.00 | 0.00 |
| | A-600 (manufactured by Shin-Nakamura Chemical Co., Ltd.) | 354 | 0.00 | 0.00 |
| | A-GLY-9E (manufactured by Shin-Nakamura Chemical Co., Ltd.) | 432 | 0.00 | 0.00 |
| | UF-8001G (manufactured by Kyoeisha Chemical Co., Ltd.) | 2250 | 0.00 | 0.00 |
| | UA-160TM (manufactured by Shin-Nakamura Chemical Co., Ltd.) | 800 | 3.8 | 0.00 |
| | UA-122P (manufactured by Shin-Nakamura Chemical Co., Ltd.) | 550 | 3.5 | 0.00 |
| | DPHA liquid (dipentaerythritol hexaacrylate: 38%, dipentaerythritol pentaacrylate: 38%, 1-methoxy-2-propyl acetate: 24%) | 96 | 0.00 | 5.80 |
| | NK OLIGOMER UA-32P manufactured by Shin-Nakamura Chemical Co., Ltd., nonvolatile component: 75%, 1-methoxy-2-propyl acetate: 25% | 169 | 0.00 | 0.00 |
| | Monomer mixture (the photopolymerizable compound (b2-1) described in Paragraph [0111] of JP2012-78528A, n = 1: the content ratio of tripentaerythritol octaacrylate: 85%, the sum of n = 2 and n = 3 as impurities: 15%) | 95 | 0.00 | 7.30 |
| | Tetraacrylate of pentaerythritol ethylene oxide adduct (KAYARAD RP-1040 manufactured by Nippon Kayaku Co., Ltd.) | 132 | 0.00 | 0.00 |
| | Tricyclodecane dimethanol diacrylate (A-DCP, manufactured by Shin-Nakamura Chemical Co., Ltd.) | 168 | 6.20 | 0.00 |
| | Polyethylene glycol #200 diacrylate (A-200, manufactured by Shin-Nakamura Chemical Co., Ltd.) | 77 | 0.00 | 0.00 |
| | Ethoxylated isocyanuric acid triacrylate (A-9300 manufactured by Shin-Nakamura Chemical Co., Ltd.) | 184 | 0.00 | 0.00 |
| | Urethane acrylate U-15HA (manufactured by Shin-Nakamura Chemical Co., Ltd.) | 153 | 0.00 | 0.00 |
| | ARONIX M-310 (manufactured by Toagosei Co,. Ltd.) | 157 | 2.95 | 2.24 |
| (a) Binder polymer | Polymer solution 1 (Structural Formula P-25 described in [0058] of JP2008-146018A: the weight-average molecular weight = 35,000, solid content: 45%, 1-methoxy-2-propyl acetate: 15%, 1-methoxy-2-propanol: 40%) | — | 38.70 | 35.30 |
| | Polymer solution 2 (copolymer of methacrylic acid/methyl methacrylate/butyl methacrylate: molecular weight: 60,000, compositional ratio = 30/30/40, non-volatile component: 45%, 1-methoxy-2-propylacetate: 55%) | — | 0.00 | 0.00 |
| | BONRON XPS001 (manufactured by Mitsui Chemicals, Inc.) | — | 0.00 | 0.00 |
| (c) Photopolymerization initiator | Photoradical photopolymerization initiator: 2-benzyl-2-dimethylamino-1-(4-morpholinophenyl)-butanone (IRGACURE 379, manufactured by BASF) | — | 0.00 | 0.00 |
| | Photoradical polymerization initiator: 1,2-octane dione, 1-[4-(phenylthio)-, 2-(O-benzyloxime)] (IRGACURE OXE-01, manufactured by BASF) | — | 0.61 | 0.61 |
| | Photopolymerization initiator: KAYACURE DETX-S (alkylthioxanthone manufactured by Nippon Kayaku Co., Ltd.) | — | 0.00 | 0.00 |
| Additive | Polymer solution 3 (the following structural formula, weight-average molecular weight: 15,000, nonvolatile content: 30% by mass, methyl ethyl ketone: 70% by mass) | — | 0.03 | 0.03 |

-continued

| | | | | |
|---|---|---|---|---|
| Solvent | 1-Methoxy-2-propyl acetate | | 2.07 | 10.68 |
| | Methyl ethyl ketone | — | 39 | 38 |

| | | |
|---|---|---|
| Total solid content (sum) | 34.01 | 28.21 |
| Ratio of photopolymerizable compound in which value obtained by dividing weight-average molecular weight by average number of polymerizable groups is 270 or more to all of (b) photopolymerizable compound (% by mass) | 44.38 | 0.00 |
| Ratio of photopolymerizable compound in which value obtained by dividing weight-average molecular weight by average number of polymerizable groups is 270 or more to total solid content (% by mass) | 21.46 | 0.00 |
| Total (parts by mass) | 100 | 100 |

| | Material | Weight-average molecular weight per ethylenic unsaturated group | Material-6 | Material-7 |
|---|---|---|---|---|
| (d) Compound capable of reacting with acidic groups or alcoholic hydroxy groups by heating | Compound 1 | — | 0.00 | 0.00 |
| | Compound 2 | — | 0.00 | 0.00 |
| | DURANATE TPA-B80E (manufactured by Asahi Kasei Corporation: non-volatile component: 80%) | — | 0.00 | 0.00 |
| (b) Photopolymerizable compound | A-BPEF (manufactured by Shin-Nakamura Chemical Co., Ltd.) | 278 | 0.00 | 0.00 |
| | DA-250 (Nagase ChemteX Corporation) | 248 | 0.00 | 0.00 |
| | A-600 (manufactured by Shin-Nakamura Chemical Co., Ltd.) | 354 | 0.00 | 0.00 |
| | A-GLY-9E (manufactured by Shin-Nakamura Chemical Co., Ltd.) | 432 | 0.00 | 0.00 |
| | UF-8001G (manufactured by Kyoeisha Chemical Co., Ltd.) | 2250 | 0.00 | 0.00 |
| | UA-160TM (manufactured by Shin-Nakamura Chemical Co., Ltd.) | 800 | 0.00 | 0.00 |
| | UA-122P (manufactured by Shin-Nakamura Chemical Co., Ltd.) | 550 | 0.00 | 0.00 |
| | DPHA liquid (dipentaerythritol hexaacrylate: 38%, dipentaerythritol pentaacrylate: 38%, 1-methoxy-2-propyl acetate: 24%) | 96 | 5.47 | 0.00 |
| | NK OLIGOMER UA-32P manufactured by Shin-Nakamura Chemical Co., Ltd., nonvolatile component: 75%, 1-methoxy-2-propyl acetate: 25% | 169 | 3.50 | 0.00 |
| | Monomer mixture (the photopolymerizable compound (b2-1) described in Paragraph [0111] of JP2012-78528A, n = 1: the content ratio of tripentaerythritol octaacrylate: 85%, the sum of n = 2 and n = 3 as impurities: 15%) | 95 | 0.00 | 0.00 |
| | Tetraacrylate of pentaerythritol ethylene oxide adduct (KAYARAD RP-1040 manufactured by Nippon Kayaku Co., Ltd.) | 132 | 4.13 | 0.00 |
| | Tricyclodecane dimethanol diacrylate (A-DCP, manufactured by Shin-Nakamura Chemical Co., Ltd.) | 168 | 0.00 | 8.31 |
| | Polyethylene glycol #200 diacrylate (A-200, manufactured by Shin-Nakamura Chemical Co., Ltd.) | 77 | 0.00 | 0.00 |
| | Ethoxylated isocyanuric acid triacrylate (A-9300 manufactured by Shin-Nakamura Chemical Co., Ltd.) | 184 | 0.00 | 0 |
| | Urethane acrylate U-15HA (manufactured by Shin-Nakamura Chemical Co., Ltd.) | 153 | 0.00 | 2.52 |
| | ARONIX M-310 (manufactured by Toagosei Co,. Ltd.) | 157 | 2.16 | 0.00 |
| (a) Binder polymer | Polymer solution 1 (Structural Formula P-25 described in [0058] of JP2008-146018A: the weight-average molecular weight = 35,000, solid content: 45%, 1-methoxy-2-propyl acetate: 15%, 1-methoxy-2-propanol: 40%) | — | 39.20 | 0.00 |
| | Polymer solution 2 (copolymer of methacrylic acid/methyl methacrylate/butyl methacrylate: 60,000, compositional ratio = 30/30/40, non-volatile component: 45%, 1-methoxy-2-propylacetate: 55%) | — | 0.00 | 0.00 |
| | BONRON XPS001 (manufactured by Mitsui Chemicals, Inc.) | — | 0.00 | 20.30 |
| (c) Photopolymerization initiator | Photoradical photopolymerization initiator: 2-benzyl-2-dimethylamino-1-(4-morpholinophenyl)-butanone (IRGACURE 379, manufactured by BASF) | — | 0.00 | 0.00 |
| | Photoradical polymerization initiator: 1,2-octane dione, 1-[4-(phenylthio)-, 2-(O-benzoyloxime)] (IRGACURE OXE-01, manufactured by BASF) | — | 0.61 | 0.61 |
| | Photopolymerization initiator: KAYACURE DETX-S (alkylthioxanthone manufactured by Nippon Kayaku Co., Ltd.) | — | 0.00 | 0.00 |
| Additive | Polymer solution 3 (the following structural formula, weight-average molecular weight: 15,000, nonvolatile content: 30% by mass, methyl ethyl ketone: 70% by mass) | — | 0.03 | 0.03 |

-continued

| | | | | |
|---|---|---|---|---|
| Solvent | 1-Methoxy-2-propyl acetate | — | 27.03 | 30.36 |
| | Methyl ethyl ketone | — | 18 | 38 |
| | Total solid content (sum) | | 29.17 | 31.74 |
| | Ratio of photopolymerizable compound in which value obtained by dividing weight-average molecular weight by average number of polymerizable groups is 270 or more to all of (b) photopolymerizable compound (% by mass) | | 0.00 | 0.00 |
| | Ratio of photopolymerizable compound in which value obtained by dividing weight-average molecular weight by average number of polymerizable groups is 270 or more to total solid content (% by mass) | | 0.00 | 0.00 |
| | Total (parts by mass) | | 100 | 100 |

| | Material | Weight-average molecular weight per ethylenic unsaturated group | Material-8 | Material-9 | Material-10 |
|---|---|---|---|---|---|
| (d) Compound capable of reacting with acidic groups or alcoholic hydroxy groups by heating | Compound 1 | — | 0.00 | 0.00 | 2.9 |
| | Compound 2 | — | 0.00 | 0.00 | 0.00 |
| | DURANATE TPA-B80E (manufactured by Asahi Kasei Corporation: non-volatile component: 80%) | — | 0.00 | 0.00 | 0.00 |
| (b) Photopolymerizable compound | A-BPEF (manufactured by Shin-Nakamura Chemical Co., Ltd.) | 278 | 0.00 | 0.00 | 5.51 |
| | DA-250 (Nagase ChemieX Corporation) | 248 | 0.00 | 0.00 | 0.00 |
| | A-600 (manufactured by Shin-Nakamura Chemical Co., Ltd.) | 354 | 0.00 | 0.00 | 0.00 |
| | A-GLY-9E (manufactured by Shin-Nakamura Chemical Co., Ltd.) | 217 | 3.1 | 0.00 | 0.00 |
| | UF-8001G (manufactured by Kyoeisha Chemical Co. Ltd.) | 2250 | 0.00 | 6.1 | 0.00 |
| | UA-160TM (manufactured by Shin-Nakamura Chemical Co., Ltd.) | 800 | 0.00 | 0.00 | 0.00 |
| | UA-122P (manufactured by Shin-Nakamura Chemical Co., Ltd.) | 550 | 0.00 | 0.00 | 0.00 |
| | DPHA liquid (dipentaerythritol hexaacrylate: 38%, dipentaerythritol pentaacrylate: 38%, 1-methoxy-2-propyl acetate: 24%) | 96 | 0.00 | 0.00 | 0.00 |
| | NK OLIGOMER UA-32P, manufactured by Shin-Nakamura Chemical Co., Ltd., nonvolatile component: 75%, 1-methoxy-2-propyl acetate: 25% | 169 | 0.00 | 0.00 | 0.00 |
| | Monomer mixture (the photopolymerizable compound (b2-1). described in Paragraph [0111] of JP2012-78528A, n = 1: the content ratio of tripentaerythritol octaacrylate: 85%, the sum of n = 2 and n = 3 as impurities: 15%) | 95 | 0.00 | 0.00 | 0.00 |
| | Tetraacrylate of pentaerythritol ethylene oxide adduct (KAYARAD RP-1040 manufactured by Nippon Kayaku Co., Ltd.) | 132 | 0.00 | 0.00 | 0.00 |
| | Tricyclodecane dimethanol diacrylate (A-DCP, manufactured by Shin-Nakamura Chemical Co., Ltd.) | 168 | 6.50 | 5.31 | 8.31 |
| | Polyethylene glycol #200 diacrylate (A-200, manufactured by Shin-Nakamura Chemical Co., Ltd.) | 77 | 0.00 | 0.00 | 0.00 |
| | Ethoxylated isocyanuric acid triacrylate (A-9300 manufactured by Shin-Nakamura Chemical Co., Ltd.) | 184 | 0 | 0 | 0.00 |
| | Urethane acrylate U-15HA (manufactured by Shin-Nakamura Chemical Co., Ltd.) | 153 | 2.90 | 6.80 | 0.00 |
| | ARONIX M-310 (manufactured by Toagosei Co., Ltd.) | 157 | 0.00 | 0.00 | 0.00 |
| (a) Binder polymer | Polymer solution 1 (Structural Formula P-25 described in [0058] of JP2008-146018A: the weight-average molecular weight = 35,000, solid content: 45%, 1-methoxy-2-propyl acetate: 15%, 1-methoxy-2-propanol: 40%) | — | 34.00 | 31.50 | 36.00 |
| | Polymer solution 2 (copolymer of methacrylic acid/methyl methacrylate/butyl methacrylate: molecular weight: 60,000, compositional ratio = 30/30/40, non-volatile component: 45%, 1-methoxy-2-propylacetate: 55%) | — | 0.00 | 0.00 | 0.00 |
| | BONRON XPS001 (manufactured by Mitsui Chemicals, Inc.) | — | 0.00 | 0.00 | 0.00 |
| (c) Photopolymerization initiator | Photoradical photopolymerization initiator: 2-benzyl-2-dimethylamino-1-(4-morpholinophenyl)-butanone (IRGACURE 379, manufactured by BASF) | — | 0.36 | 0.00 | 0.00 |
| | Photoradical polymerization initiator: 1,2-octane dione, 1-[4-(phenylthio)-, 2-(O-benzoyloxime)] (IRGACURE OXE-01, manufactured by BASF) | — | 0.00 | 0.61 | 0.21 |
| | Photopolymerization initiator: KAYACURE DETX-S (alkylthioxanthone manufactured by Nippon Kayaku Co., Ltd.) | — | 0.36 | 0.00 | 0.00 |
| Additive | Polymer solution 3 (the following structural formula, weight-average molecular weight: 15,000, nonvolatile content: 30% by mass, methyl ethyl ketone: 70% by mass) | — | 0.03 | 0.03 | 0.03 |

-continued

| Solvent | 1-Methoxy-2-propyl acetate | — | 15.98 | 11.88 | 20.53 |
| | Methyl ethyl ketone | — | 37 | 38 | 27 |
| | Total solid content (sum) | | 28.52 | 33.00 | 27.62 |
| | Ratio of photopolymerizable compound in which value obtained by dividing weight-average molecular weight by average number of polymerizable groups is 270 or more to all of (b) photopolymezable compound (% by mass) | | 24.80 | 33.50 | 39.87 |
| | Ratio of photopolymerizable compound in which value obtained by dividing weight-average molecular weight by average number of polymerizable groups is 270 or more to total solid content (% by mass) | | 10.87 | 18.49 | 19.95 |
| | Total (parts by mass) | | 100 | 100 | 100 |

| | Material | Weight-average molecular weight per ethylenic unsaturated group | Material-11 | Material-12 |
|---|---|---|---|---|
| (d) Compound capable of reacting with acidic groups or alcoholic hydroxy groups by heating | Compound 1 | — | 0.00 | 0.00 |
| | Compound 2 | — | 2.8 | 0.00 |
| | DURANATE TPA-B80E (manufactured by Asahi Kasei Corporation: non-volatile component: 80%) | — | 0.00 | 3.1 |
| (b) Photopolymerizable compound | A-BPEF (manufactured by Shin-Nakamura Chemical Co., Ltd.) | 278 | 0.00 | 0.00 |
| | DA-250 (Nagase ChemieX Corporation) | 248 | 0.00 | 0.00 |
| | A-600 (manufactured by Shin-Nakamura Chemical Co., Ltd.) | 354 | 0.00 | 0.00 |
| | A-GLY-9E (manufactured by Shin-Nakamura Chemical Co., Ltd.) | 432 | 0.00 | 0.00 |
| | UF-8001G (manufactured by Kyoeisha Chemical Co. Ltd.) | 2250 | 0.00 | 0.00 |
| | UA-160TM (manufactured by Shin-Nakamura Chemical Co., Ltd.) | 800 | 0.00 | 0.00 |
| | UA-122P (manufactured by Shin-Nakamura Chemical Co., Ltd.) | 550 | 0.00 | 0.00 |
| | DPHA liquid (dipentaerythritol hexaacrylate: 38%, dipentaerythritol pentaacrylate: 38%, 1-methoxy-2-propyl acetate: 24%) | 96 | 5.70 | 0.00 |
| | NK OLIGOMER UA-32P, manufactured by Shin-Nakamura Chemical Co., Ltd., nonvolatile component: 75%, 1-methoxy-2-propyl acetate: 25% | 169 | 0.00 | 0.00 |
| | Monomer mixture (the photopolymerizable compound (b2-1). described in Paragraph [0111] of JP2012-78528A, n = 1: the content ratio of tripentaerythritol octaacrylate: 85%, the sum of n = 2 and n = 3 as impurities: 15%) | 95 | 0.00 | 3.80 |
| | Tetraacrylate of pentaerythritol ethylene oxide adduct (KAYARAD RP-1040 manufactured by Nippon Kayaku Co., Ltd.) | 132 | 9.35 | 0.00 |
| | Tricyclodecane dimethanol diacrylate (A-DCP, manufactured by Shin-Nakamura Chemical Co., Ltd.) | 168 | 0.00 | 0.00 |
| | Polyethylene glycol #200 diacrylate (A-200, manufactured by Shin-Nakamura Chemical Co., Ltd.) | 77 | 0.00 | 5.40 |
| | Ethoxylated isocyanuric acid triacrylate (A-9300 manufactured by Shin-Nakamura Chemical Co., Ltd.) | 184 | 0.00 | 0.00 |
| | Urethane acrylate U-15HA (manufactured by Shin-Nakamura Chemical Co., Ltd.) | 153 | 0 | 0.00 |
| | ARONIX M-310 (manufactured by Toagosei Co., Ltd.) | 157 | 1.10 | 1.10 |
| (a) Binder polymer | Polymer solution 1 (Structural Formula P-25 described in [0058] of JP2008-146018A: the weight-average molecular weight = 35,000, solid content: 45%, 1-methoxy-2-propyl acetate: 15%, 1-methoxy-2-propanol: 40%) | — | 34.00 | 0.00 |
| | Polymer solution 2 (copolymer of methacrylic acid/methyl methacrylate/butyl methacrylate: molecular weight: 60,000, compositional ratio = 30/30/40, non-volatile component: 45%, 1-methoxy-2-propylacetate: 55%) | — | 0.00 | 37.50 |
| | BONRON XPS001 (manufactured by Mitsui Chemicals, Inc.) | — | 0.00 | 0.00 |
| (c) Photopolymerization initiator | Photoradical photopolymerization initiator: 2-benzyl-2-dimethylamino-1-(4-morpholinophenyl)-butanone (IRGACURE 379, manufactured by BASF) | — | 0.00 | 0.00 |
| | Photoradical polymerization initiator: 1,2-octane dione, 1-[4-(phenylthio)-, 2-(O-benzoyloxime)] (IRGACURE OXE-01, manufactured by BASF) | — | 0.61 | 0.61 |
| | Photopolymerization initiator: KAYACURE DETX-S (alkylthioxanthone manufactured by Nippon Kayaku Co., Ltd.) | — | 0.00 | 0.00 |
| Additive | Polymer solution 3 (the following structural formula, weight-average molecular weight: 15,000, nonvolatile content: 30% by mass, methyl ethyl ketone: 70% by mass) | — | 0.03 | 0.03 |

-continued

| | | | | |
|---|---|---|---|---|
| Solvent | 1-Methoxy-2-propyl acetate | — | 13.04 | 32.84 |
| | Methyl ethyl ketone | — | 33 | 16 |
| | Total solid content (sum) | | 32.39 | 29.17 |
| | Ratio of photopolymerizable compound in which value obtained by dividing weight-average molecular weight by average number of polymerizable groups is 270 or more to all of (b) photopolymezable compound (% by mass) | | 0.00 | 0.00 |
| | Ratio of photopolymerizable compound in which value obtained by dividing weight-average molecular weight by average number of polymerizable groups is 270 or more to total solid content (% by mass) | | 0.00 | 0.00 |
| | Total (parts by mass) | | 100 | 100 |

| | Material | Weight-average molecular weight per ethylenic unsaturated group | Material-13 | Material-14 |
|---|---|---|---|---|
| (d) Compound capable of reacting with acidic groups or alcoholic hydroxy groups by heating | Compound 1 | — | 0.00 | 0.00 |
| | Compound 2 | — | 0.00 | 2.6 |
| | DURANATE TPA-B80E (manufactured by Asahi Kasei Corporation: non-volatile component: 80%) | — | 3.1 | 0.00 |
| (b) Photopolymerizable compound | A-BPEF (manufactured by Shin-Nakamura Chemical Co., Ltd.) | 278 | 0.00 | 0.00 |
| | DA-250 (Nagase ChemieX Corporation) | 248 | 0.00 | 8.31 |
| | A-600 (manufactured by Shin-Nakamura Chemical Co., Ltd.) | 354 | 0.00 | 0.00 |
| | A-GLY-9E (manufactured by Shin-Nakamura Chemical Co., Ltd.) | 432 | 0.00 | 0.00 |
| | UF-8001G (manufactured by Kyoeisha Chemical Co. Ltd.) | 2250 | 0.00 | 0.00 |
| | UA-160TM (manufactured by Shin-Nakamura Chemical Co., Ltd.) | 800 | 0.00 | 0.00 |
| | UA-122P (manufactured by Shin-Nakamura Chemical Co., Ltd.) | 550 | 0.00 | 0.00 |
| | DPHA liquid (dipentaerythritol hexaacrylate: 38%, dipentaerythritol pentaacrylate: 38%, 1-methoxy-2-propyl acetate: 24%) | 96 | 0.00 | 0.00 |
| | NK OLIGOMER UA-32P, manufactured by Shin-Nakamura Chemical Co., Ltd., nonvolatile component: 75%, 1-methoxy-2-propyl acetate: 25% | 169 | 0.00 | 0.00 |
| | Monomer mixture (the photopolymerizable compound (b2-1). described in Paragraph [0111] of JP2012-78528A, n = 1: the content ratio of tripentaerythritol octaacrylate: 85%, the sum of n = 2 and n = 3 as impurities: 15%) | 95 | 0.00 | 0.00 |
| | Tetraacrylate of pentaerythritol ethylene oxide adduct (KAYARAD RP-1040 manufactured by Nippon Kayaku Co., Ltd.) | 132 | 0.00 | 0.00 |
| | Tricyclodecane dimethanol diacrylate (A-DCP, manufactured by Shin-Nakamura Chemical Co., Ltd.) | 168 | 8.31 | 0.00 |
| | Polyethylene glycol #200 diacrylate (A-200, manufactured by Shin-Nakamura Chemical Co., Ltd.) | 77 | 0.00 | 0.00 |
| | Ethoxylated isocyanuric acid triacrylate (A-9300 manufactured by Shin-Nakamura Chemical Co., Ltd.) | 184 | 3.50 | 0.00 |
| | Urethane acrylate U-15HA (manufactured by Shin-Nakamura Chemical Co., Ltd.) | 153 | 0.00 | 0.00 |
| | ARONIX M-310 (manufactured by Toagosei Co., Ltd.) | 157 | 0.00 | 0.00 |
| (a) Binder polymer | Polymer solution 1 (Structural Formula P-25 described in [0058] of JP2008-146018A: the weight-average molecular weight = 35,000, solid content: 45%, 1-methoxy-2-propyl acetate: 15%, 1-methoxy-2-propanol: 40%) | — | 38.30 | 36.20 |
| | Polymer solution 2 (copolymer of methacrylic acid/methyl methacrylate/butyl methacrylate: molecular weight: 60,000, compositional ratio = 30/30/40, non-volatile component: 45%, 1-methoxy-2-propylacetate: 55%) | — | 0.00 | 0.00 |
| | BONRON XPS001 (manufactured by Mitsui Chemicals, Inc.) | — | 0.00 | 0.00 |
| (c) Photopolymerization initiator | Photoradical photopolymerization initiator: 2-benzyl-2-dimethylamino-1-(4-morpholinophenyl)-butanone (IRGACURE 379, manufactured by BASF) | — | 0.00 | 0.00 |
| | Photoradical polymerization initiator: 1,2-octane dione, 1-[4-(phenylthio)-, 2-(O-benzoyloxime)] (IRGACURE OXE-01, manufactured by BASF) | — | 0.58 | 0.58 |
| | Photopolymerization initiator: KAYACURE DETX-S (alkylthioxanthone manufactured by Nippon Kayaku Co., Ltd.) | — | 0.00 | 0.00 |
| Additive | Polymer solution 3 (the following structural formula, weight-average molecular weight: 15,000, nonvolatile content: 30% by mass, methyl ethyl ketone: 70% by mass) | — | 0.03 | 0.03 |

| | | | | |
|---|---|---|---|---|
| Solvent | 1-Methoxy-2-propyl acetate | — | 8.31 | 14.41 |
| | Methyl ethyl ketone | — | 38 | 38 |
| | Total solid content (sum) | | 32.11 | 19.47 |
| | Ratio of photopolymerizable compound in which value obtained by dividing weight-average molecular weight by average number of polymerizable groups is 270 or more to all of (b) photopolymezable compound (% by mass) | | 0.00 | 0.00 |
| | Ratio of photopolymerizable compound in which value obtained by dividing weight-average molecular weight by average number of polymerizable groups is 270 or more to total solid content (% by mass) | | 0.00 | 0.00 |
| | Total (parts by mass) | | 100 | 100 |

The details of materials used for Material-1 to Material-14 will be described below.

(Compound Capable of Reacting with Acidic Groups or Alcoholic Hydroxy Group by Heating)

Compound 1 has a structure represented by General Formula (1). Compound 2 has a structure represented by General Formula (1).

Compound 1 and Compound 2 which were compounds capable of reacting with acidic groups or alcoholic hydroxy groups by heating were synthesized using a method of Synthesis Example 1.

—Synthesis of Compound 1—

Hexamethylene diisocyanate (HDI, also referred to as 1,6-diisocyanatohexane) (600 parts) was prepared in a device obtained by substituting the inside of a four-neck flask equipped with a stirrer, a thermometer, and a cooling pipe with nitrogen, and the temperature in a reactor was held at 70° C. under stirring. Tetramethylammoniumcaprylate was added thereto as an isocyanuration catalyst, and phosphoric acid was added thereto when the yield reached 40% by mass, thereby stopping the reaction. After a reaction liquid was filtered, unreacted HDI was removed using a thin film evaporator. The obtained polyisocyanate was prepared and heated to 40° C., and methyl ethyl ketoxime having a molar quantity that was 1.05 times the molar quantity of —NCO contained in the polyisocyanate was gradually added thereto. After all of the methyl ethyl ketoxime was added thereto, the reaction liquid was heated to 60° C. and stirred for two hours. After it was confirmed that the absorption attributed to an isocyanate disappeared by means of Fourier-transform infrared spectroscopy (FT-IR), the stirring was stopped, and a blocked polyisocyanate composition was obtained. The obtained blocked polyisocyanate composition was considered as Compound 1.

—Synthesis of Compound 2—

1,6-Diisocyanatohexane (600 parts) was prepared in a device obtained by substituting the inside of a four-neck flask equipped with a stirrer, a thermometer, and a cooling pipe with nitrogen, and the temperature in a reactor was held at 70° C. under stirring. Tetramethylammoniumcaprylate was added thereto as an isocyanuration catalyst, and phosphoric acid was added thereto when the yield reached 40% by mass, thereby stopping the reaction. After a reaction liquid was filtered, unreacted HDI was removed using a thin film evaporator. The obtained polyisocyanate was prepared and heated to 80° C., and 3,5-dimethylpyrazole having a molar quantity that was 1.05 times the molar quantity of —NCO contained in the polyisocyanate was gradually added thereto. After all of the 3,5-dimethylpyrazole was added thereto, the reaction liquid was further stirred for two hours. After it was confirmed that the absorption attributed to an isocyanate disappeared by means of FT-IR, the stirring was stopped, and a blocked polyisocyanate composition was obtained. The obtained blocked polyisocyanate composition was considered as Compound 2.

(Additive)

As an additive, Polymer Solution 3 including a compound represented by the following structural formula was used. Meanwhile, "wt %" in the present specification is the same as "% by mass".

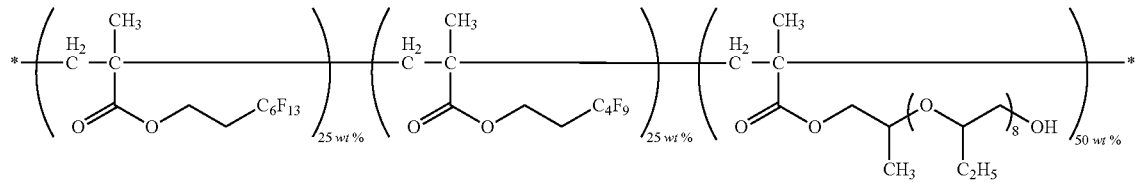

[Production of Transfer Film]

The application amount was adjusted so that the thickness of a dried photosensitive resin layer reached a thickness shown in Table 3, and any one kind of Materials-1 to 14 for a photosensitive resin layer was applied onto a 16 μm-thick temporary support which was a polyethylene terephthalate film using slit-shaped nozzles, thereby forming a photosensitive resin layer. A protective film (a 38 μm-thick polyethylene terephthalate film) was pressed onto the photosensitive resin layer, thereby producing a transfer film of each of Examples 1 to 10 and Comparative Examples 1 to 9.

[Production and Evaluation of Electrode Protective Film of Electrostatic Capacitance-Type Input Device]

<Yield Point and Breaking Elongation>

A tensile test for obtaining the yield point and the breaking elongation of an electrode protective film of an electrostatic capacitance-type input device is carried out in the following manner.

First, the composition for an electrode protective film of an electrostatic capacitance-type input device on which a tensile test was to be carried out was applied and dried onto CERAPEEL (manufactured by Toray Advanced Film Co., Ltd.) so that the dried thickness reached 20 μm, thereby forming an electrode protective film of an electrostatic capacitance-type input device (hereinafter, referred to as the polymer film) on a CERAPEEL surface. Subsequently, the polymer film formed on the CERAPEEL surface was exposed to a high-pressure mercury lamp at 120 mJ/cm$^2$ and cured, then, was heated at 145° C. for 30 minutes, and then was cut to a 3 cm×5 mm size. After that, the polymer film was peeled off from CERAPEEL. A tensile test was carried out on the obtained polymer film using a tensile tester (TENSILON: manufactured by A&D Company Limited) under an environment of 23° C. and a relative humidity of 50% at a rate of 50 mm/minute, thereby measuring elongation (the degree of stretch) and stress. Meanwhile, conditions for curing the polymer film by exposing the polymer film to a high-pressure mercury lamp at 120 mJ/cm$^2$ and then heating the polymer film at 145° C. for 30 minutes are conditions for fully completing curing. Whether the polymer film is fully cured can be confirmed from the fact that the polymerization ratio does not change even in a case in which the polymer film is additionally heated for 10 minutes.

In this tensile test, the elongation of the polymer film increases as the tensile stress increases, but a phenomenon in which, at a certain stress or higher, the tensile stress decreases in spite of an increase in strain (stretching) occurs. From this phenomenon, the polymer film is determined to be "yielded", and the stress at this point is referred to as the yield point. Polymers showing this behavior are determined to "have a yield point". On the other hand, polymer films in which both the tensile stress and the elongation increase and the polymer films break at a certain stress are determined to "not have a yield point". Meanwhile, examples of commercially available products of binder polymers which can be used to form polymer films having a yield point include BONRON XPS001 and BONRON XPS002 (all trade names: acrylic resin particle dispersion) manufactured by Mitsui Chemicals, Inc., HARDLEN NZ-1001 (trade name: acid-modified olefin resin particle dispersion) manufactured by Toyobo Co., Ltd., and the like. BONRON XPS001 was used for Material-7.

For polymer films not having a yield point, the elongation at the time of breakage was obtained as the breaking elongation.

The obtained results are shown in Table 3.

<Bending Resistance>

A sample having the electrode protective film of an electrostatic capacitance-type input device of each of the examples and the comparative examples laminated at a film thickness of 10 μm on a single surface or both surfaces of a substrate having a thickness of 100 μm, 75 μm, 65 μm, or 50 μm shown in Table 3 was prepared using the following method.

In Examples 1 to 6 and Comparative Examples 1 to 9, the photosensitive resin layer and the temporary support were transferred in this order onto a single surface or both surfaces of a substrate shown in Table 3 using the transfer film of each of Examples 1 to 6 and Comparative Examples 1 to 9 from which the protective film had been peeled off, thereby obtaining a laminate (the temperature of the substrate: 40° C., the rubber roller temperature: 110° C., the linear pressure: 3 N/cm, and the transportation rate: 2 m/minute). After that, using a proximity-type stepper having an ultrahigh-pressure mercury lamp (manufactured by Hitachi High-Tech Fielding Corporation), the distance between an exposure mask (a silica exposure mask having a pattern for forming an overcoat) surface and the temporary support was set to 125 μm, and the obtained laminate was pattern-exposed through the temporary support at an exposure amount of 100 mJ/cm$^2$ (i rays). After the peeling of the temporary support, a washing treatment was carried out on the pattern-exposed laminate (film substrate) at 32° C. for 60 seconds using an aqueous solution of 2% by mass of sodium carbonate. Ultrapure water was sprayed to the washing-treated substrate from ultrahigh-pressure washing nozzles, thereby removing residues. Subsequently, moisture on the substrate was removed by blowing the air, and a heating (post-basking) treatment was carried out at 145° C. for 30 minutes, thereby preparing a sample in which the photosensitive resin layer was laminated on the substrate.

In bending resistance tests of Examples 7 to 10, laminates of Examples 7 to 10 produced using the following method were used as samples having an electrode of an electrostatic capacitance-type input device and a photosensitive resin layer laminated on a 100 μm-thick substrate. Furthermore, samples for which substrates including an electrode of an electrostatic capacitance-type input device produced in the same manner as Substrate-1 or Substrate-2 except for the fact that, in the production of the laminates of Examples 7 to 10, the thickness of the substrate was respectively changed to 75 μm, 65 μm, and 50 μm were used were produced, and samples in which an electrode of an electrostatic capacitance-type input device and a photosensitive resin layer were laminated on a 75 μm, 65 μm, or 50 μm-thick substrate were prepared.

A Mandrel test regarding bending resistance was carried out using a Mandrel tester according to Japanese Industrial Standards (JIS) K5600 and a metallic rod having a diameter of 2 mm. A test of repeatedly winding each of the samples around the metallic rod 1,000 times was carried out, and the appearance was observed using a microscope.

Samples on which appearance abnormality such as cracking or whitening was observed and samples on which appearance abnormality was not observed were evaluated according to the following standards. Meanwhile, as the thickness of the substrate increases, appearance abnormality is more likely to occur after the Mandrel test.

A: Appearance abnormality is observed in a case in which the electrode protective film of an electrostatic capacitance-type input device is laminated on the substrate having a thickness of 100 μm.

B: Appearance abnormality is observed in a case in which the electrode protective film of an electrostatic capacitance-type input device is laminated on the substrate having a thickness of 100 μm, but appearance abnormality is not observed in a case in which the electrode protective film of an electrostatic capacitance-type input device is laminated on the substrate having a thickness of 75 μm, 65 μm, or 50 μm.

C: Appearance abnormality is observed in a case in which the electrode protective film of an electrostatic capacitance-type input device is laminated on the substrate having a thickness of 100 μm or 75 μm, but appearance abnormality is not observed in a case in which the electrode protective film of an electrostatic capacitance-type input device is laminated on the substrate having a thickness of 65 μm or 50 μm.

D: Appearance abnormality is observed in a case in which the electrode protective film of an electrostatic capacitance-type input device is laminated on the substrate having a thickness of 100 μm, 75 μm, or 65 μm, but appearance abnormality is not observed in a case in which the electrode protective film of an electrostatic capacitance-type input device is laminated on the substrate having a thickness of 50 μm.

E: Appearance abnormality is observed in a case in which the electrode protective film of an electrostatic capacitance-type input device is laminated on the substrate having a thickness of 100 μm, 75 μm, 65 μm, or 50 μm.

The obtained results are shown in Table 3.

[Production of Substrate Including Electrode of Electrostatic Capacitance-Type Input Device]

In Examples 7 to 10, the electrode protective film of an electrostatic capacitance-type input device of each of Examples 7 to 10 was formed on a substrate including an electrode of an electrostatic capacitance-type input device, thereby producing a laminate of each of Examples 7 to 10.

First, the substrate including an electrode of an electrostatic capacitance-type input device was produced using the following method.

<Substrate-1>

(Preparation of Silver Halide Emulsion)

Liquid 2 and Liquid 3 which respectively amounted to 90% of the amounts below were added at the same time under stirring for 20 minutes to Liquid 1 which had been held at 38° C. and a pH of 4.5, thereby forming 0.16 μm-sized silver halide nuclear particles. Subsequently, Liquid 4 and Liquid 5 were added thereto for eight minutes, furthermore, Liquid 2 and Liquid 3 which respectively amounted to the remaining 10% were added thereto for two minutes, thereby causing silver halide particles to grow up to 0.21 Furthermore, potassium iodide (0.15 g) was added thereto and aged for five minutes, thereby finishing the silver formation of the silver halide particles.

Liquid 1:

| | |
|---|---|
| Water | 750 ml |
| Gelatin | 9 g |
| Sodium chloride | 3 g |
| 1,3-Dimethylimidazolidine-2-thione | 20 mg |
| Sodium benzenethiosulfonate | 10 mg |
| Citric acid | 0.7 g |

Liquid 2:

| | |
|---|---|
| Water | 300 ml |
| Silver nitrate | 150 g |

Liquid 3:

| | |
|---|---|
| Water | 300 ml |
| Sodium Chloride | 38 g |
| Potassium bromide | 32 g |
| Potassium hexachloroiridate (III) | 8 ml |
| (Aqueous solution of 20% by mass of 0.005% KCl) | |
| Ammonium hexachlororhodate | 10 ml |
| (Aqueous solution of 20% by mass of 0.001% NaCl) | |

Liquid 4:

| | |
|---|---|
| Water | 100 ml |
| Silver nitrate | 50 g |

Liquid 5:

| | |
|---|---|
| Water | 100 ml |
| Sodium chloride | 13 g |
| Potassium bromide | 11 g |
| Yellow prussiate of potash | 5 mg |

After that, the silver halide particles were water-washed using a flocculation method according to a normal method. Specifically, the temperature was lowered to 35° C., and the pH was decreased using sulfuric acid until the silver halide particles were precipitated (the pH was in a range of 3.6±0.2). Next, a supernatant liquid (approximately 3 liters) was removed (first water washing). Distilled water (3 liters) was further added thereto, and then sulfuric acid was added thereto until silver halide was precipitated. Again, a supernatant liquid (approximately 3 liters) was removed (second water washing). The same operation as the second water washing was further repeated once (third water washing), and a water washing and desalination step was finished. An emulsion after the water washing and desalination was adjusted to a pH of 6.4 and a pAg of 7.5, gelatin (3.9 g), sodium benzenethiosulfonate (10 mg), sodium benzenethiosulfinate (3 mg), sodium thiosulfate (15 mg), and chlorauric acid (10 mg) were added thereto, chemical sensitization was carried out at 55° C. so as to obtain the optimal sensitivity, and 1,3,3a,7-tetraazaindene (100 mg) as a stabilizer and PROXEL (trade name, manufactured by ICI Co., Ltd.) (100 mg) as a preservative were added thereto. The finally-obtained emulsion was an iodine salt silver chlorobromide cubic particle emulsion having an average particle diameter of 0.22 μm and a variation coefficient of 9% which included 0.08 mol % of silver iodide and had a ratio of a silver chlorobromide set to 70 mol %:30 mol % (silver chloride: silver bromide).

(Preparation of Composition for Forming Silver Salt Emulsion Layer)

1,3,3a,7-Tetraazaindene ($1.2 \times 10^{-4}$ mol/mol Ag), hydroquinone ($1.2 \times 10^{-2}$ mol/mol Ag), citric acid ($3.0 \times 10^{-4}$ mol/mol Ag), and 2,4-dichloro-6-hydroxy-1,3,5-triazine sodium salt (0.90 g/mol Ag) were added to the elusion, and the pH of a coating fluid was adjusted to 5.6 using citric acid, thereby obtaining a composition for forming a silver salt emulsion layer.

(Silver Salt Emulsion Layer-Forming Step)

After a corona discharge treatment was carried out on a 100 μm-thick polyethylene terephthalate (PET) film, 0.1 μm-thick gelatin layers were provided as undercoats on both surfaces of the PET film, and, furthermore, antihalation layers including a dye which had an optical density of approximately 1.0 and was decolored by alkalis in a developer were provided on the undercoats. The composition for forming a silver salt emulsion layer was applied onto the antihalation layers, and furthermore, 0.15 μm-thick gelatin layers were provided, thereby obtaining a PET film having silver salt emulsion layers formed on both surfaces. The obtained film was considered as Film A. In the formed silver salt emulsion layer, the amount of silver was 6.0 g/m$^2$, and the amount of gelatin was 1.0 g/m$^2$.

(Exposure and Development Step)

Both surfaces of Film A were exposed to parallel light from a light source of a high-pressure mercury lamp through a photomask on which a comb-type pattern having a line and space (line/space, hereinafter, also referred to as L/S) of 50 μm/50 μm was disposed. After the exposure, the surfaces were developed using a developer below, and furthermore, a development treatment was carried out using a fixing liquid (trade name: N3X-R for CN16X, manufactured by Fujifilm Corporation). Furthermore, the surfaces were rinsed with pure water and dried, thereby obtaining a PET film having electrode patterns made of a fine Ag wire (fine metal wire) and the gelatin layers formed on both surfaces. The gelatin layer was formed between the fine Ag wires, and the amount of Ag in the fine Ag wire at this time was found to be 5.5 g/m2 from a fluorescent X-ray analysis. The obtained comb-type wiring pattern-attached film was considered as Substrate-1.

(Composition of Developer)

| One liter (L) of the developer includes the following compounds. | |
|---|---|
| Hydroquinone | 0.037 mol/L |
| N-Methylaminophenol | 0.016 mol/L |
| Sodium metaborate | 0.140 mol/L |
| Sodium hydroxide | 0.360 mol/L |
| Sodium bromide | 0.031 mol/L |
| Potassium metabisulfite | 0.187 mol/L |

<Substrate-2>

Substrate-2 having a conductive film 1 patterned as described below was produced. Meanwhile, the amount of Ag was found to be 0.015 g/m$^2$ from a fluorescent X-ray analysis.

(Production of Silver Nanowire Dispersion Liquid)

—Preparation of Silver Nanowire Dispersion Liquid (1)—

Silver nitrate powder (60 g) was dissolved in propylene glycol (370 g), thereby preparing a silver nitrate solution 101. Polyvinyl pyrrolidone (molecular weight: 55,000) (72.0 g) was added to propylene glycol (4.45 kg), and the temperature was increased to 90° C. while nitrogen gas was caused to pass through a gas-phase portion of a container. This liquid was considered as a reaction liquid 101. The silver nitrate solution 101 (2.50 g) was added to the reaction liquid 101 under violent stirring while maintaining the passing of the nitrogen gas, thereby carrying out heating and stirring for one minute. Furthermore, a solution obtained by dissolving tetrabutylammonium chloride (11.8 g) in propylene glycol (100 g) was added to this solution, thereby producing a reaction liquid 102.

The silver nitrate solution 101 (200 g) was added at an addition rate of 50 cm$^3$/minute to the reaction liquid 102 which was held at 90° C. under stirring at a stirring rate of 500 rpm (revolution per minute). The stirring rate was dropped to 100 rpm, the passing of the nitrogen gas was stopped, and heating and stirring was carried out for 15 hours. The silver nitrate solution 101 (220 g) was added at an addition rate of 0.5 cm$^3$/minute to the reaction liquid which was held at 90° C. under stirring at a stirring rate of 100 rpm, and heating and stirring was continued for two hours from the end of the addition. The stirring rate was changed to 500 rpm, distilled water (1.0 kg) was added thereto, and then the mixture was cooled to 25° C., thereby producing a reaction liquid 101.

Ultrafiltration was carried out in the following manner using an ultrafiltration module having a molecular weight cut off of 150,000. The addition of a liquid mixture of distilled water and 1-propanol (volume ratio of 1:1) to the reaction liquid 101 and the condensation of the reaction liquid 101 were repeated until the conductivity of a filtrate reached 50 µS/cm or less in the end. Condensation was carried out, and a silver nanowire dispersion liquid (1) having a metal content of 0.45% by mass was obtained.

For a silver nanowire in the obtained silver nanowire dispersion liquid (1), the average minor length and the average major length were measured. As a result, the average minor length was 28.5 nm, and the average major length was 15.2 µm. Hereinafter, in the case of being referred to as "the silver nanowire dispersion liquid (1)", the silver nanowire dispersion liquid is a silver nanowire dispersion liquid obtained using the above-described method.

(Production of Conductive Film 1)

A solution of an alkoxide compound having the following composition was stirred at 60° C. for one hour and was confirmed to be uniform. As a result of measuring the weight-average molecular weight of the obtained sol-gel liquid by means of (polystyrene equivalent) GPC, the weight-average molecular weight was 4,400. The sol-gel liquid (2.24 parts) and the silver nanowire dispersion liquid (1) prepared using the above-described method (17.76 parts) were mixed together and, furthermore, diluted with distilled water and 1-propanol, thereby obtaining a silver nanowire coating fluid (1). The solvent ratio in the obtained coating fluid was 60:40 (distilled water: 1-propanol, volume ratio). The silver nanowire coating fluid (1) was applied onto a PET substrate (thickness: 100 µm) using a bar coating method so that the amount of silver reached 0.015 g/m$^2$ and the application amount of the total solid content reached 0.120 g/m$^2$ and then dried at 120° C. for one minute, thereby forming a conductive film 1 containing the silver nanowire.

(Solution of Alkoxide Compound)

| | |
|---|---|
| Tetraethoxysilane (KBE-04, manufactured by Shin-Etsu Chemical Co., Ltd.) | 5.0 parts |
| Aqueous solution of 1% by mass of acetic acid | 11.0 parts |
| Distilled water | 4.0 parts |

(Patterning of Conductive Film 1)

A photoresist (TMSMR-8900LB: manufactured by Tokyo Ohka Kogyo Co., Ltd.) was applied to the conductive film 1 by means of spin coating and was fired at 90° C. for 60 seconds. Next, pattern exposure (exposure amount: 12 mW/cm$^2$, 20 seconds) was carried out using the photo mask, the pattern was developed using a developer (NMD-W: manufactured by Tokyo Ohka Kogyo Co., Ltd.), was water-washed and dried, and then fired at 120° C. for 60 seconds, thereby forming a photoresist patterned on the conductive film 1.

Next, after immersed in a silver etching liquid (SEA-2: manufactured by Kanto Chemical Co., Inc.) for 30 seconds, the photoresist was water-washed and dried so as to etch the silver nanowire, thereby forming a non-conductive portion in the conductive film 1. After that, the photoresist was peeled off using a neutral peeling liquid (PK-SFR8120: manufactured by Parker Corporation), and then water-washed and dried, thereby producing a conductive film 1 patterned to a comb-shaped electrode pattern (L/S=50 µm/50 µm).

[Production of Laminates]

A photosensitive resin layer and a temporary support were transferred in this order to a single surface or both surfaces of a substrate including an electrode of an electrostatic capacitance-type input device shown in Table 3 using the transfer film of each of Examples 7 to 10 from which the protective film was peeled off, thereby obtaining a laminate (the temperature of the substrate: 40° C., the rubber roller temperature: 110° C., the linear pressure: 3 N/cm, and the transportation rate: 2 m/minute).

After that, using a proximity-type stepper having an ultrahigh-pressure mercury lamp (manufactured by Hitachi High-Tech Fielding Corporation), the distance between an exposure mask (a silica exposure mask having a pattern for forming an overcoat) surface and the temporary support was set to 125 µm, and the obtained laminate was pattern-exposed through the temporary support at an exposure amount of 100 mJ/cm$^2$ (i rays). After the peeling of the temporary support, a washing treatment was carried out on the pattern-exposed laminate (film substrate) at 32° C. for 60 seconds using an aqueous solution of 2% by mass of sodium carbonate. Ultrapure water was sprayed to the washing-treated substrate from ultrahigh-pressure washing nozzles, thereby removing residues. Subsequently, moisture on the substrate was removed by blowing the air, and a heating (post-basking) treatment was carried out at 145° C. for 30 minutes, thereby obtaining a laminate including an electrode pattern (an electrode of an electrostatic capacitance-type input device) and a photosensitive resin layer in this order on the substrate. The obtained laminate was considered as a laminate of each of Examples 7 to 10.

<Electric Conduction Test>

An electric conduction test was carried out by attaching a tester to a terminal of the electrode pattern in the laminate of each of Examples 7 to 10 and measuring the wire resistance.

The wire resistance was measured using a digital multi-meter (M3500 manufactured by PICOTEST). Five levels of an electrode pattern having the mesh pattern illustrated in FIG. 16 and FIG. 17 were prepared in each of the examples, and the average value of the resistance values was considered as the wire electrical resistance of the electrode pattern having the mesh pattern.

A Mandrel test was carried out on the laminate of each of Examples 7 to 10 in the same manner as the Mandrel test for the electrode protective film of an electrostatic capacitance-type input device. Laminates in which the wire electrical resistance changed 10% or less before and after the Mandrel test were evaluated as A in the electric conduction test, and laminates in which the wire electrical resistance changed more than 10% were evaluated as B in the electric conduction test. The obtained results are shown in Table 3.

TABLE 3

| | | | | Composition for electrode protective film of electrostatic capacitance-type input device | | | |
|---|---|---|---|---|---|---|---|
| | | | | (b) Photopolymerizable compound | | | |
| | Substrate | Electrode Kind | Material | Weight-average molecular weight per ethylenic unsaturated group (maximum value) | Ratio of photopolymerizable compound in which value obtained by dividing weight-average molecular weight by average number of polymerizable groups is 270 or more to all of (b) photopolymerizable compound (% by mass) | Ratio of photopolymerizable compound in which value obtained by dividing weight-average molecular weight by average number of polymerizable groups is 270 or more to total solid content (% by mass) | (d) Compound capable of reacting with acidic groups or alcoholic hydroxy groups by heating |
| Example 1 | PET | — | Material-1 | 354 | 25.07 | 7.92 | Included |
| Example 2 | PET | — | Material-1 | 354 | 25.07 | 7.92 | Included |
| Example 3 | PET | — | Material-2 | 217 | 21.63 | 8.80 | Included |
| Example 4 | PET | — | Material-3 | 2250 | 38.10 | 17.93 | Included |
| Example 5 | PET | — | Material-4 | 800 | 44.38 | 21.46 | Included |
| Comparative Example 1 | PET | — | Material-5 | 157 | 0.00 | 0.00 | — |
| Comparative Example 2 | PET | — | Material-6 | 157 | 0.00 | 0.00 | — |
| Comparative Example 3 | PET | — | Material-7 | 168 | 0.00 | 0.00 | — |
| Comparative Example 4 | PET | — | Material-8 | 432 | 24.80 | 10.87 | — |
| Comparative Example 5 | PET | — | Material-9 | 2250 | 33.50 | 18.49 | — |
| Example 6 | PET | — | Material-10 | 278 | 39.87 | 19.95 | Included |
| Comparative Example 6 | PET | — | Material-11 | 157 | 0.00 | 0.00 | Included |
| Comparative Example 7 | PET | — | Material-12 | 157 | 0.00 | 0.00 | Included |
| Comparative Example 8 | PET | — | Material-13 | 168 | 0.00 | 0.00 | Included |
| Comparative Example 9 | PET | — | Material-14 | 248 | 0.00 | 0.00 | Included |
| Example 7 | Substrate-1 | Ag | Material-1 | 354 | 25.07 | 7.92 | Included |
| Example 8 | Substrate-2 | Ag | Material-2 | 432 | 21.63 | 8.80 | Included |
| Example 9 | Substrate-1 | Ag | Material-3 | 2250 | 38.10 | 17.93 | Included |
| Example 10 | Substrate-2 | Ag | Material-4 | 800 | 44.38 | 21.46 | Included |

TABLE 3-continued

| | | | Electrode protective film of electrostatic capacitance-type input device | | | | |
|---|---|---|---|---|---|---|---|
| | | Yield point | Breaking elongation (%) | Film thickness (μm) | Film formation | Bending resistance | Laminate Electric conduction test |
| | Example 1 | Absent | 5.1 | 10 | Single surface | A | — |
| | Example 2 | Absent | 5.1 | 10 | Both surfaces | A | — |
| | Example 3 | Absent | 5.1 | 10 | Both surfaces | A | — |
| | Example 4 | Absent | 5 | 10 | Both surfaces | A | — |
| | Example 5 | Absent | 5.2 | 10 | Both surfaces | A | — |
| | Comparative Example 1 | Absent | 2.4 | 10 | Both surfaces | E | — |
| | Comparative Example 2 | Absent | 2.5 | 10 | Both surfaces | E | — |
| | Comparative Example 3 | Present | — | 10 | Both surfaces | E | — |
| | Comparative Example 4 | Absent | 3.2 | 10 | Both surfaces | E | — |
| | Comparative Example 5 | Absent | 3.3 | 10 | Both surfaces | E | — |
| | Example 6 | Absent | 4.8 | 10 | Both surfaces | B | — |
| | Comparative Example 6 | Absent | 4.2 | 10 | Both surfaces | C | — |
| | Comparative Example 7 | Absent | 4.1 | 10 | Both surfaces | C | — |
| | Comparative Example 8 | Absent | 3.9 | 10 | Both surfaces | D | — |
| | Comparative Example 9 | Absent | 4.4 | 10 | Both surfaces | C | — |
| | Example 7 | Absent | 5.1 | 10 | Single surface | A | A |
| | Example 8 | Absent | 5.1 | 10 | Single surface | A | A |
| | Example 9 | Absent | 5 | 10 | Both surfaces | A | A |
| | Example 10 | Absent | 5.2 | 10 | Both surfaces | A | A |

From Table 3, it was found that the composition for an electrode protective film of an electrostatic capacitance-type input device of the present invention can be used to form electrode protective films of electrostatic capacitance-type input devices having favorable bending resistance.

On the other hand, Comparative Examples 1 to 3 which did not include the photopolymerizable compound in which the value obtained by dividing the weight-average molecular weight by the average number of polymerizable groups is 270 or more and did not include the compound capable of reacting with acidic groups or alcoholic hydroxy groups by heating were evaluated to be as poor as E in terms of the bending resistance.

Comparative Examples 4 and 5 which did not include the compound capable of reacting with acidic groups or alcoholic hydroxy groups by heating were evaluated to be as poor as E in terms of the bending resistance.

Comparative Examples 7 to 9 which did not include the photopolymerizable compound in which the value obtained by dividing the weight-average molecular weight by the average number of polymerizable groups is 270 or more were evaluated to be as poor as C or D in terms of the bending resistance.

[Production of Electrostatic Capacitance-Type Input Device and Image Display Device (Touch Panel)]

To a liquid crystal display device manufactured using the method described in [0097] to [0119] of JP2009-47936A, the laminate of each of Examples 7 to 10 was attached, and, furthermore, a front glass plate was bound, thereby producing an electrostatic capacitance-type input device and an image display device of each of Examples 7 to 10 using a well-known method.

<Evaluation of Electrostatic Capacitance-Type Input Devices and Image Display Devices>

The image display devices including the laminate of each of Examples 7 to 10 were image display devices having favorable bending resistance.

EXPLANATION OF REFERENCES

1: substrate
2: mask layer
3: electrode pattern (first electrode pattern)
3a: pad portion
3b: connection portion
4: electrode pattern (second electrode pattern)
5: insulating layer
6: additional conductive element
7: photosensitive resin layer
8: opening portion
10: electrostatic capacitance-type input device
11: transparent film
12: second photosensitive resin layer
13: laminate
21: region in which electrode pattern and photosensitive resin layer are laminated in this order
22: non-patterned region
α: taper angle
26: temporary support
27: thermoplastic resin layer
28: interlayer
29: protective film
30: transfer film
31: terminal portion of guidance wire 33: cured portion of photosensitive resin layer
34: opening portion corresponding to terminal portion of guidance wire (non-cured portion of photosensitive resin layer)
C: first direction
D: second direction

What is claimed is:

1. A composition for an electrode protective film of an electrostatic capacitance-type input device comprising:
   (a) a binder polymer which is an acrylic resin having carboxyl groups;
   (b) a photopolymerizable compound having an ethylenic unsaturated group;
   (c) a photopolymerization initiator; and
   (d) a compound capable of reacting with acidic groups or alcoholic hydroxy groups by heating,
   wherein (b) the photopolymerizable compound having an ethylenic unsaturated group includes (b1) a photopolymerizable compound in which a value obtained by dividing a weight-average molecular weight by an average number of polymerizable groups is 270 or more,
   (d) the compound capable of reacting with acidic groups or alcoholic hydroxy groups by heating has no ethylenic unsaturated group,
   the ratio of (b1) the photopolymerizable compound in which a value obtained by dividing the weight-average molecular weight by an average number of polymerizable groups is 270 or more to all of (b) the photopolymerizable compound having an ethylene ethylenic unsaturated group is from 15% by mass to 60% by mass; and
   the photopolymerizable compound (b1) in which a value obtained by dividing a weight-average molecular weight by an average number of polymerizable groups is 270 or more is a difunctional or a trifunctional photopolymerizable compound.

2. The composition for an electrode protective film of an electrostatic capacitance-type input device according to claim 1,
   wherein, in an electrode protective film of an electrostatic capacitance-type input device obtained by curing the composition for an electrode protective film of an electrostatic capacitance-type input device, a breaking elongation is 5% or more in a tensile test under an environment of 23° C. and a relative humidity of 50%.

3. The composition for an electrode protective film of an electrostatic capacitance-type input device according to claim 1,
   wherein (b) the photopolymerizable compound having an ethylenic unsaturated group includes (b1-1) a photopolymerizable compound in which a value obtained by dividing a weight-average molecular weight by an average number of polymerizable groups is 800 or more.

4. The composition for an electrode protective film of an electrostatic capacitance-type input device according to claim 1,
   wherein, in the composition for an electrode protective film of an electrostatic capacitance-type input device, a ratio of (b1) the photopolymerizable compound in which a value obtained by dividing a weight-average molecular weight by an average number of polymerizable groups is 270 or more to all of (b) the photopolymerizable compound having an ethylenic unsaturated group is 15% by mass to 44.38% by mass.

5. The composition for an electrode protective film of an electrostatic capacitance-type input device according to claim 1,
   wherein, in the composition for an electrode protective film of an electrostatic capacitance-type input device, a ratio of (b1) the photopolymerizable compound in which a value obtained by dividing a weight-average molecular weight by an average number of polymerizable groups is 270 or more to a total solid content is 5% by mass or more.

6. The composition for an electrode protective film of an electrostatic capacitance-type input device according to claim 1,
   wherein (d) the compound capable of reacting with acidic groups or alcoholic hydroxy groups by heating is a blocked isocyanate.

7. The composition for an electrode protective film of an electrostatic capacitance-type input device according to claim 1,
   wherein (d) the compound capable of reacting with acidic groups or alcoholic hydroxy groups by heating is a compound having a structure represented by General Formula (1);

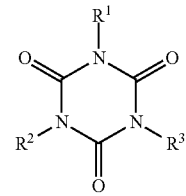

General Formula (1)

in General Formula (1), $R^1$ to $R^3$ each independently represent a monovalent organic group.

8. An electrode protective film of an electrostatic capacitance-type input device formed, over a substrate, of the composition for an electrode protective film of an electrostatic capacitance-type input device according to claim 1.

9. A transfer film comprising:
   a temporary support; and
   a photosensitive resin layer including the composition for an electrode protective film of an electrostatic capacitance-type input device according to claim 1,
   wherein the thickness of the photosensitive resin layer is 2 to 15 μm.

10. A laminate comprising:
    an electrode protective film of an electrostatic capacitance-type input device formed by transferring the electrode protective film of an electrostatic capacitance-type input device according to claim 8 onto a substrate including an electrode of an electrostatic capacitance-type input device.

11. A laminate comprising:
    a substrate including an electrode of an electrostatic capacitance-type input device; and
    a photosensitive resin layer located on the substrate,
    wherein the photosensitive resin layer includes (a) a binder polymer which is an acrylic resin having carboxyl groups, (b) a photopolymerizable compound having an ethylenic unsaturated group, (c) a photopolymerization initiator, and (d) a compound capable of reacting with acidic groups or alcoholic hydroxy groups by heating, (b) the photopolymerizable compound having an ethylenic unsaturated group includes (b1) a photopolymerizable compound in which a value obtained by dividing a weight-average molecular weight by an average number of polymerizable groups is 270 or more, (d) the compound capable of reacting with acidic groups or alcoholic hydroxy groups by heating has no ethylenic unsaturated group, the ratio of (b1) the photopolymerizable compound in which a value obtained by dividing the weight-average molecular weight by an average number of polymerizable groups is 270 or more to all of (b) the photopolymerizable compound having an ethylenic unsaturated group is from 15% by mass to 60% by mass, and the photopolymerizable compound (b1) in which a value obtained by dividing a weight-average molecular weight by an average number of polymerizable groups is 270 or more is a difunctional or a trifunctional photopolymerizable compound.

12. The laminate according to claim 10,
wherein the electrode of an electrostatic capacitance-type input device includes at least one kind of metal selected from Au, Ag, Cu, and Al or an alloy including at least one kind of metal selected from Au, Ag, Cu, and Al.

13. The laminate according to claim 11,
wherein the photosensitive resin layer is cured.

14. An electrostatic capacitance-type input device comprising:
the laminate according to claim 10.

15. An image display device comprising:
the electrostatic capacitance-type input device according to claim 14.

16. The composition for an electrode protective film of an electrostatic capacitance-type input device according to claim 1,
wherein (d) the compound capable of reacting with acidic groups or alcoholic hydroxy groups by heating is a blocked isocyanate protected with a thermally dissociable blocking agent, and
the thermally dissociable blocking agent is at least one of an oxime-based compound, an acid amide-based compound, an amine-based compound, an active methylene-based compound, and a pyrazole-based compound.

17. The composition for an electrode protective film of an electrostatic capacitance-type input device according to claim 1,
wherein, in the composition for an electrode protective film of an electrostatic capacitance-type input device, a ratio of (b1) the photopolymerizable compound in which a value obtained by dividing a weight-average molecular weight by an average number of polymerizable groups is 270 or more to all of (b) the photopolymerizable compound having an ethylenic unsaturated group is 20% by mass to 50% by mass.

18. The composition for an electrode protective film of an electrostatic capacitance-type input device according to claim 1,
wherein (b) the photopolymerizable compound having an ethylenic unsaturated group includes two or more kinds of the photopolymerizable compounds other than (b1) the photopolymerizable compound in which a value obtained by dividing a weight-average molecular weight by an average number of polymerizable groups is 270 or more.

19. The composition for an electrode protective film of an electrostatic capacitance-type input device according to claim 1,
wherein at least one kind of (b) the photopolymerizable compound having an ethylenic unsaturated group contains a carboxyl group.

20. The composition for an electrode protective film of an electrostatic capacitance-type input device according to claim 1,
wherein (b) the photopolymerizable compound having an ethylenic unsaturated group includes a urethane (meth) acrylate compound.

21. A composition for an electrode protective film of an electrostatic capacitance-type input device comprising:
(a) a binder polymer which is an acrylic resin having carboxyl groups;
(b) a photopolymerizable compound having an ethylenic unsaturated group;
(c) a photopolymerization initiator; and
(d) a compound capable of reacting with acidic groups or alcoholic hydroxy groups by heating,
wherein (b) the photopolymerizable compound having an ethylenic unsaturated group includes (b1) a photopolymerizable compound in which a value obtained by dividing the weight-average molecular weight by an average number of polymerizable groups is from 800 to 3000,
(d) the compound capable of reacting with acidic groups or alcoholic hydroxy groups by heating has no ethylenic unsaturated group,
the ratio of (b1) the photopolymerizable compound in which a value obtained by dividing the weight-average molecular weight by an average number of polymerizable groups is from 800 to 3000 to all of (b) the photopolymerizable compound having an ethylenic unsaturated group is from 15% by mass to 60% by mass, and
the photopolymerizable compound (b1) in which a value obtained by dividing a weight-average molecular weight by an average number of polymerizable groups is 270 or more is a difunctional or a trifunctional photopolymerizable compound.

22. The composition for an electrode protective film of an electrostatic capacitance-type input device according to claim 21, wherein, in an electrode protective film of an electrostatic capacitance-type input device obtained by curing the composition for an electrode protective film of an electrostatic capacitance-type input device, the breaking elongation is 5% or more in a tensile test under an environment of 23° C. and a relative humidity of 50%.

23. A composition for an electrode protective film of an electrostatic capacitance-type input device comprising:
(a) a binder polymer which is an acrylic resin having carboxyl groups;
(b) a photopolymerizable compound having an ethylenic unsaturated group;
(c) a photopolymerization initiator; and
(d) a compound capable of reacting with acidic groups or alcoholic hydroxy groups by heating,
wherein (b) the photopolymerizable compound having an ethylenic unsaturated group includes (b1) a photopolymerizable compound in which a value obtained by dividing the weight-average molecular weight by an average number of polymerizable groups is 270 or more,
(d) the compound capable of reacting with acidic groups or alcoholic hydroxy groups by heating is a blocked isocyanate having no ethylenic unsaturated group and is a compound having a structure represented by General Formula (1):

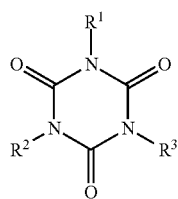

General Formula (1)

in General Formula (1), $R^1$ to $R^3$ each independently represents a monovalent organic group, the ratio of (b1) the photopolymerizable compound in which a value obtained by dividing the weight-average molecular weight by an average number of polymerizable groups is 270 or more to all of (b) the photopolymerizable compound having an ethylene ethylenic unsaturated group is from 15% by mass to 60% by mass; and the photopolymerizable compound (b1) in which a value obtained by dividing a weight-average molecular weight by an average number of polymerizable groups is 270 or more is a difunctional or a trifunctional photopolymerizable compound.

24. A transfer film comprising:
a temporary support; and
a photosensitive resin layer including the composition for an electrode protective film of an electrostatic capacitance-type input device according to claim 21,
wherein the thickness of the photosensitive resin layer is 2 to 15 μm.

25. A transfer film comprising:
a temporary support; and
a photosensitive resin layer including the composition for an electrode protective film of an electrostatic capacitance-type input device according to claim 22,
wherein the thickness of the photosensitive resin layer is 2 to 15 μm.

26. A transfer film comprising:
a temporary support; and
a photosensitive resin layer including the composition for an electrode protective film of an electrostatic capacitance-type input device according to claim 23,
wherein the thickness of the photosensitive resin layer is 2 to 15 μm.

27. An electrode protective film of an electrostatic capacitance-type input device formed of the composition for an electrode protective film of an electrostatic capacitance-type input device according to claim 21.

28. An electrode protective film of an electrostatic capacitance-type input device formed of the composition for an electrode protective film of an electrostatic capacitance-type input device according to claim 22.

29. An electrode protective film of an electrostatic capacitance-type input device formed of the composition for an electrode protective film of an electrostatic capacitance-type input device according to claim 23.

30. A laminate comprising:
an electrode protective film of an electrostatic capacitance-type input device formed by transferring the electrode protective film of an electrostatic capacitance-type input device according to claim 27 onto a substrate including an electrode of an electrostatic capacitance-type input device.

31. A laminate comprising:
an electrode protective film of an electrostatic capacitance-type input device formed by transferring the electrode protective film of an electrostatic capacitance-type input device according to claim 28 onto a substrate including an electrode of an electrostatic capacitance-type input device.

32. A laminate comprising:
an electrode protective film of an electrostatic capacitance-type input device formed by transferring the electrode protective film of an electrostatic capacitance-type input device according to claim 29 onto a substrate including an electrode of an electrostatic capacitance-type input device.

33. A laminate comprising:
an electrode protective film of an electrostatic capacitance-type input device formed by transferring an electrode protective film of an electrostatic capacitance-type input device formed of the following composition for an electrode protective film of an electrostatic capacitance-type input device onto a substrate including an electrode of an electrostatic capacitance-type input device, said composition for an electrode protective film of an electrostatic capacitance-type input device comprising:

(a) a binder polymer which is an acrylic resin having carboxyl groups;

(b) a photopolymerizable compound having an ethylenic unsaturated group;

(c) a photopolymerization initiator; and (d) a compound capable of reacting with acidic groups or alcoholic hydroxy groups by heating, wherein (b) the photopolymerizable compound having an ethylenic unsaturated group includes (b1) a photopolymerizable compound in which a value obtained by dividing the weight-average molecular weight by an average number of polymerizable groups is 270 or more, (d) the compound capable of reacting with acidic groups or alcoholic hydroxy groups by heating has no ethylenic unsaturated group, the ratio of (b1) the photopolymerizable compound in which a value obtained by dividing the weight-average molecular weight by an average number of polymerizable groups is 270 or more to all of (b) the photopolymerizable compound having an ethylenic unsaturated group is from 15% by mass to 60% by mass, and the photopolymerizable compound (b1) in which a value obtained by dividing a weight-average molecular weight by an average number of polymerizable groups is 270 or more is a difunctional or a trifunctional photopolymerizable compound.

34. The laminate according to claim 33,
wherein the electrode of an electrostatic capacitance-type input device includes at least one kind of metal selected from Au, Ag, Cu, and Al or an alloy including at least one kind of metal selected from Au, Ag, Cu, and Al.

35. The laminate according to claim 33,
wherein the composition is cured.

36. An electrostatic capacitance-type input device comprising:
the laminate according to claim 33.

37. An image display device comprising:
the electrostatic capacitance-type input device according to claim 36.

38. The composition for an electrode protective film of an electrostatic capacitance-type input device according to claim 1,
wherein, in the composition for an electrode protective film of an electrostatic capacitance-type input device, a ratio of (b1) the photopolymerizable compound in which a value obtained by dividing a weight-average molecular weight by an average number of polymerizable groups is 270 or more to the total solid content is 7% or more.

39. The laminate according to claim 35,
wherein, in the composition for an electrode protective film of an electrostatic capacitance-type input device, a ratio of (b1) the photopolymerizable compound in which a value obtained by dividing a weight-average molecular weight by an average number of polymerizable groups is 270 or more to the total solid content is 7% or more; and
a ratio of (b1) the photopolymerizable compound in which a value obtained by dividing a weight-average molecular weight by an average number of polymerizable groups is 270 or more to all of (b) the photopolymerizable compound having an ethylenic unsaturated group is from 15% by mass to 44.38% by mass.

40. The laminate according to claim 11,
wherein the ratio of (b1) the photopolymerizable compound in which a value obtained by dividing the weight-average molecular weight by an average number of polymerizable groups is 270 or more to all of (b) the photopolymerizable compound having an ethylenic unsaturated group is from 15% by mass to 44.38% by mass.

41. The laminate according to claim 33,
wherein the ratio of (b1) the photopolymerizable compound in which a value obtained by dividing the weight-average molecular weight by an average number of polymerizable groups is 270 or more to all of (b) the photopolymerizable compound having an ethylene ethylenic unsaturated group is from 15% by mass to 44.38% by mass.

* * * * *